(12) United States Patent
Esposito et al.

(10) Patent No.: US 9,334,251 B2
(45) Date of Patent: May 10, 2016

(54) COMPOUNDS FOR THE TREATMENT OF NEURODEGENERATIVE DISEASES

(71) Applicant: PROTAMED, INC., Kirkland, WA (US)

(72) Inventors: Luke A Esposito, Seattle, WA (US); Marisa C Yadon, Brea (ZA); Joel Cummings, Seattle, WA (US); F Michael Hudson, Oakland, CA (US); Thomas Lake, Snohomish, WA (US); Qubai Hu, Kirkland, WA (US); Judy Cam, Bellevue, WA (US); Alan D Snow, Lynnwood, WA (US)

(73) Assignee: PROTAMED, INC., Kirkland, WA (US)

( * ) Notice: Subject to any disclaimer, the term of this patent is extended or adjusted under 35 U.S.C. 154(b) by 0 days.

(21) Appl. No.: 14/740,595

(22) Filed: Jun. 16, 2015

(65) Prior Publication Data

US 2015/0274681 A1    Oct. 1, 2015

Related U.S. Application Data

(62) Division of application No. 14/486,040, filed on Sep. 15, 2014, now Pat. No. 9,085,549, which is a division of application No. 14/002,164, filed as application No. PCT/US2012/027222 on Mar. 1, 2012, now Pat. No. 8,865,754.

(60) Provisional application No. 61/448,935, filed on Mar. 3, 2011.

(51) Int. Cl.
*C07D 263/57* (2006.01)
*C07D 285/08* (2006.01)
*A61K 31/423* (2006.01)
*A61K 31/433* (2006.01)

(52) U.S. Cl.
CPC ............ *C07D 285/08* (2013.01); *C07D 263/57* (2013.01)

(58) Field of Classification Search
None
See application file for complete search history.

(56) References Cited

U.S. PATENT DOCUMENTS

2005/0239851 A1* 10/2005 Malamas ............. C07D 235/18
514/367

OTHER PUBLICATIONS

Ana Castro, Arantxa Encinas, Carmen Gil, Stefan Brase, Williams Porcal, Concepcion Perez, Francisco J Moreno, Ana Martinez. Non-ATP competitive glycogen synthase kinase 3B (GSK-3B) inhibitors: Study of structural requirements for thiadiazolidinon derivatives. Bioorganic & Medicinal Chemistry. 2008. pp. 495-510. vol. 16. Elsevier.

* cited by examiner

*Primary Examiner* — Alicia L Otton
(74) *Attorney, Agent, or Firm* — Sam K. Tahmassebi

(57) ABSTRACT

Compounds and their pharmaceutically acceptable salts for treatment of tauopathies, such as Alzheimer's disease, Pick's disease, progressive supranuclear palsy, corticobasal degeneration, familial frontotemporal dementia/Parkinsonism linked to chromosome 17, amyotrophic lateral sclerosis/Parkinsonism-dementia complex, argyrophilic grain dementia, dementia pugilistic, diffuse neurofibrillary tangles with calcification, progressive subcortical gliosis and tangle only dementia.

8 Claims, 5 Drawing Sheets

COMPOUNDS FOR THE TREATMENT OF NEURODEGENERATIVE DISEASES

CROSS REFERENCE TO RELATED APPLICATIONS

This application is a divisional application of U.S. application Ser. No. 14/486,040 filed Sep. 15, 2014 which is a divisional application of U.S. application Ser. No. 14/002,164 filed Aug. 29, 2013 now U.S. Pat. No. 8,865,754 issued Oct. 21, 2014, which was filed under 35 U.S.C. 371 and is a U.S. National Stage application of PCT/US2012/027222 filed Mar. 1, 2012, and claims priority to U.S. Provisional Application No. 61/448,935, filed Mar. 3, 2011, each entitled "Compounds for the Treatment of Neurodegenerative Diseases", the contents of which are incorporated herein by reference.

TECHNICAL FIELD

Provided herein are compounds, pharmaceutical compositions, and methods for the treatment of neurodegenerative diseases such as Parkinson's disease and various tauopathies.

BACKGROUND OF INVENTION

Parkinson's disease (PD) is a neurodegenerative human disorder characterized clinically by both motor (movement) and non-motor behavioral dysfunction, and histopathologically by the formation, deposition, accumulation and/or persistence of abnormal fibrillar protein deposits and/or aggregates. This accumulation of cytoplasmic Lewy bodies consisting of fibrils/aggregates of $\alpha$-synuclein/NAC (non-A$\beta$ component) is believed important in the pathogenesis of PD. Lewy bodies occur mostly in the substantia nigra and locus ceruleus sections of the brain stem and the olfactory bulb, but also, to a lesser extent, in other subcortical and cortical regions of the brain. Because of this specific localization in the brain, Lewy bodies interfere with the health and integrity of dopaminergic neuronal projections from the substantia nigra to the striatum, thus adversely affecting the ability to initiate, carry out and control voluntary movements. Lewy bodies present in these brain regions may also impact the production of acetylcholine and/or the balance between dopamine and acetylcholine in the brain, thus causing disruption in perception, thinking and behavior as well as other non-motor symptoms including loss of smell and sleep disorders.

Dementia with Lewy Bodies (DLB) is a progressive neurodegenerative disorder characterized by symptoms which display various degrees of manifestation. Such symptoms include progressive dementia, Parkinsonian movement difficulties, hallucinations, and increased sensitivity to neuroleptic drugs. As with Alzheimer's disease (AD), advanced age is considered to be a risk factor for DLB, with average onset typically between the ages of 50-85. Twenty percent of all dementia cases are caused by DLB and over 50% of PD patients develop Parkinson's Disease Dementia (PDD), a type of DLB. DLB may occur alone or in conjunction with other brain abnormalities, including those involved in AD and PD, as mentioned above. Currently, conclusive diagnosis of DLB is made during postmortem autopsy.

New agents or compounds able to bind and/or inhibit $\alpha$-synuclein and/or NAC formation, deposition, accumulation and/or persistence, or disrupt pre-formed $\alpha$-synuclein/NAC fibrils and/or aggregates (or portions thereof) are regarded as potential therapeutics for the treatment of Parkinson's and related synucleinopathies. Compounds which protect neurons from degeneration and damage associated with Parkinson's and related synucleinopathies could also prove useful as therapeutics.

Parkinson's Disease and Synucleinopathies

Parkinson's disease is a neurodegenerative disorder that is pathologically characterized by the presence of intracytoplasmic Lewy bodies (Lewy in *Handbuch der Neurologie*, M. Lewandowski, ed., Springer, Berlin, pp. 920-933, 1912; Pollanen et al., *J. Neuropath. Exp. Neurol.* 52:183-191, 1993), the major components of which are filaments consisting of $\alpha$-synuclein (Spillantini et al., *Proc. Natl. Acad. Sci. USA* 95:6469-6473, 1998; Arai et al., *Neurosci. Lett.* 259:83-86, 1999), a 140-amino acid protein (Ueda et al., *Proc. Natl. Acad. Sci. USA* 90:11282-11286, 1993). Three dominant mutations in $\alpha$-synuclein causing increased tendency to aggregate and resulting in familial early onset Parkinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998; Zarranz et al., *Ann. Neurol.* 55:164-173, 2004). Recently, in vitro studies have demonstrated that recombinant $\alpha$-synuclein can indeed form Lewy body-like fibrils (Conway et al., *Nature Med.* 4:1318-1320, 1998; Hashimoto et al., *Brain Res.* 799:301-306, 1998; Nahri et al., *J. Biol. Chem.* 274:9843-9846, 1999; Choi et al., *FEBS Lett.* 576:363-368, 2004). Most importantly, both the A53T and the E46K Parkinson's disease-linked $\alpha$-synuclein mutations accelerate this fibril-forming aggregation process, demonstrating that such in vitro studies may have relevance for Parkinson's disease pathogenesis. Alpha-synuclein aggregation and fibril formation fulfills the criteria of a nucleation-dependent polymerization process (Wood et al., *J. Biol. Chem.* 274:19509-19512, 1999). Alpha-synuclein recombinant protein, and non-A$\beta$ component (known as NAC), which is a 35-amino acid peptide fragment of $\alpha$-synuclein, both have the ability to form fibrils and/or aggregates when incubated at 37° C., and are positive with stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. USA* 90:11282-11286, 1993).

Synucleins are a family of small, presynaptic neuronal proteins composed of $\alpha$-, $\beta$-, and $\gamma$-synucleins, of which only $\alpha$-synuclein aggregates have been associated with several neurological diseases (Ian et al., *Clinical Neurosc. Res.* 1:445-455, 2001; Trojanowski and Lee, *Neurotoxicology* 23:457-460, 2002). The role of synucleins (and in particular, $\alpha$-synuclein) in the etiology of a number of neurodegenerative diseases has developed from several observations. Pathologically, synuclein was identified as a major component of Lewy bodies, the hallmark inclusions of Parkinson's disease, and a fragment thereof was isolated from amyloid plaques of a different neurological disease, Alzheimer's disease. Biochemically, recombinant $\alpha$-synuclein was shown to form fibrils and/or aggregates that recapitulated the ultrastructural features of $\alpha$-synuclein isolated from patients with dementia with Lewy bodies, Parkinson's disease and multiple system atrophy. Additionally, the identification of mutations within the $\alpha$-synuclein gene, albeit in rare cases of familial Parkinson's disease, demonstrated an unequivocal link between synuclein pathology and neurodegenerative diseases. The common involvement of $\alpha$-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies".

NAC is a 35 amino acid fragment of α-synuclein that has the ability to form fibrils and/or aggregates either in vitro or as observed in the brains of patients with Parkinson's disease. The NAC fragment of α-synuclein is a relatively important therapeutic target as this portion of α-synuclein is believed crucial for formation of Lewy bodies as observed in all patients with Parkinson's disease, synucleinopathies and related disorders.

Currently available therapeutics such as carbidopa/levodopa (Sinemet, Stalevo, Parcopa), dopamine agonists (Apokyn, Parlodel, Neupro, Mirapex, Requip), anticholinergics (Cogentin, Artane), MAO-B inhibitors (Eldepryl, Carbex, Zelapar, Azilect), COMT inhibitors (Comtan, Tasmar), and other medications like Symmetrel and Exelon aim to slow the loss of dopamine or improve just the symptoms of the patient.

Discovery and identification of new compounds or agents as potential therapeutics to arrest fibril and/or aggregate formation, deposition, accumulation and/or persistence of α-synuclein in Parkinson's disease or provide neuroprotection are desperately sought.

Parkinson's disease α-synuclein fibrils and/or aggregates consist of a predominantly 1-pleated sheet structure. Compounds of this invention have been shown to be effective in the inhibition of α-synuclein/NAC fibril formation and/or aggregates as well as in the disruption of pre-formed fibrils and/or aggregates, as shown from Examples provided herein. These compounds could serve as therapeutics for Parkinson's disease and other synucleinopathies.

Tau is a microtubule associated protein found primarily in neuronal axons. Tau hyperphosphorylation is a common characteristic of a number of dementing disorders collectively known as tauopathies, some of which have disctinct tau pathology combined with other brain pathologies. Tauopathies include Alzheimer's disease (AD), Pick's disease (PiD), progressive supranuclear palsy (PSP), corticobasal degeneration (CBD) and familial frontotemporal dementia/Parkinsonism linked to chromosome 17 (FTDP-17), amyotrophic lateral sclerosis/Parkinsonism-dementia complex, argyrophilic grain dementia, dementia pugilistic, diffuse neurofibrillary tangles with calcification, progressive subcortical gliosis and tangle only dementia. (Spillantini, M G and Goedert M, 1998 Trends Neurosci. October 21(10):428-33). In AD, tau pathology is typically limited to the neurons while other tauopathies can pathologically exhibit both neuronal and glial tau deposition (Higuchi, M, et al., 2002. Neuropsychopharmacology: The Fifth Generation of Progress, Chapter 94: Tau protein and tauopathy).

It has recently been postulated that tau protein may link Parkinson's and Alzheimer's disease (Shulman, J. M. and DeJager, P. L. 2009 Nature Genetics 41(12):1261-1262). This study examined whether any genome wide association occurs between the two diseases and found that three genes and two new loci were linked to increased susceptibility.

Physiological phosphorylation of tau regulates the dynamics of the association of tau with tubulin, and thereby microtubule stability (Mazanetz. M. P. and Fischer, P. M. 2007. Nature Reviews 6:464-479). The stabilization of the microtubules in axons ensures that maintain their function for axonal transport, growth and branching (Bulic, B et al., 2009 Angew. Chem. Int. Ed. 48:2-15). Hyperphosphorylation and misfolding of the tau protein is thought to be the causative factor in abnormal intracellular aggregation leading ultimately to neuronal dysfunction. Protein aggregates have been found to be toxic to neurons.

Abnormal intraneuronal tau aggregation has three basic pathological manifestations; neurofibrillary tangles (NFT's), neuropil threads (NT's) and the argyrophilic dystrophic neurite plaques (Braak, H and Braak, E, Neurobio. of Aging. 1997 18(4):351-357). Structurally, the NFT's are principally comprised of paired helical filaments (PHF) comprised of two filamentous tau proteins twisted around one another with a crossover repeat of 80 nm and a width of 8-20 nm (Li, D., et al., 2008. Computational Biology 4(12) and Kidd, M 1963 Nature, 197:192). There are six stages (Braak stages I-VI) of tau deposition in the brain, which progress temporally at defined anatomical locations with the initial stages characterized primarily by the deposition of NFT's and NT's and the secondary stages further accompanied by NP (Braak, 1997). In Alzheimers Disease and other neuropathies, Braak's stages correlate well with clinical disease progression as demonstrated by increasing cognitive dysfunction. Severe cortical destruction which occurs around stages III-IV coincides with the first manifestations of the clinical onset of AD. Although no tau mutations have been identified in AD there is a strong correlation between NFT density and cognitive decline in AD (Brunden, K. R., Trojanowski, J. Q., and Lee, V. M. 2009 Nature Reviews 8:783-93).

New biomarkers and models of their temporal characteristics are becoming even more useful for the diagnosis and characterization of AD (Jack et al., 2010. Lancet 9:119-28). Specifically, tau deposition is associated with neurodegeneration in AD and an increase in CSF tau is an important indicator of tau pathologic changes and correlates well with clinical disease severity. A decrease in FDG-PET correlates well with increased CSF tau and both are valid indicators of synaptic dysfunction (Jack et al, ibid). This model of biomarker ordering, especially in mildly cognitive impaired individuals, has important implications for clinical trials. Potential therapeutics could be more accurately assessed for efficacy is they are able to change the trajectory of cognitive deterioration and individuals might be more selectively chosen for trials (Jack et al, ibid).

It is presently not known if tau is a causative factor in disease but it is likely that either a loss or gain for function results in pathology. In FTLD17, a missense mutation affects the alternative splicing of tau resulting in the disruption of the ratio of the 4R to 3R tau isoform. More of the 4R isoform with an extra repeat of the microtubule binding region may lead to overstabilization of the microtubules resulting in disease. Other post-translational events such as alterations in kinase activity and glycosylation could also cause hyperphosphorylation and result in disease or alternatively proteolytic cleavage could produce truncated tau products more inclined to aggregate (Brunden, ibid).

Recently tau toxicity has been re-emphasized as an important therapeutic target in neurodegerative tauopathies (Keystone Symposium, March 2009). Routes for developing therapeutics are either directed to inhibiting tau-phosphorylation kinases or seeking compounds effective in the modulation of tau aggregation and/or the dissolution or disruption of tau aggregates which may prove equally useful or more specific for the alleviation of tauopathies (Rafii, M and Aisen, P. 2009 BMC Medicine 7:7). A recent paper surveyed the efficacy of several classes of compounds for their ability to prevent tau aggregation and disaggregate pre-formed tau fibrils (Bulic et al.). Although there are general concerns regarding the toxicity of disassembled fibrils, Bulic et al., were able to show that reversing tau aggregation resulted in increased cell viability.

SUMMARY OF INVENTION

In a first aspect, provided herein are compounds such as, but not limited to:

Compound SA-52
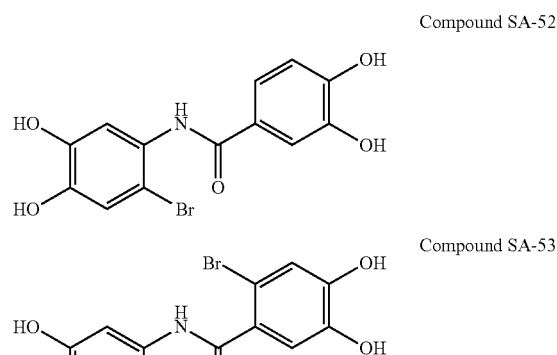
Compound SA-53
Compound SA-54
Compound SA-55
Compound SA-57
Compound SA-58
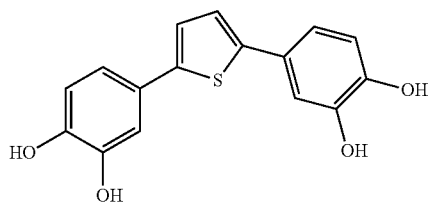
Compound SA-59
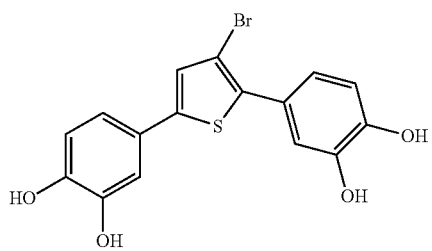
Compound SA-60
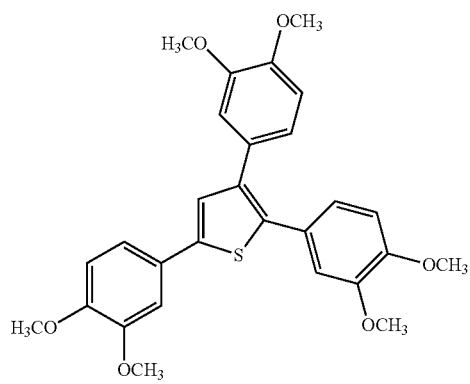
Compound SA-61
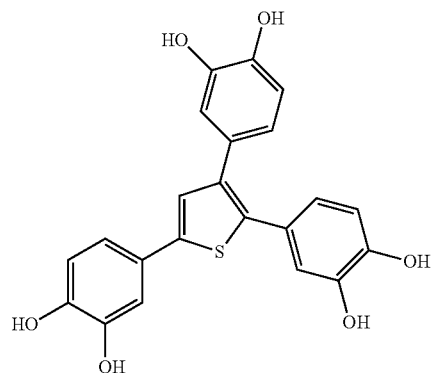
Compound SA-62
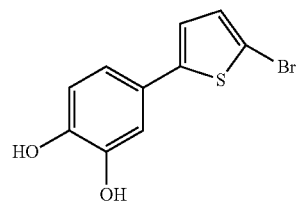
Compound SA-63
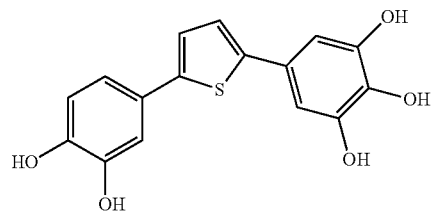
Compound SA-64
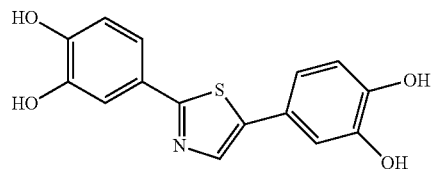

Compound SA-65
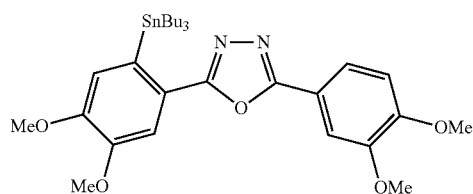
Compound SA-66
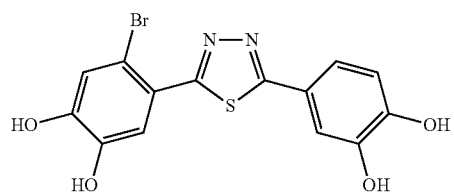
Compound SA-67
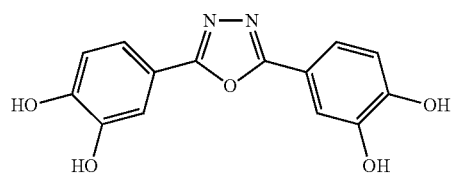
Compound SA-68
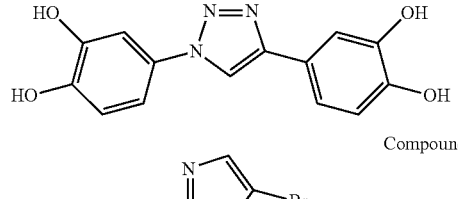
Compound SA-69
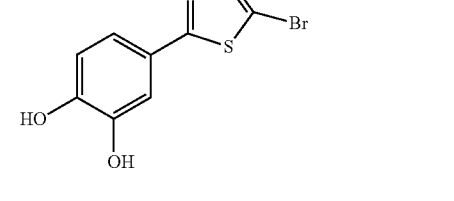
Compound SA-70
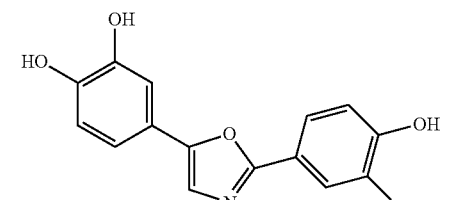
Compound SA-72
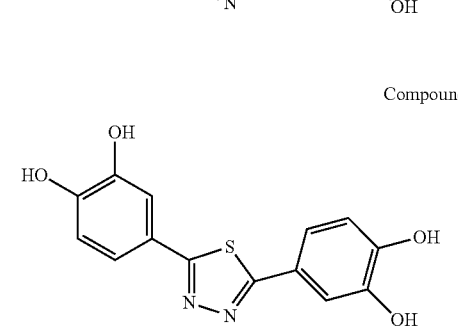
Compound SA-74
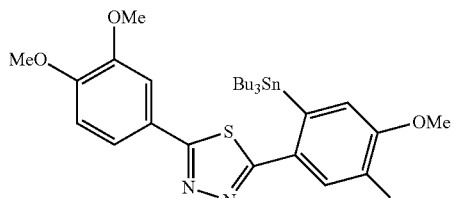
Compound SA-75
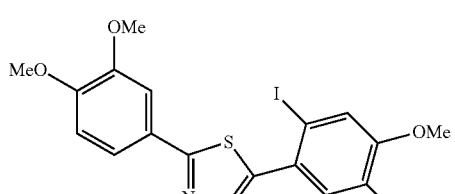
Compound SA-76
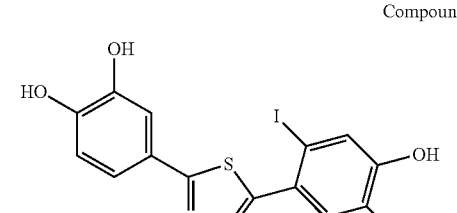
Compound SA-77
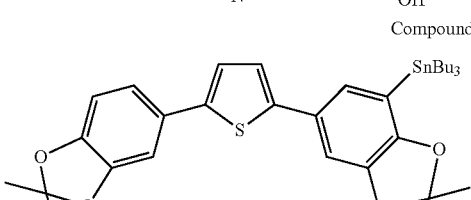
Compound SA-78
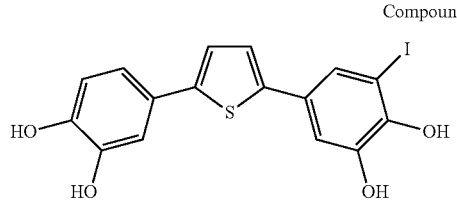
Compound SA-79
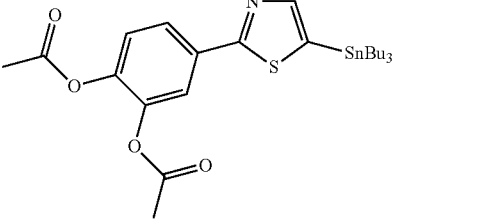
Compound SA-80

Compound SA-81
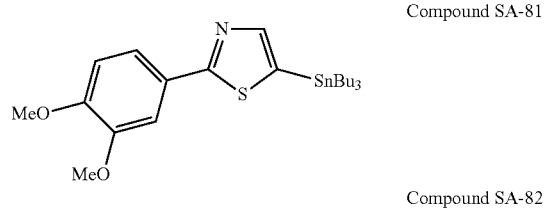
Compound SA-82
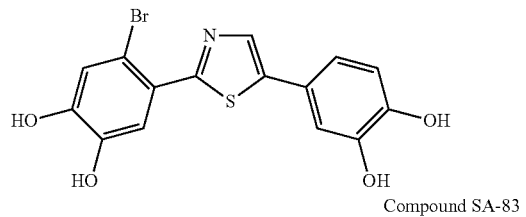
Compound SA-83
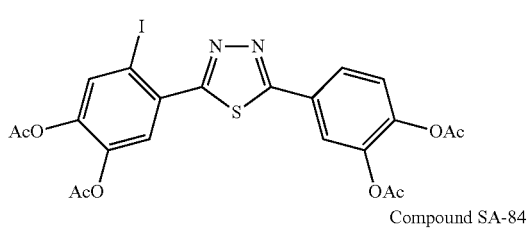
Compound SA-84
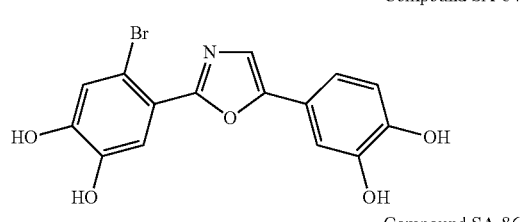
Compound SA-86
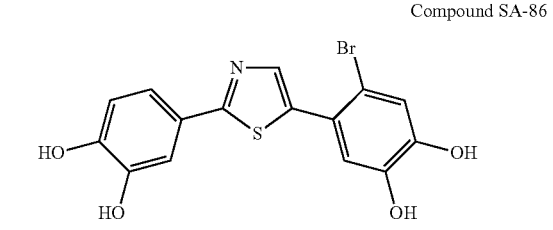
Compound SA-87
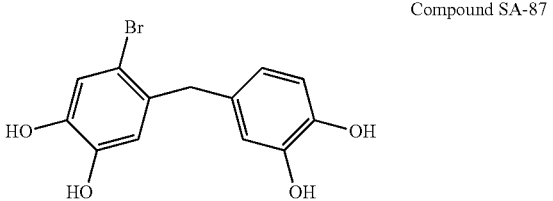
Compound SA-88
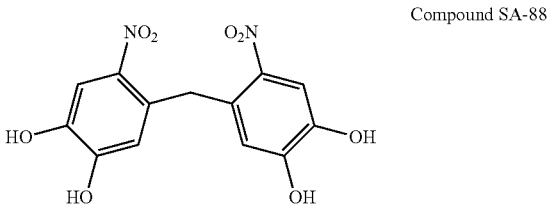
Compound SA-89
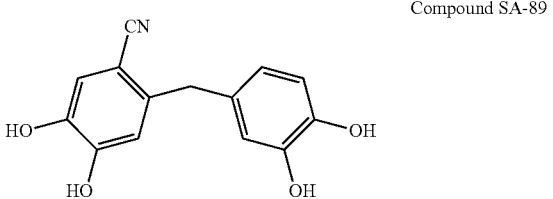
Compound SA-90
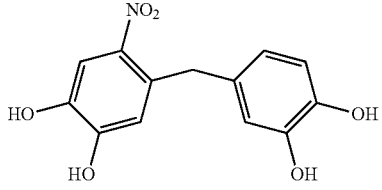
Compound SA-93
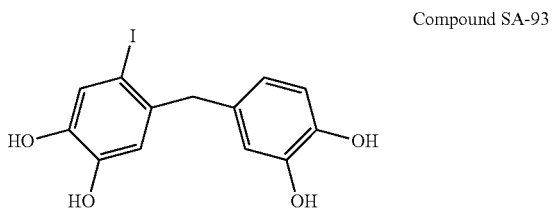
Compound SA-94
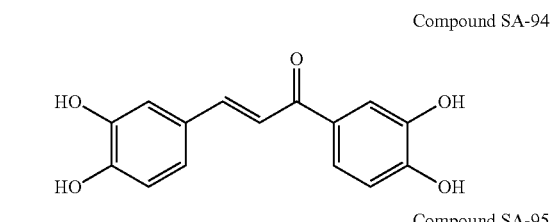
Compound SA-95
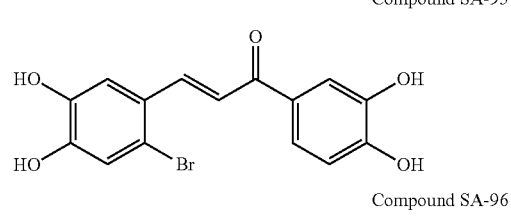
Compound SA-96
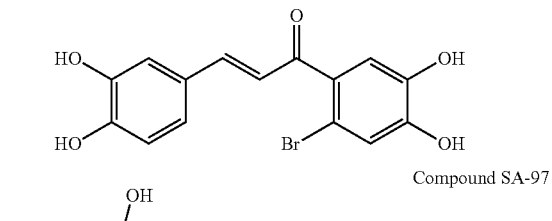
Compound SA-97
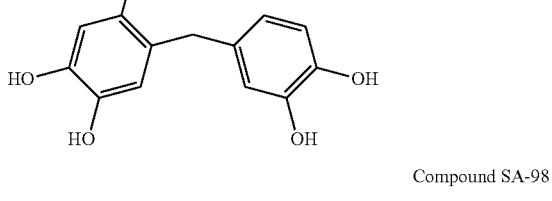
Compound SA-98
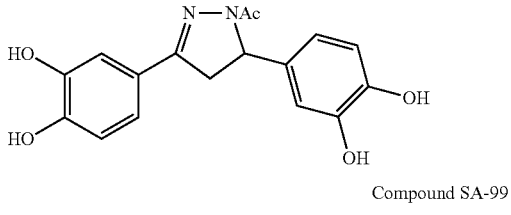
Compound SA-99
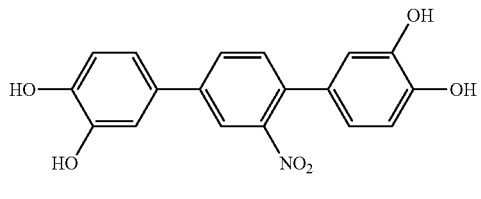

-continued

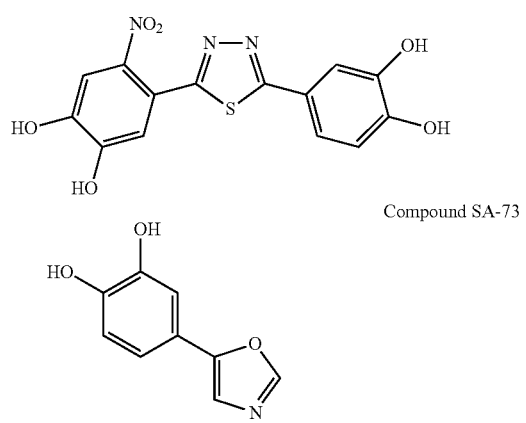

Compound SA-108

Compound SA-73

In a second aspect, this invention is a method of treating a synucleinopathy in a mammal, especially a human, by administration of a therapeutically effective amount of a compound of the first aspect of this invention, for example as a pharmaceutical composition. Methods using such compounds and compositions for disrupting, disaggregating and causing removal, reduction or clearance of α-synuclein fibrils and/or aggregates are provided thereby providing new treatments for synucleinopathies. The treatment of disease may also include the inhibiting the formation of α-synuclein fibrils and/or aggregates or providing neuroprotection for neurons at risk.

Also provided are any pharmaceutically-acceptable derivatives of the compounds of the first aspect of this invention, including salts, esters, enol ethers or esters, acetals, ketals, orthoesters, hemiacetals, hemiketals, solvates, hydrates or prodrugs of the compounds. Pharmaceutically-acceptable salts, include, but are not limited to, amine salts, alkali metal salts, such as but not limited to lithium, potassium and sodium, alkali earth metal salts, such as but not limited to barium, calcium and magnesium, transition metal salts, such as but not limited to zinc and other metal salts, such as but not limited to sodium hydrogen phosphate and disodium phosphate, and also including, but not limited to, salts of mineral acids, such as but not limited to hydrochlorides and sulfates, salts of organic acids, such as but not limited to acetates, lactates, malates, tartrates, citrates, ascorbates, succinates, butyrates, valerates and fumarates.

Pharmaceutical formulations for administration by an appropriate route and means containing effective concentrations of one or more of the compounds provided herein or pharmaceutically acceptable derivatives, such as salts, esters, enol ethers or esters, acetals, ketals, orthoesters, hemiacetals, hemiketals, solvates, hydrates or prodrugs of the compounds that deliver amounts effective for the treatment of synucleinopathies, are also provided.

The formulations are compositions suitable for administration by any desired route and include solutions, suspensions, emulsions, tablets, dispersible tablets, pills, capsules, powders, dry powders for inhalation, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Also provided are methods for treatment, prevention or amelioration of one or more symptoms of synucleinopathies, including but not limited to diseases associated with the formation, deposition, accumulation, or persistence of alpha-synuclein.

Provided are methods for treatment, prevention or amelioration of one or more symptoms of synuclein diseases or synucleinopathies. In one embodiment, the methods inhibit or prevent α-synuclein/NAC fibril formation and/or aggregation, inhibit or prevent α-synuclein/NAC fibril growth, and/or cause disassembly, disruption, and/or disaggregation of preformed α-synuclein/NAC fibrils and α-synuclein/NAC-associated protein deposits and/or aggregates. Synuclein diseases include, but are not limited to Parkinson's disease, PDD, familial Parkinson's disease, Lewy body disease, the Lewy body variant of Alzheimer's disease, dementia with Lewy bodies (DLB), multiple system atrophy, and the Parkinsonism-dementia complex of Guam.

DETAILED DESCRIPTION OF THE INVENTION

A. Definitions

Figure 1:
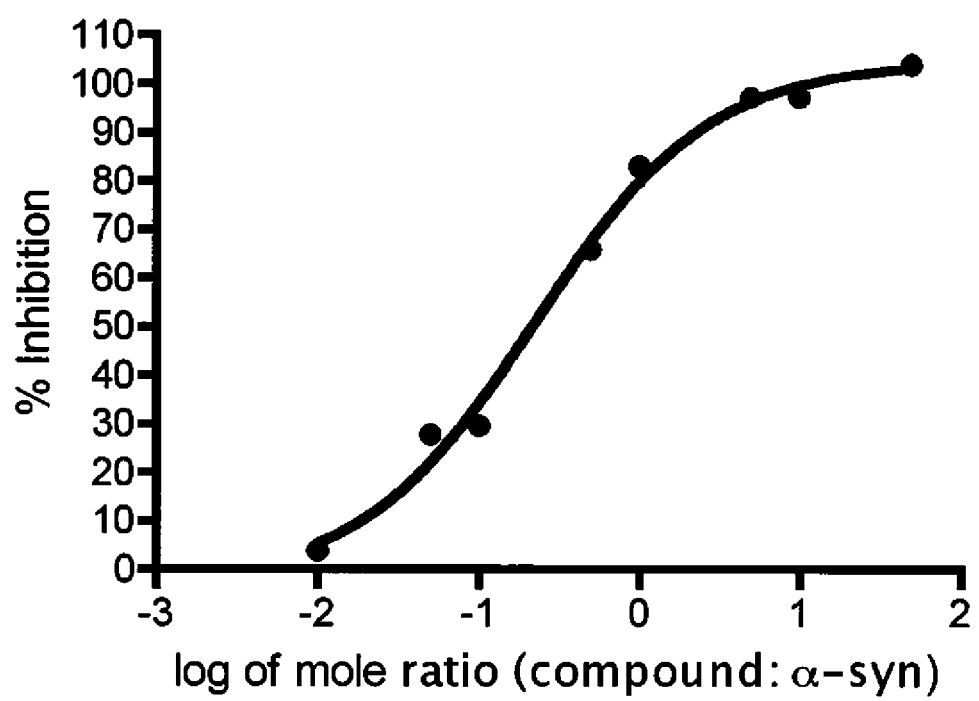
FIG. 1 is a graph illustrating that a compound of the invention causes a dose-dependent inhibition of of α-synuclein aggregation and fibril formation as assessed by Thioflavin T fluorometry.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there is a plurality of definitions for a term herein, those in this section prevail unless stated otherwise.

As used herein, "Synuclein diseases" or "synucleinopathies" are diseases associated with the formation, deposition, accumulation, or persistence of synuclein fibrils, including, but not limited to α-synuclein fibrils. Such diseases include, but are not limited to Parkinson's disease, Familial Parkinson's disease, PDD, Lewy body disease, the Lewy body variant of Alzheimer's disease, dementia with Lewy bodies, multiple system atrophy, and the Parkinsonism-dementia complex of Guam.

Aggregation or Fibrillogenesis refers to the formation, deposition, accumulation and/or persistence of synuclein fibrils, filaments, inclusions, deposits, and/or NAC fibrils, filaments, inclusions, deposits, and/or aggregates or the like.

Inhibition of aggregation or fibrillogenesis refers to the inhibition of formation, deposition, accumulation and/or persistence of such fibrils or fibril-like deposits.

Disruption of fibrils or fibrillogenesis refers to the disruption of pre-formed α-synuclein fibrils, that usually exist in a pre-dominant β-pleated sheet secondary structure. Such disruption by compounds provided herein may involve marked reduction or disassembly of synuclein fibrils as assessed by various methods such as Thioflavin T fluorometry, Congo red binding, SDS-PAGE/Western blotting, as demonstrated by the Examples presented in this application.

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use or for human pharmaceutical use. Such excipients may be solid, liquid, semisolid, or, in the case of an aerosol composition, gaseous.

A "therapeutically effective amount" means the amount that, when administered to a subject or animal for treating a disease, is sufficient to affect the desired degree of treatment, prevention or symptom amelioration for the disease. A "therapeutically effective amount" or a "therapeutically effective dosage" in certain embodiments inhibits, reduces, disrupts, disassembles synuclein fibril formation, deposition, accumulation and/or persistence, or treats, prevents, or ameliorates one or more symptoms of a disease associated with these conditions, such as a synucleinopathy, in a measurable amount in one embodiment, by at least 20%, in other embodiment, by at least 40%, in other embodiment by at least 60%, and in still other embodiment by at least 80%, relative to an untreated subject. Effective amounts of a compound provided herein or composition thereof for treatment of a mammalian subject are about 0.1 to about 1000 mg/Kg of body weight of the subject/day, such as from about 1 to about 100 mg/Kg/day, in other embodiment, from about 10 to about 100 mg/Kg/day. A broad range of disclosed composition dosages are believed to be both safe and effective.

The term "sustained release component" is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically suitable solvents may be formulated for administration by inhalation or insufflation (either through the mouth or the nose) or oral, buccal, parenteral, or rectal administration, as examples.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. For example, slowing or arresting disease development, providing relief from the symptoms or side-effects of the disease, and relieving the disease by causing regression of the disease, such as by disruption of pre-formed synuclein fibrils could all be considered as treatment.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, "NAC" (non-Aβ component) is a 35-amino acid peptide fragment of α-synuclein, which like α-synuclein, has the ability to form fibrils when incubated at 37° C., and is positive with stains such as Congo red (demonstrating a red/green birefringence when viewed under polarized light) and Thioflavin S (demonstrating positive fluorescence) (Hashimoto et al., *Brain Res,* 799:301-306, 1998; Ueda et al., *Proc. Natl. Acad. Sci. U.S.A.* 90:11282-11286, 1993). Inhibition of NAC fibril formation, deposition, accumulation, aggregation, and/or persistence is believed to be effective treatment for a number of diseases involving α-synuclein, such as Parkinson's disease, Lewy body disease and multiple system atrophy.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

Provided herein are compounds and pharmaceutical compositions containing compounds, not limited to those shown above in the summary section and in the following examples.

C. Preparation of the Compounds

The compounds provided herein can be prepared by standard synthetic methods known in the art, and are shown in general schemes provided herein. The examples that follow describe the exemplary embodiments and are not purported to limit the scope of the claimed subject matter. It is intended that the specification, together with the following examples, be considered exemplary only, with the scope and spirit of the claimed subject matter being indicated by the claims that follow these examples. Other embodiments within the scope of claims herein will be apparent to one skilled in the art from consideration of the specification as described herein.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. Other starting materials or early intermediates may be prepared by elaboration of the materials listed above, for example, by methods well known to a person of ordinary skill in the art. The starting materials, intermediates, and compounds provided herein may be isolated and purified using conventional techniques, including precipitation, filtration, distillation, crystallization, chromatography, and the like. The compounds may be characterized using conventional methods, including physical constants and spectroscopic methods.

D. Pharmaceutical Compositions and Administration

The compounds provided herein can be used as such, be administered in the form of pharmaceutically acceptable salts derived from inorganic or organic acids, or used in combination with one or more pharmaceutically acceptable excipients. The phrase "pharmaceutically acceptable salt" means those salts which are, within the scope of sound medical judgment, suitable for use in contact with the tissues without undue toxicity, irritation, allergic response, and the like, and are commensurate with a reasonable benefit/risk ratio. Pharmaceutically acceptable salts are well known in the art. The salts can be prepared either in situ during the final isolation and purification of the compounds provided herein or separately by reacting the acidic or basic drug substance with a suitable base or acid respectively. Typical salts derived from organic or inorganic acids salts include, but are not limited to hydrochloride, hydrobromide, hydroiodide, acetate, adipate, alginate, citrate, aspartate, benzoate, bisulfate, gluconate, fumarate, hydroiodide, lactate, maleate, oxalate, palmitoate, pectinate, succinate, tartrate, phosphate, glutamate, and bicarbonate. Typical salts derived from organic or inorganic bases include, but are not limited to lithium, sodium, potassium, calcium, magnesium, ammonium, monoalkylammonium such as meglumine, dialkylammonium, trialkylammonium, and tetrakylammonium. The mode of administration of the pharmaceutical compositions can be oral, rectal, intravenous, intramuscular, intracisternal, intravaginal, intraperitoneal, bucal, subcutaneous, intrasternal, nasal, or topical. The compositions can also be delivered at the target site through a catheter, an intracoronary stent (a tubular device composed of a fine wire mesh), a biodegradable polymer, or biological carriers including, but are not limited to antibodies, biotin-avidin complexes, and the like. Dosage forms for topical administration of a compound provided herein include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also provided herein.

Actual dosage levels of active ingredients and the mode of administration of the pharmaceutical compositions provided herein can be varied in order to achieve the effective therapeutic response for a particular patient. The phrase "therapeutically effective amount" of the compound provided herein means a sufficient amount of the compound to treat disorders, at a reasonable benefit/risk ratio applicable to any medical treatment. It will be understood, however, that the total daily usage of the compounds and compositions of the provided will be decided by the attending physician within the scope of sound medical judgment. The total daily dose of the compounds provided herein may range from about 0.0001 to about 1000 mg/kg/day. For purposes of oral administration, doses can be in the range from about 0.001 to about 50 mg/kg/day. If desired, the effective daily dose can be divided into multiple doses for purposes of administration; consequently, single dose compositions may contain such amounts or submultiples thereof to make up the daily dose. The specific therapeutically effective dose level for any particular patient will depend upon a variety of factors including the disorder being treated and the severity of the disorder; medical history of the patient, activity of the specific compound employed; the specific composition employed, age, body weight, general health, sex and diet of the patient, the time of administration, route of administration, the duration of the treatment, rate of excretion of the specific compound employed, drugs used in combination or coincidental with the specific compound employed; and the like.

The compounds provided can be formulated together with one or more non-toxic pharmaceutically acceptable diluents, carriers, adjuvants, and antibacterial and antifungal agents such as parabens, chlorobutanol, phenol, sorbic acid, and the like. Proper fluidity can be maintained, for example, by the use of coating materials such as lecithin, by the maintenance of the required particle size in the case of dispersions, and by the use of surfactants. In some cases, in order to prolong the effect of the drug, it is desirable to decrease the rate of absorption of the drug from subcutaneous or intramuscular injection. This can be accomplished by suspending crystalline or amorphous drug substance in a vehicle having poor water solubility such as oils. The rate of absorption of the drug then depends upon its rate of dissolution, which, in turn, may depend upon crystal size and crystalline form. Prolonged absorption of an injectable pharmaceutical form can be achieved by the use of absorption delaying agents such as aluminum monostearate or gelatin.

The compound provided herein can be administered enterally or parenterally in solid or liquid forms. Compositions suitable for parenteral injection may comprise physiologically acceptable, isotonic sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances.

The compounds provided herein can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

Injectable dosage forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds provided herein may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, preservative and flavoring and coloring agent.

In one embodiment, the compounds are formulated in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of a disease associated with α-synuclein/NAC fibril formation such as Parkinson's disease. Compositions for rectal or vaginal administration are preferably suppositories which can be prepared by mixing the compounds provided herein with suitable non-irritating excipients or carriers such as cocoa butter, polyethylene glycol or a suppository wax which are solid at room temperature but liquid at body temperature and therefore melt in the rectum or vaginal cavity and release the active compound.

Compounds provided herein can also be administered in the form of liposomes. Methods to form liposomes are known in the art (Prescott, Ed., *Methods in Cell Biology* 1976, Volume XIV, Academic Press, New York, N.Y.) As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound provided herein, stabilizers, preservatives, excipients and the like. The preferred lipids are natural and synthetic phospholipids and phosphatidyl cholines (lecithins).

The compounds provided herein can also be administered in the form of a 'prodrug' wherein the active pharmaceutical ingredients are released in vivo upon contact with hydrolytic enzymes such as esterases and phophatases in the body. The term "pharmaceutically acceptable prodrugs" as used herein represents those prodrugs of the compounds provided herein, which are, within the scope of sound medical judgment, suitable for use in contact with the tissues without undue toxicity, irritation, allergic response, and the like, commensurate with a reasonable benefit/risk ratio, and effective for their intended use. A thorough discussion is provided in T. Higuchi and V. Stella (Higuchi, T. and Stella, V. Pro-drugs as Novel Delivery Systems, V. 14 of the A.C.S. Symposium Series; Edward B. Roche, Ed., *Bioreversible Carriers in Drug Design* 1987, American Pharmaceutical Association and Pergamon Press), which is incorporated herein by reference.

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers.

These may be prepared according to methods known to those skilled in the art. For example, liposome formulations may be prepared as described in U.S. Pat. No. 4,522,811. Briefly, liposomes such as multilamellar vesicles (MLVs) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Sustained Release Formulations

Also provided are sustained release formulations to deliver the compounds to the desired target (i.e. brain) at high circulating levels (between $10^{-9}$ and $10^{-4}$ M). In a certain embodiment for the treatment of Parkinson's disease, the circulating levels of the compounds are maintained up to $10^{-7}$ M. The levels are either circulating in the patient systemically, or in one embodiment, present in brain tissue, and in other embodiments, localized to the α-synuclein fibril deposits in brain.

It is understood that the compound levels are maintained over a certain period of time as is desired and can be easily determined by one skilled in the art. In one embodiment, the administration of a sustained release formulation is effected so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

Article of Manufacture

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of synuclein diseases, within the packaging material, and a label that indicates that the compound or composition, or pharmaceutically acceptable derivative thereof, is used for treatment, prevention or amelioration of one or more symptoms of synuclein diseases. The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for synuclein diseases.

E. Evaluation of the Activity of the Compounds

The biological activity of the compounds provided herein as disruptors/inhibitors of Parkinson's disease α-synuclein fibrils was assessed by determining the efficacy of the compounds to cause a disassembly/disruption of pre-formed Parkinson's disease α-synuclein fibrils. In one study, Thioflavin T fluorometry was used to determine the effects of the compounds, and of anegative control reference compound). In this assay Thioflavin T binds specifically to fibrillar protein, and this binding produces a fluorescence enhancement at 485 nm that is directly proportional to the amount of fibrils present. The higher the fluorescence, the greater the amount of fibrils present (Naki et al, *Lab. Invest.* 65:104-110, 1991; Levine III, *Protein Sci.* 2:404-410, 1993; Amyloid: Int. *J. Exp. Clin. Invest.* 2:1-6, 1995).

In the Congo red binding assay the ability of a given test compound to alter α-synuclein fibril binding to Congo red was quantified. In this assay, α-synuclein fibrils and test compounds were incubated for 2 days and then vacuum filtered through a 0.2 µM filter. The amount of α-synuclein fibrils retained in the filter was then quantitated following staining of the filter with Congo red. After appropriate washing of the filter, any lowering of the Congo red color on the filter in the presence of the test compound (compared to the Congo red staining of the protein in the absence of the test compound) was indicative of the test compound's ability to diminish/alter the amount of aggregated and congophilic α-synuclein fibrils.

F. Combination therapy

In another embodiment, the compounds may be administered in combination, or sequentially, with another therapeutic agent. Such other therapeutic agents include those known for treatment, prevention, or amelioration of one or more symptoms of synuclein diseases. Such therapeutic agents include, but are not limited to; carbidopa/levodopa (Sinemet, Stalevo, Parcopa), dopamine agonists (Apokyn, Parlodel, Neupro, Mirapex, Requip), anticholinergics (Cogentin, Artane), MAO-B inhibitors (Eldepryl, Carbex, Zelapar, Azilect), COMT inhibitors (Comtan, Tamar), and other medications like Symmetrel and Exelon.

G. Methods of Use of the Compounds and Compositions

The compounds and compositions provided herein are useful in methods of treatment, prevention, or amelioration of one or more symptoms of synucleopathies, including but not limited to diseases associated with the formation, deposition, accumulation, or persistence of synuclein fibrils. Also provided are methods to inhibit or prevent α-synuclein/NAC fibril formation and/or aggregation, methods to inhibit or prevent α-synuclein/NAC fibril growth, and methods to cause disassembly, disruption, and/or disaggregation of preformed α-synuclein/NAC fibrils and α-synuclein/NAC-associated protein deposits.

In certain embodiments, the synuclein diseases or synucleinopathies treated, prevented or whose symptoms are ameliorated by the compounds and compositions provided herein include, but are not limited to diseases associated with the formation, deposition, accumulation, or persistence of synuclein fibrils, including α-synuclein fibrils and/or aggregates. In certain embodiments, such diseases include Parkinson's disease, PDD, familial Parkinson's disease, Lewy body disease, the Lewy body variant of Alzheimer's disease, dementia with Lewy bodies, multiple system atrophy, and the Parkinsonism-dementia complex of Guam.

The following non-limiting Examples are given by way of illustration only and are not considered a limitation of the subject matter, many apparent variations of which are possible without departing from the spirit or scope thereof.

EXAMPLES

Example 1

Synthesis of SA-52

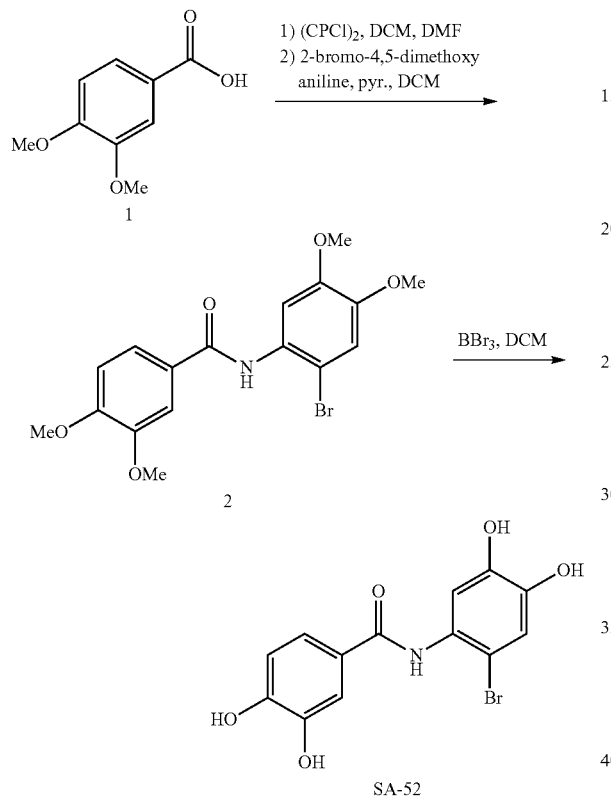

3,4-dimethoxybenzoic acid (1) (1.00 g, 5.5 mmol) was slurried in 5 mL of DCM. Oxalyl chloride (0.9 mL, 10.5 mmol) was then added, and five drops of DMF were added to initiate the reaction. The mixture was stirred overnight during which time it became a yellow solution. The solution was concentrated and dried in vacuo to remove the solvent and oxalyl chloride. The resultant solid was redissolved in 7 mL of DCM, cooled to −78° C., and 1.5 mL of pyridine was added. Then, 0.696 g of 2-bromo-4,5-dimethoxy aniline (3 mmol) was added in 5 mL of DCM. A solid formed causing stirring to be difficult, and therefore, an additional 6 mL portion of DCM was added. The mixture was warmed to 23° C., and after the reaction was complete, quenched with 20 mL of water. The layers were separated, the organic was washed with 20 mL of brine, dried with $Na_2SO_4$, and concentrated. The crude product was purified by column chromatography and then PTLC (0.5% MeOH in DCM as eluent) to give 1.05 g (88% yield) of benzamide (2) as an off-white solid. NMR (200 MHz, $CDCl_3$) δ 8.25 (bs, 2H, overlapping peak), 7.57 (d, J=2 Hz, 1H), 7.48 (dd, J=2 Hz, 8.4 Hz, 1H), 7.06 (s, 1H), 6.98 (d, J=8.4 Hz, 1H), 4.09-3.99 (3 overlapping singlets, 9H), 3.90 (s, 3H).

To 0.049 g (0.14 mmol) of 2 in 3 mL of DCM was added 2.5 mL 1 M $BBr_3$ in DCM. The solution was stirred 18 h. The mixture was quenched with 10 mL MeOH and concentrated. The concentrate was diluted again with 5 mL of MeOH, and 20 mL of MeOH was added. The resultant solid was filtered, collected, and dried under vacuum overnight to give 0.012 g (29% yield) of SA-52 as a brown solid. $^1$H NMR (200 MHz, $CDCl_3$) 6 HRMS calculated for $C_{13}H_{11}BrNO_5$ $(M+H)^+$ 339.9821. found 339.9828.

Example 2

Synthesis of SA-53

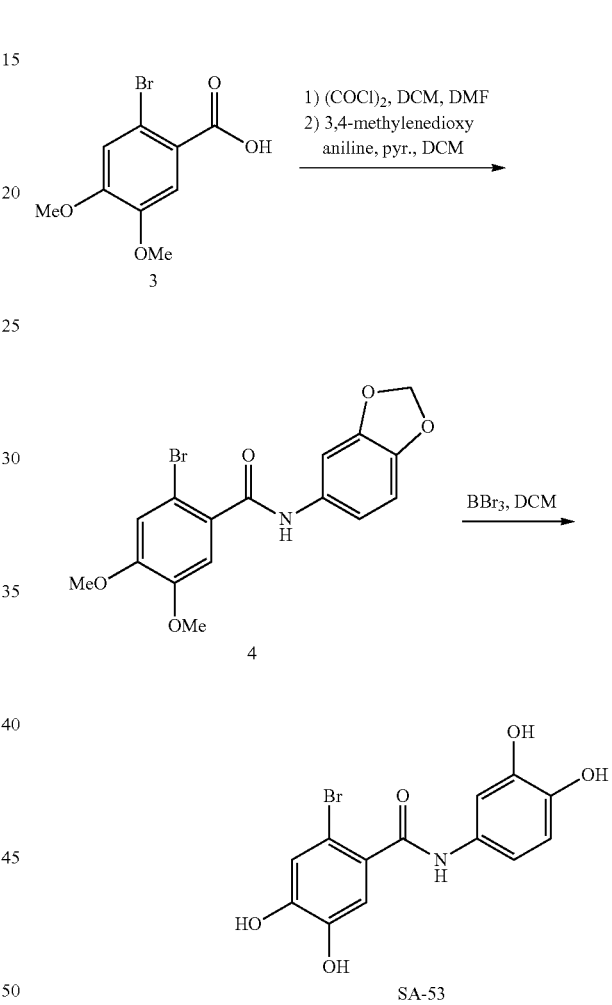

To 0.401 g (1.5 mmol) of 2-bromo-4,5-dimethoxybenzoic acid (3) in 4 mL of DCM was added 0.4 mL (4.7 mmol) of oxalyl chloride, and 1 drop of DMF. The mixture was stirred for 7 h, concentrated, dried in vacuo in a similar manner to compound 2, and diluted with 5 mL of DCM. This solution was cooled to −78° C., treated with 0.8 mL pyridine and 0.137 (1 mmol) 3,4-methylenedioxy aniline. The mixture was then brought to 23° C., stirred 16 h, quenched with 10 mL of water, and the resultant layers separated. The organic layer was washed twice with 10 mL of water, dried with $Na_2SO_4$, and concentrated. The crude product was purified by PTLC using 10% EtOAc in DCM as the eluent to give 0.310 g (82% yield) of benzamide 4 as a brown solid. NMR (200 MHz, $CDCl_3$) δ 7.90 (bs, 1H), 7.40 (bs, 1H), 7.27 (d, J=2.6 Hz, 1H), 7.15 (s, 1H), 6.96 (d, J=8.6 Hz, 1H), 6.81 (d, J=8.6 Hz, 1H), 6.00 (s, 2H), 3.93 (s, 6H), HRMS calculated for $C_{16}H_{15}BrNO_5$ (M+H)$^+$ 380.0134. found 380.0145.

Example 3

Synthesis of SA-54

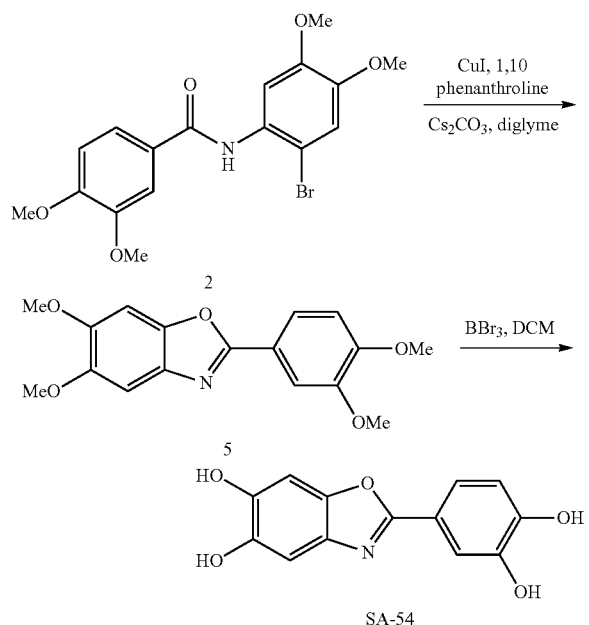

To 0.230 g (0.58 mmol) of benzamide 2 was added 0.017 g of CuI (0.09 mmol), 0.031 g (0.17 mmol) of 1,10 phenanthroline, and 0.560 g (1.7 mmol) of $Cs_2CO_3$. The mixture was suspended in 5 mL of diglyme, and heated to 140° C. for 20 h. The mixture was diluted with 30 mL DCM, washed three times with 20 mL of water, dried ($Na_2SO_4$), and concentrated to give an orange oil as the crude product. This was heated under vacuum (1 mm Hg) until a light orange solid formed to give 0.135 g (75% yield) of benzoxazole 5, which was used without further purification. NMR (200 MHz, $CDCl_3$) δ 7.74 (dd, J=2.0 Hz, 8.4 Hz, 1H), 7.67 (d, J=2.2 Hz, 1H), 7.21 (s, 3H), 7.10 (s, 3H), 6.95 (d, J=8.4 Hz, 1H), 3.98-3.89 (4 overlapping singlets, 12H).

To 0.071 g (0.23 mmol) of 5 in 5 mL of DCM at 0° C. was added 2 mL 1M $BBr_3$ in DCM. The dark brown mixture was stirred 6 h, quenched with 5 mL MeOH, and concentrated. The MeOH dilution-concentration procedure was repeated three more times to give 0.081 g of crude product. This product was purified by PTLC using 5% MeOH/DCM followed by 10% MeOH/DCM as the eluent and gave 0.023 g (39% yield) of SA-54 as an off-white solid. $^1$H NMR (200 MHz) δ 8.84 (bs, 2H), 8.34 (bs, 1H), 7.35 (bs, 1H), 7.47 (d, J=2 Hz, 1H), 7.40 (dd, J=2 Hz, 8.2 Hz, 1H), 7.05 (s, 2H), 7.01 (s, 2H). HRMS Calculated for $C_{13}H_{10}NO_5$ (M+H)$^+$ 260.0586. found 260.0559.

Example 4

Synthesis of SA-55

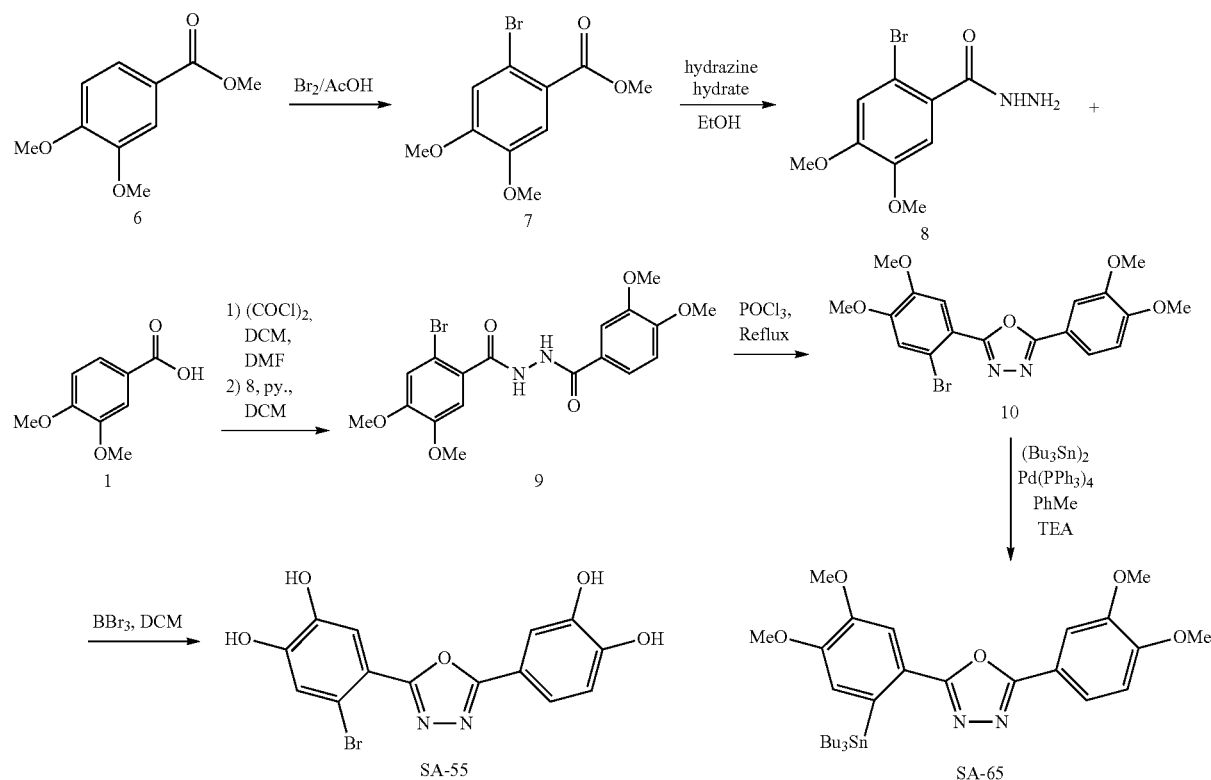

To 10.00 g (51 mmol) of methyl 3,4 dimethoxybenzoate (6) in 50 mL of AcOH at 0° C. was added 8.90 g (56 mmol) of $Br_2$ in 50 mL of AcOH over 1.5 h. The ice bath was removed and the mixture stirred 45 min. The reaction was quenched by pouring into 700 mL of $H_2O$, stirred 30 min, left quiescent for 1 h, and filtered. The collected solid was washed with $H_2O$ and washed with sat. aq. $Na_2S_2O_3$. The solid was partially dried, dissolved in 300 mL hot MeOH, and the resultant solution was cooled. The cool methanolic solution of product was treated with 200 mL of $H_2O$ and the white solid filtered to give 8.92 g (64% yield) of methyl-2-bromo-4,5-dimethoxybenzoate (7) as a white powder. The compound matched the physical and spectral properties of the known compound.

A mixture of 0.960 g (3.48 mmol) of 7, 1.60 g (35 mmol) of hydrazine hydrate (62% hydrazine), and 5 mL of EtOH was refluxed for 15 h. The mixture was cooled to −20° C., vacuum filtered, washed with 50 mL of ice-cold 1:1 EtOH:$H_2O$, and dried to give 0.832 g (87% yield) of (2-bromo-4,5-dimethoxy benzoyloxy) hydrazine (8) as a white, needle-like crystalline solid. The above procedure was repeated on 2.79 g of the starting ester 7 to result in 2.77 g (99% yield) of 8. $^1$H NMR (200 MHz, $CDCl_3$) δ 6.97 (s, 1H), 6.86 (s, 1H), 3.85 (s, 6H). HRMS Calculated for $C_9H_{12}O_3N_2Br$ 275.0031. found 275.0037.

To 2.15 g (11.8 mmol) of 3,4-dimethoxybenzoic acid (1) in 10 mL of DCM was added sequentially 2.5 mL (29.1 mmol) oxalyl chloride and 0.2 mL of DMF. The mixture was stirred for 16 h during which time it became a clear, light yellow solution. This solution was concentrated and dried thoroughly to remove the excess oxalyl chloride to generate the crude acid chloride as a light yellow solid. This solid was taken up in 20 mL of DCM, the solution cooled to 0° C., and treated with 10 mL of pyridine and 0.25 g of DMAP. The resultant solution was treated with 1.69 g (6.15 mmol) of 8 in 10 mL DCM and 10 mL of pyridine. The mixture was stirred 3 h at 0° C. and warmed to 23° C. The reaction was stirred an additional 16 h, concentrated, taken up in 50 mL of EtOAc, and the layers separated. The aqueous was extracted once more with 50 mL EtOAc. The combined organic layers were washed three times with 100 mL $H_2O$, dried ($Na_2SO_4$), and concentrated. The concentrate was purified by Flash 40+M column chromatography (Biotage) eluting first with 150 mL of 1:1 EtOAc/Hex and then 2 L 5:1 EtOAc/Hex to give 1.27 g (47% yield) of hydrazide 9 as a yellow-brown powder. The reaction was repeated using 2.20 g of 3,4 dihydroxybenzoic acid (1) and 2.77 g of hydrazine 8 to give 2.60 g (49% yield) of hydrazide 9. $^1$H NMR (200 MHz, $CDCl_3$) δ 9.91 (d, J=5.2 Hz, 1H), 9.53 (d, J=5.0 Hz, 1H), 7.46 (dd, J=2.0 Hz, 8.4 Hz, 1H), 7.41 (d, J=2.2 Hz, 1H), 7.23 (s, 1H), 6.98 (s, 1H), 6.80 (d, J 8.4 Hz, 1H), 3.96-3.89 (4 overlapping singlets, 12H).

A solution of 0.352 g of intermediate 9 in 3 mL of $POCl_3$ was refluxed for 3 h. The reaction mixture is cooled, poured into 125 mL of water, and sonicated for one minute. The suspension was allowed to stand for 1 h, and the solid was filtered, washed with excess water, collected, and air-dried to give 0.302 g (90% yield) of brominated tetramethoxyoxadiazole (10) as a white solid. $^1$H NMR (200 MHz, $CDCl_3$) δ 7.71 (dd, J 2.0 Hz, 8.4 Hz, 1H), 7.67 (d, J=2.0 Hz, 1H), 7.57 (s, 1H), 7.17 (s, 1H), 6.98 (d, J=8.2 Hz, 1H), 3.96 (4 overlapping singlets, 12H). HRMS Calculated for $C_{14}H_{10}BrN_2O_5$ $(M+H)^+$ 421.0339. found 421.0334.

A mixture of 0.038 g of intermediate 10 in 3 mL of DCM was cooled to −78° C., and treated dropwise with a solution of 0.450 g of $BBr_3$ in 5 mL of DCM. The mixture was stirred at −78° C. for 1 h, then at 23° C. for 2.5 h. The mixture was quenched by adding it carefully to 5 mL of MeOH in a 100 mL flask. The methanol solution was concentrated to 1 mL, diluted with 5 mL water, and filtered to give 0.017 g (56% yield) of SA-55 as a light yellow solid. $^1$H NMR (200 MHz, $CDCl_3$) δ 10.5-9.5 (overlapping broad singlets, 4H), 7.56 (d, J=2 Hz, 1H), 7.52 (s, 1H), 7.48 (dd, J=2 Hz, 8.6 Hz, 1H), 7.25 (s, 1H), 7.04 (d, J=8.4 Hz, 1H)

Example 5

Synthesis of SA-57

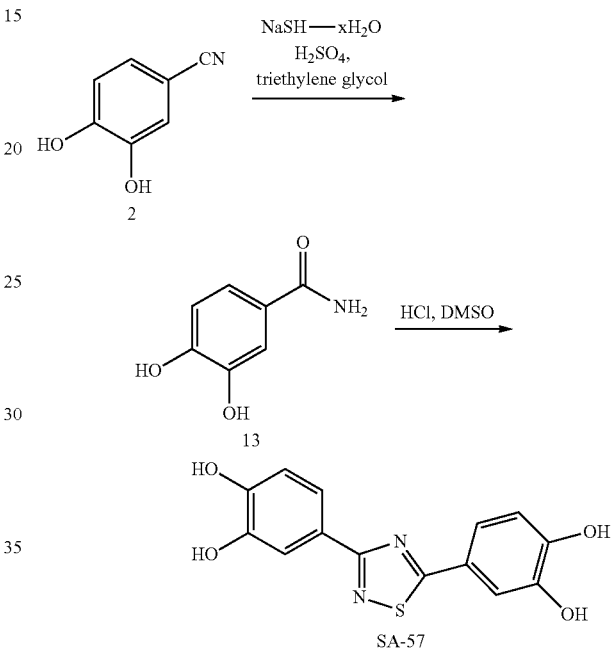

To a thick-walled 15 mL tube with a resealable Teflon screw-cap was added 0.584 g (4.32 mmol) of 3,4-dihydroxybenzonitrile (12), 5 mL of triethylene glycol, 1.172 g of $NaSH.xH_2O$, and 0.25 mL of concentrated $H_2SO_4$. The tube was sealed with the cap, and the mixture was warmed to 110° C. and stirred for 3 days at this temperature. The reaction was quenched by pouring into 100 mL sat. aq. $NH_4^+Cl$, and extracted twice with 50 mL of EtOAc. The combined organics were washed three times with 15 mL water, dried with $NaSO_4$, and concentrated to give 0.512 g (71% yield) of 13 as a golden colored solid. $^1$H NMR (200 MHz, $CDCl_3$) δ 9.67 (s, 1H), 9.29 (s, 1H), 7.56 (dd, J 1.8 Hz, 8.2 Hz), 7.49 (d, J=1.8 Hz), 6.94 (d, J=8.2 Hz), 6.09 (s, 2H). $^{13}$C NMR (50 MHz, $CDCl_3$) δ 198.9, 150.5, 147.4, 133.7, 123.3, 108.2, 107.8, 102.3.

A solution of 0.40 g (2.37 mmol) of 13 in 7 mL of DMSO was treated with 12 drops of concentrated HCl, warmed to 38° C. for 18 h, and poured into 25 mL of brine. The resultant solid was filtered and washed with water to give 0.21 g (59% yield) of SA-57 as a yellow solid. $^1$H-NMR (DMSO-d6) 9.85 (bs, 1H) 9.52 (bs, 1H), 9.43 (bs, 1H), 9.28 (bs, 1H), 7.69 (d, 1H, J=2 Hz), 7.59 (dd, 1H, J=2.2, 8.2 Hz), 7.46 (d, 1H, J=2 Hz), 7.38 (dd, 1H, J=2.2, 8.2 Hz), 6.90 (d, 1H, J=8.2 Hz), 6.86 (d, 1H, J=8.4 Hz). $^{13}$C-NMR (DMSO-d6) 187.8, 173.4, 150.2, 148.5, 146.4, 145.9, 124.6, 122.0, 120.4, 120.2, 116.8, 116.2, 115.7, 114.5. HRMS-ESI Calculated for $C_{14}H_{11}N_2O_4S$ (M+H)$^+$303.0440. found 303.0448.

Example 6

Synthesis of SA-58

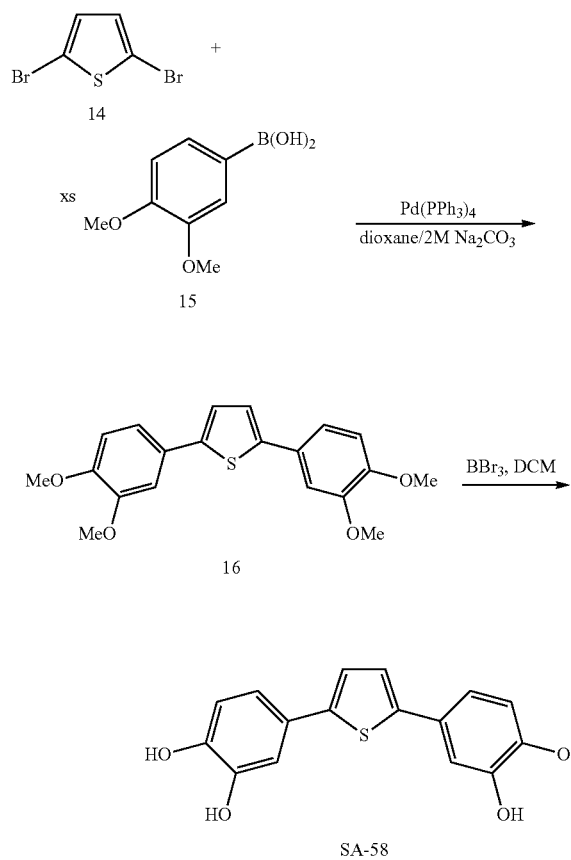

To a solution of 2,5-dibromothiophene (14) (242 mg, 1 mmol), (3,4-dimethoxy phenyl)boronic acid (15) (455 mg, 2.5 mmol), and Pd(PPh$_3$)$_4$ (58 mg, 0.05 mmol) in dioxane (10 mL) was added Na$_2$CO$_3$ (12 mL, 2.0 M aqueous solution). The resultant mixture was purged with nitrogen and stirred rapidly while heating at 90° C. overnight. The reaction mixture was cooled to 23° C., acidified with 1M HCl and extracted with EtOAc. The combined organic extracts were washed with H$_2$O, dried over MgSO$_4$, filtered and concentrated under reduced pressure. 2,5-bis(3',4'-dimethoxyphenyl)thiophene (16) was obtained quantitatively as a green-yellow solid after the purification by column chromatography (10%-20% EtOAc in hexanes).

To a solution of 2,5-bis(3',4'-dimethoxyphenyl)thiophene 16 (110 mg, 0.3 mmol) in dry dichloromethane at −78° C. was added BBr$_3$ (3 mL, 1M solution in DCM, 2.5 equiv per methoxy function) dropwise. The reaction mixture was stirred at −78° C. for 3 h, warmed to 23° C., and stirred 16 h under nitrogen atmosphere. Water (10 mL) was added to quench the reaction, and the aqueous layer was extracted with EtOAc. The combined organic layer was washed with brine, dried over MgSO$_4$, filtered, and concentrated under reduced pressure. The product was purified by recrystallization in MeOH/DCM and SA-58 was obtained quantitatively as a greenish solid.

Example 7

Synthesis of SA-59, SA-60 and SA-61

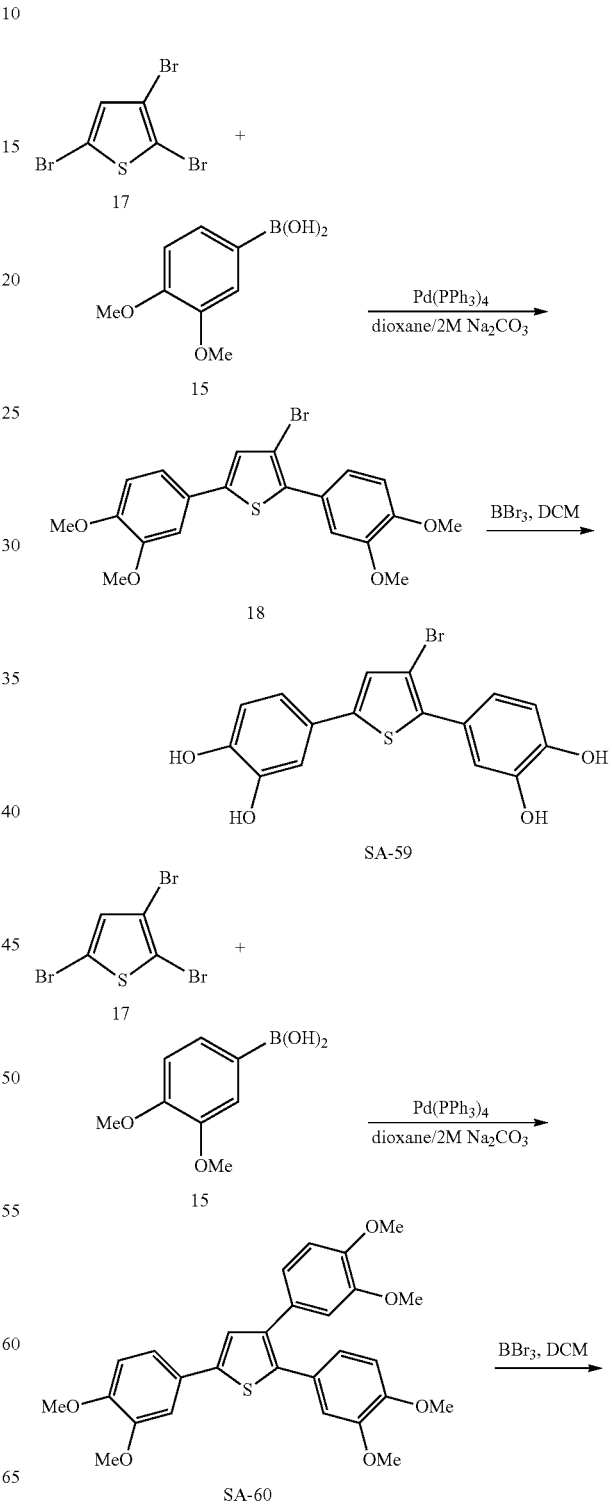

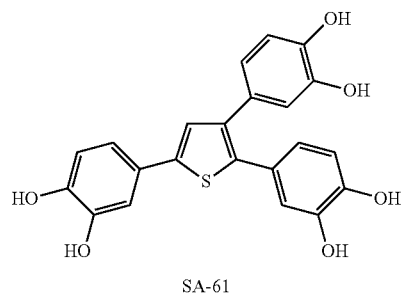 [SMILES: Oc1ccc(-c2cc(-c3ccc(O)c(O)c3)c(-c3ccc(O)c(O)c3)s2)cc1O]

SA-61

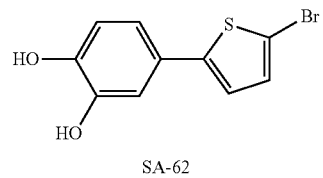

SA-62

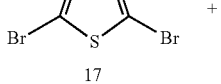

17

3-bromo-2,5-bis(3',4'-dimethoxyphenyl)thiophene (18) was prepared by the reaction of 2,3,5-tribromothiophene (17) (321 mg, 1 mmol) and (3,4-dimethoxyphenyl)boronic acid (15) (419 mg, 2.3 mmol) according to the similar procedure for compound 16. The reaction mixture was purified by column chromatography (10%-30% EtOAc in hexanes) and afforded 18 (337 mg, 77% yield) as a yellow solid. SA-60 was also isolated (97 mg, 20% yield) from the reaction above as a dark yellow solid.

SA-59 was prepared by the reaction of 3-bromo-2,5-bis(3', 4'-dimethoxyphenyl)thiophene (18) (258 mg, 0.59 mmol) and BBr$_3$ (6 mL, 6 mmol) according to the similar procedure for compound SA-58. SA-59 (157 mg, 70% yield) was obtained after preparative thin layer chromatography (PTLC) purification (10% MeOH in DCM) as a green solid.

SA-61 was prepared by the reaction of 2,3,5-tri(3',4'-dimethoxyphenyl)thiophene (SA-60) (68 mg, 0.14 mmol) and BBr$_3$ (2 mL, 2 mmol) according to the similar procedure for compound SA-58. SA-61 (34 mg, 60% yield) was obtained after PTLC purification (10% MeOH in DCM) as a brown oil.

Example 8

Synthesis of SA-62

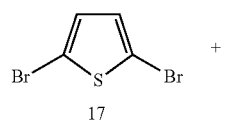

17

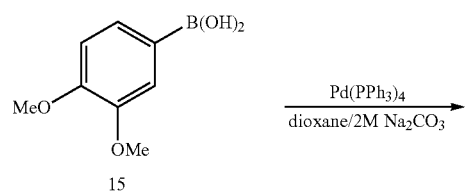

15

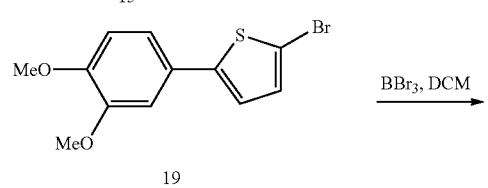

19

Compound 19 was prepared by the reaction of 2,5-dibromothiophene (17) (1.14 g, 5.24 mmol) and (3,4-dimethoxyphenyl) boronic acid (15) (910 mg, 5 mmol) according to the similar procedure for compound 16. The reaction mixture was purified by flash column chromatography (FCC) (5%-20% EtOAc in hexanes) and afforded compound 19 (509 mg, 34% yield) as a yellowish crystal. Compound 16 was also isolated (578 mg, 65% yield) as a yellow solid.

SA-62 was prepared by the reaction of 2-bromo-5-(3,4-dimethoxyphenyl)thiophene (19) (60 mg, 0.2 mmol) and BBr$_3$ (1M in DCM, 1 mL, 1 mmol) according to the similar procedure for compound SA-52 and isolated as a green solid in quantitative yield.

Example 9

Synthesis of SA-63

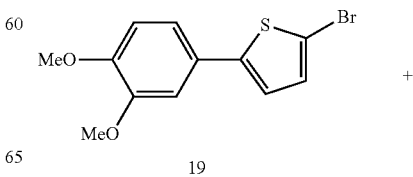

19

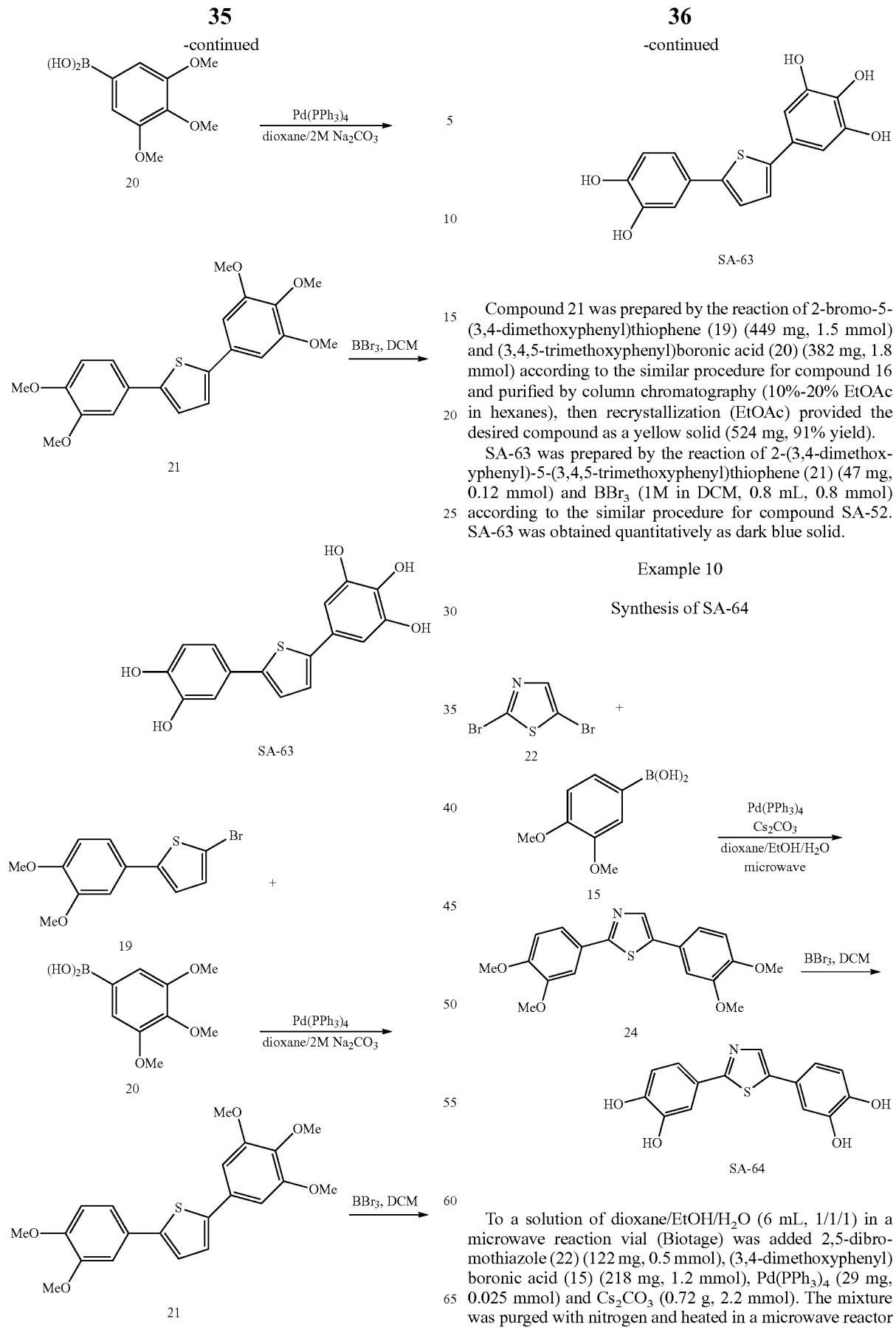

Compound 21 was prepared by the reaction of 2-bromo-5-(3,4-dimethoxyphenyl)thiophene (19) (449 mg, 1.5 mmol) and (3,4,5-trimethoxyphenyl)boronic acid (20) (382 mg, 1.8 mmol) according to the similar procedure for compound 16 and purified by column chromatography (10%-20% EtOAc in hexanes), then recrystallization (EtOAc) provided the desired compound as a yellow solid (524 mg, 91% yield).

SA-63 was prepared by the reaction of 2-(3,4-dimethoxyphenyl)-5-(3,4,5-trimethoxyphenyl)thiophene (21) (47 mg, 0.12 mmol) and BBr$_3$ (1M in DCM, 0.8 mL, 0.8 mmol) according to the similar procedure for compound SA-52. SA-63 was obtained quantitatively as dark blue solid.

Example 10

Synthesis of SA-64

To a solution of dioxane/EtOH/H$_2$O (6 mL, 1/1/1) in a microwave reaction vial (Biotage) was added 2,5-dibromothiazole (22) (122 mg, 0.5 mmol), (3,4-dimethoxyphenyl)boronic acid (15) (218 mg, 1.2 mmol), Pd(PPh$_3$)$_4$ (29 mg, 0.025 mmol) and Cs$_2$CO$_3$ (0.72 g, 2.2 mmol). The mixture was purged with nitrogen and heated in a microwave reactor (Biotage) to 160° C. for 1 h. The reaction mixture was cooled to 23° C., acidified with 1M HCl until the pH was 1, and extracted with. EtOAc. The combined organic extracts were washed with H₂O before being dried over MgSO₄, filtered, and concentrated under reduced pressure. Compound 24 was purified by column chromatography (5%-35% EtOAc in hexanes) as brown-yellow solid (28 mg, 16% yield). 5-bromo-2-(3,4-dimethoxyphenyl)thiazole (23) was also isolated from the reaction above as brown-yellow crystalline solid (28 mg, 19% yield).

SA-64 was prepared by the reaction of 2,5-bis(3,4-dimethoxyphenyl)thiazole (24) (28 mg, 0.078 mmol) and BBr₃ (1M in DCM, 0.75 mL, 0.75 mmol) according to the similar procedure for compound SA-58, and was obtained as a yellow solid (14 mg, 60% yield).

Example 11

Synthesis of SA-65

A mixture of 0.100 g (0.237 mmol) of 10, 0.600 g (1.03 mmol) of hexabutylditin, 5 mL of PhMe, and 1 mL of TEA was degassed by nitrogen purge. Then 0.050 g of Pd(PPh₃)₄ was added. The reaction mixture was refluxed for 16 h. At this time, the reaction was incomplete, but a decomposition product was seen in addition to the desired product. The reaction was at this point concentrated and purified by PTLC to prevent further decomposition to give 0.090 g (60% yield) of SA-65 as an off-white solid. ¹H NMR (200 MHz, CDCl₃) δ 7.68-7.65 (overlapping peak doublet and doublet of doublets, 2H), 7.53 (s, 1H), 7.16 (s, 1H), 6.98 (d, J=9.0 Hz, 1H), 3.99-3.96 (4 overlapping singlets, 12H), 1.55 (m, 6H), 1.44 (m, 6H), 1.15 (m, 6H), 0.84 (t, J=7.2 Hz, 9H).

Example 12

Synthesis of SA-66

A mixture of 0.174 g of Lawesson's reagent, 0.175 g of compound 9, and 20 mL of PhMe was heated to 60° C. for 3 h. The mixture was concentrated, and applied directly to a PTLC plate for purification. The brominated thiadiazole 11 was purified by PTLC and the middle of the desired product spot (fluoresces blue under UV light) was collected to give 0.112 g (65% yield) of compound 11 as an off-white to brown solid.

The above experiment was repeated using 1.13 g of 9, 1.21 g of Lawesson's reagent, and 200 mL of PhMe. The mixture was refluxed 3 h, and quenched with 150 mL of water. The layers were separated, and the aqueous extracted twice with 30 mL of EtOAc. The organic layers were combined and washed twice with 50 mL 1 N aq. HCl, twice with 50 mL saturated aq. NaHCO₃, once with 25 mL of water, and once with 50 mL of brine. The organic was dried, concentrated, and purified by PTLC to give 1.04 g of the desired 11 as a yellow solid (97% yield). ¹H NMR (200 MHz, CDCl₃) δ 7.88 (s, 1H), 7.68 (bs, 1H), 7.51 (d, J=7.8 Hz, 1H), 7.15 (s, 1H), 6.95 (d, J=8.4 Hz, 1H), 4.00-3.95 (4 overlapping singlets, 12H).

A solution of 0.051 g of 11 in 5 mL DCM was cooled to −78° C., treated with 1.5 mL of 2 M BBr₃ in DCM, stirred at −78° C. for 0.5 h, and stirred at 23° C. for 3 h. The mixture was quenched with water carefully, poured into 100 mL brine, and extracted twice with 75 mL of EtOAc. The combined organic layers were dried and concentrated to yield 36 mg (81% yield) of the crude title compound as a yellow solid. The mixture was recrystallized from hot MeOH and precipitated with water to give 0.021 g (50% yield) of SA-66 as a brown solid.

The above experiment was repeated on 0.077 g of starting material using the same procedure with the exception of slightly different stirring times (1 h at −78° C., 4 h at 23° C.) to give 0.054 g (83% yield) of SA-66. ¹H NMR (200 MHz, DMSO-d₆) δ 10.10 (s, 1H), 9.78 (s, 1H), 9.68 (s, 1H), 9.47 (s, 1H), 7.55 (s, 1H), 7.43 (d, J=1.8 Hz, 1H), 7.29 (dd, J=1.8 Hz, 8.0 Hz, 1H), 7.13 (s, 1H), 6.87 (d, J=8.2 Hz, 1H).

Example 13

Synthesis of SA-67

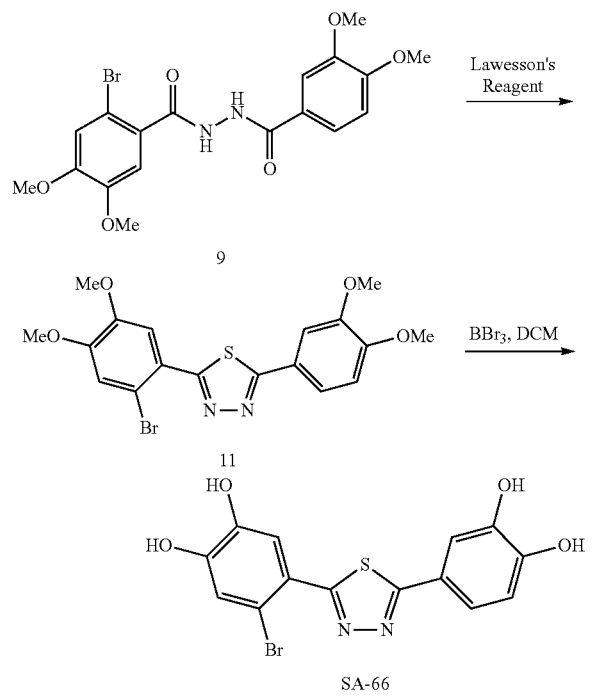

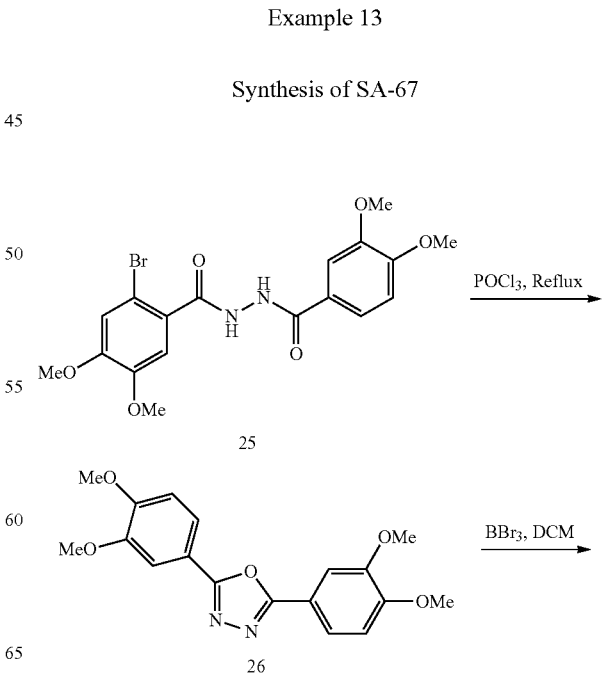

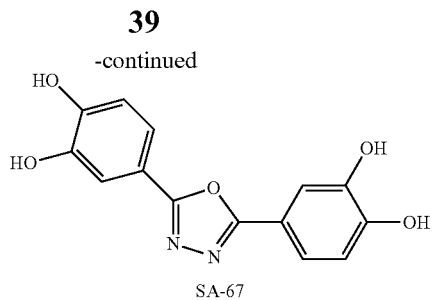

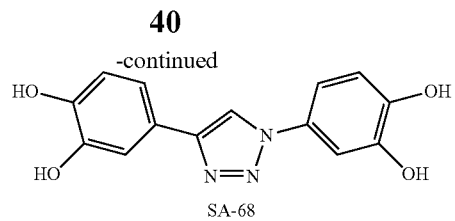

To 0.285 g (1.57 mmol) of 3,4 dimethoxybenzoic acid (1) in 5 mL of DCM was added 0.3 mL (3.5 mmol) of oxalyl chloride and one drop of DMF. The mixture was stirred for 2 h, quenched with hydrazine hydrate (3 mL), concentrated, and dried. The solid was taken up in 25 mL water, sonicated five minutes, filtered, and the resultant solid washed with 40 mL water. The solid was dried, taken up in 20:1 DCM:DMF, and purified by PTLC (8:2 EtOAc:Hexanes) to give 0.056 g (20% yield) of 25 as an off-white solid. $^1$H NMR (200 MHz, DMSO-d$_6$) δ 10.30 (s, 2H), 7.58 (d, J 8.4 Hz, 1H), 7.51 (bs, 1H), 7.18 (d, J=8.4 Hz, 1H), 3.82 (bs, 12H).

To 0.050 g (0.14 mmol) of hydrazide 25 was added 3 mL of POCl$_3$. The mixture was refluxed 2 h, quenched with 50 g of ice, allowed to warm to 23° C., and extracted twice with 25 mL of EtOAc. The organic layers were washed once with 25 mL water, twice with 25 mL of brine, dried with Na$_2$SO$_4$, and concentrated to give 0.043 g (93% yield) of 26 as a white solid. $^1$H NMR (200 MHz, CDCl$_3$) δ 7.72 (d, J=8.0 Hz, 2H), 7.60 (d, J=1.2 Hz, 1H), 7.07 (d, J=8.4 Hz, 1H), 3.89 (s, 6H), 3.87 (s, 6H).

To 0,038 g (0.11 mmol) of oxadiazole 26 was added 3 mL of DCM. The solution was cooled to −78°, and 5 mL of DCM containing 0,450 g (1.8 mmol) of BBr$_3$ was added. The mixture was stirred at −78° C. for 1 h, at 23° C. for 2.5 h, quenched by pouring into 5 mL of MeOH, and concentrated to 1 mL. The resultant oil was diluted with 5 mL water and the resultant precipitate was filtered to give 0.017 g (56% yield) of SA-67 as a yellow solid. $^1$H NMR (200 MHz, DMSO-d$_6$) δ 9.74 (bs, 2H), 9.51 (bs, 2H), 7.43 (d, J=2.0 Hz, 1H), 7.37 (dd, J=2.0 Hz, 8.4 Hz, 1H), 6.93 (d, J=8.0 Hz, 1H).

Example 14

Synthesis of SA-68

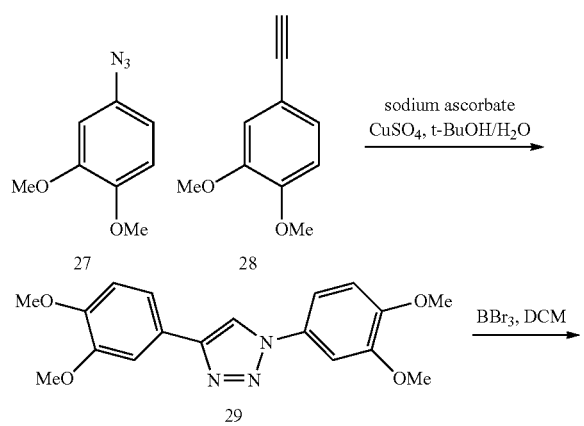

4-azido-1,2-dimethoxybenzene (27) (62 mg, 0.31 mmol), 4-ethynyl-1,2-dimethoxy benzene (28) (52 mg, 0.31 mmol), sodium ascorbate (0.25 mL of 1M solution, 0.25 mmol), CuSO$_4$ (0.020 mL of 1M solution, 0.020 mmol) and tBuOH/H$_2$O (2 mL, 1/1) were added to a vial. The reaction mixture was purged with nitrogen, stirred at 23° C. overnight, poured into water at 0° C., and the resultant brown solid was filtered. This solid was washed with water (1 mL) and Et$_2$O (1 mL). Compound 29 (99 mg, 93% yield) was used in the next step without further purification.

SA-68 was prepared by the reaction of 1,4-bis(3,4-dimethoxyphenyl)-1H-1,2,3-triazole (29) (67 mg, 0.20 mmol) and BBr$_3$ (1M in DCM, 0.79 mL, 0.79 mmol) according to the similar procedure for compound SA-52. SA-68 was obtained as a dark brown solid (56 mg, 98% yield).

Example 15

Synthesis of SA-69

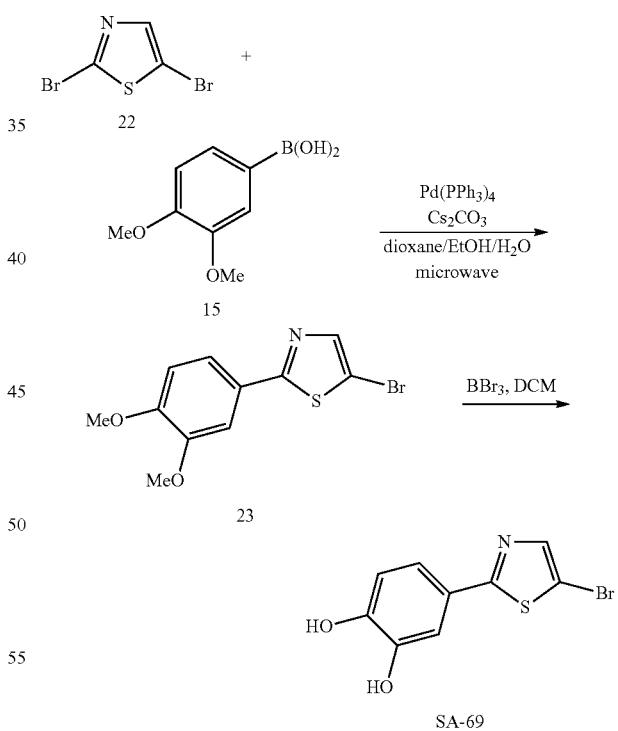

To a solution of dioxane/EtOH/H$_2$O (6 mL, 1/1/1) were added 2,5-dibromothiazole (22) (756 mg, 3.1 mmol), (3,4-dimethoxyphenyl)boronic acid (15) (380 mg, 2.1 mmol), Pd(PPh$_3$)$_4$ (58 mg, 0.05 mmol) and Cs$_2$CO$_3$ (1.4 g, 4.4 mmol) in a 20 mL microwave reaction vial (Biotage). The solution was purged with nitrogen and heated in a microwave reactor (Biotage) to 160° C. for 30 min. The reaction mixture was cooled to 23° C., acidified with 1M HCl until pH=1, and extracted with EtOAc. The combined organic extracts were washed with H$_2$O before being dried over MgSO$_4$, filtered, and concentrated under reduced pressure. Compound 23 was purified by flash column chromatography (8%-50% EtOAc in hexanes) as brown-yellow solid (193 mg, 32% yield). 2,5-bis (3,4-dimethoxyphenyl)thiazole (24), was also isolated as a brown-yellow solid (34 mg, 5% yield).

SA-69 was prepared by the reaction of 5-bromo-2-(3',4'-dimethoxyphenyl)thiazole (23) (78 mg, 0.26 mmol) and BBr$_3$ (1M in DCM, 0.65 mL, 0.65 mmol) according to the similar procedure for compound SA-52, and was obtained as a brown-yellow solid quantitatively.

Example 16

Synthesis of SA-70

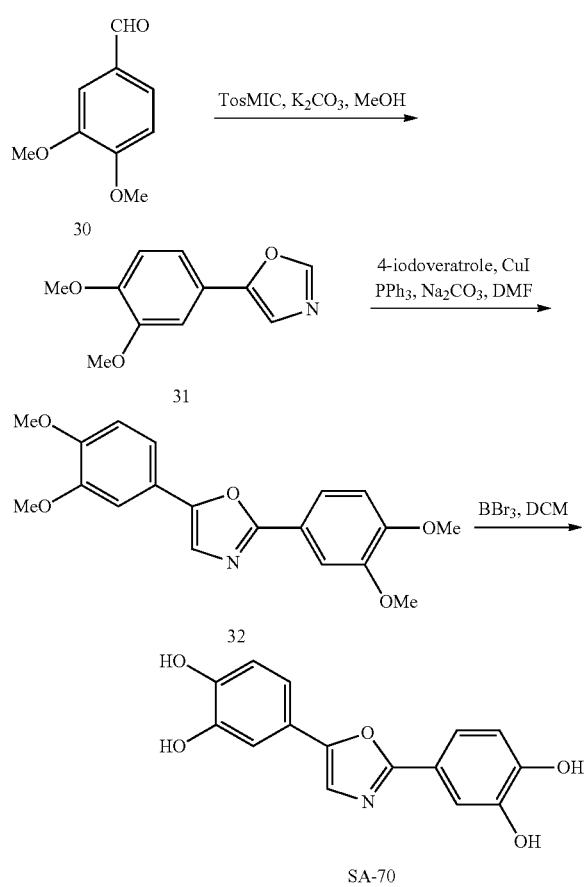

A mixture of 0.996 g (6 mmol) 3,4-dimethoxybenzaldehyde (30), 1.25 g of TosMIC (6.4 mmol), and 0.923 g (6.6 mmol) of K$_2$CO$_3$ was refluxed in 30 mL of MeOH for 3 h. The reaction mixture was quenched by pouring into 200 mL of a 1:1 mixture of brine and water, cooled to −20° C. for 1 h, and the resultant solid filtered to give 0.952 g (77% yield) of 31 as an off-white solid. $^1$H NMR (200 MHz, CDCl$_3$) δ 7.85 (s, 1H), 7.22 (s, 1H), 7.20 (overlapping peak, 1H), 7.15 (dd, J=2.0 Hz, 12.4 Hz, 1H), 6.88 (d, J=1H), 3.91 (s, 3H), 3.88 (s, 3H).

A suspension of 0.212 g of Na$_2$CO$_3$ (2 mmol), 0.262 g of PPh$_3$ (1 mmol), 0.206 g (1 mmol) of 31 and 0.316 g of 4-iodoveratrole (1.2 mmol) was formed in 1 mL of DMF. Then, 0.190 g (1 mmol) of CuI was added. The mixture was stirred at 160° C. for 3 h and quenched by pouring into 50 mL of water containing 5% NH$_4^+$OH$^−$. The product was extracted with 50 mL DCM, the organic layer dried and concentrated, and the crude product purified by PTLC to give 0.174 g (51% yield) of 32 as a yellow solid. $^1$H NMR (200 MHz, CDCl$_3$) δ 7.60 (d, J=8.4 Hz, 1H), 7.54, (bs, 1H), 7.24 (s, 1H), 7.19 (bs, 1H), 7.10 (s, 1H), 6.90-6.83 (m, 2H), 3.91-3.86 (4 overlapping multiplets, 12H). $^{13}$C NMR (50 MHz, CDCl$_3$) δ 160.7, 150.9, 149.3, 149.2, 132.1, 132.0, 122.0, 121.2, 120.4, 119.3, 117.1, 111.5, 111.1, 109.1, 107.5, 56.01, 55.92.

A mixture of 0.075 g (0.22 mmol) of 32 in 15 mL DCM was treated with 0.500 g (2 mmol) of BBr$_3$ at −78° C. The mixture was stirred at −78° C. for 0.5 h, then 2 h at 23° C. The reaction was then quenched with 5 mL MeOH, concentrated to 1 mmol and diluted with 5 mL of water. The resultant precipitate was filtered to give 0.021 g (33% yield) of SA-70 as a yellow solid. $^1$H NMR (200 MHz, DMSO-d$_6$) δ 7.40 (s, 2H), 7.31 (dd, J=2.0 Hz, 8.0 Hz, 1H), 7.13 (d, J=2.2 Hz), 7.05 (dd, J=2.2 Hz, 8.2 Hz, 1H), 6.86 (d, J=7.8 Hz, 1H), 6.82 (d, J=7.8 Hz, 1H). HRMS Calculated for C$_{15}$H$_{12}$NO$_5$ (M+H)$^+$ 286.0715. found 286.0717.

Example 17

Synthesis of SA-72

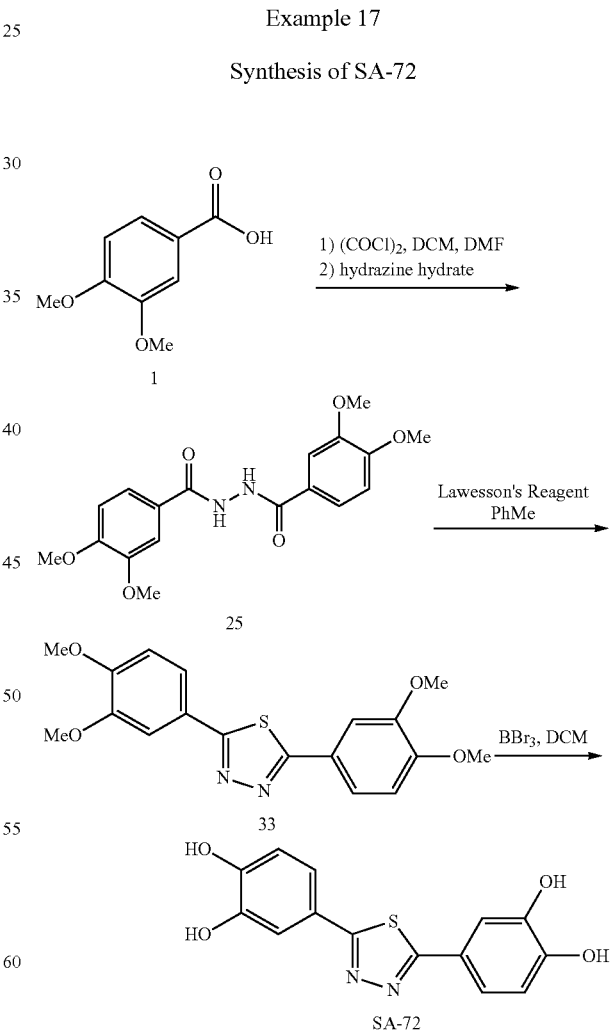

A solution of 0.115 g (0.32 mmol) of 25 in 30 mL of PhMe was treated with 0.140 g of Lawesson's reagent (0.35 mmol) and stirred 3 h at 100° C. The reaction mixture was poured into 75 mL water, shaken vigorously, and extracted with 50 mL EtOAc. The organic layers were combined, washed with 25 ml saturated aqueous NaHCO$_3$, washed with 50 mL brine, dried, and concentrated. The crude product was purified by PTLC to give 0.088 g (74% yield) of 33 as a yellow solid. $^1$H NMR (200 MHz, CDCl$_3$) δ 7.60 (bs, 2H), 7.37 (d, J=8.2 Hz, 2H), 6.86 (d, J=8.4 Hz, 2H), 3.95 (s, 6H), 3.90 (s, 6H). $^{13}$C NMR (200 MHz, CDCl$_3$) 167.3, 151.6, 149.4, 123.2, 121.6, 111.2, 110.0, 56.1, 56.0. HRMS Calculated for C$_{16}$H$_{19}$N$_2$O$_4$S (M+H) 359.1066. found 359.1061.

A solution of 0.077 g (0.22 mmol) of 33 and 3 mL DCM was treated with 0.250 g BBr$_3$ at −78° C. The reaction mixture was stirred 1 h, treated with 0.250 g BBr$_3$, and stirred an addition 15 min at −78° C. The mixture was warmed to 23° C., stirred for 1 h, quenched with 10 mL MeOH, and concentrated. The concentrate was taken up in 1 mL MeOH, warmed until a solution, and precipitated with 10 mL water. The resultant solid was filtered and dried to give 0.054 g of SA-72 (83% yield) as an off-white solid. $^1$H NMR (200 MHz, DMSO-d$_6$) 10.0-9.0 (broad peak, 4H), 7.41 (d, J=2.2 Hz, 2H), 7.24 (dd, J=2.2 Hz, 8.2 Hz, 1H), 6.87 (d, J=8.2 Hz, 2H).

Example 18

Synthesis of SA-74

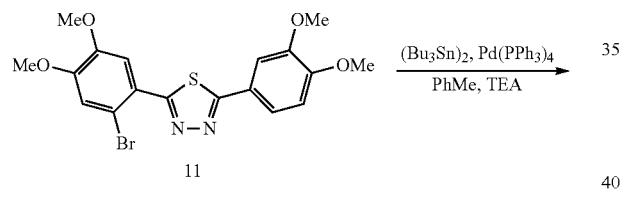

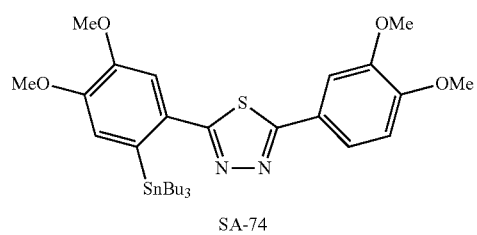

To a mixture of 0.219 g (0.5 mmol) of 11 in 20 mL PhMe was added 1.09 g (Bu$_3$Sn)$_2$ and 2 mL of triethylamine. The mixture was degassed via a nitrogen purge, treated with 0.150 g (0.13 mmol) of Pd(PPh$_3$)$_4$, and refluxed for 15 h. The mixture was concentrated and purified directly by PTLC by eluting the plates with 1% TEA in hexanes then 50% EtOAc in hexanes with 1% TEA successively. This gave 0.224 g (69% yield) SA-74 as an off-white solid.

Example 19

Synthesis of SA-75 and SA-76

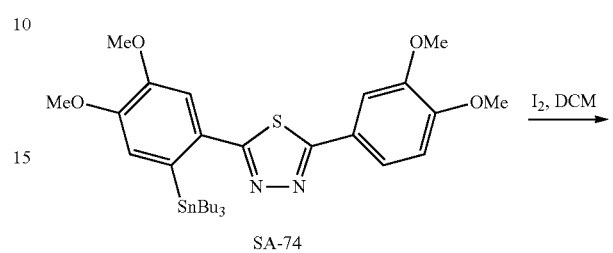

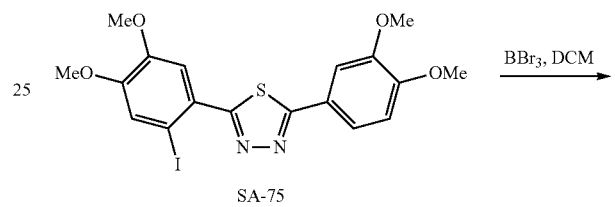

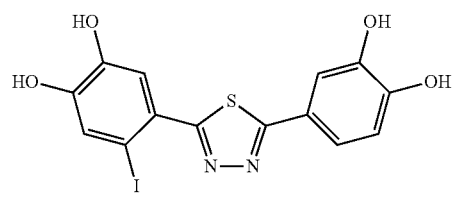

A solution of 0.051 g of SA-74 in 3 mL of DCM was treated with a 1 M iodine in DCM solution until the orange/yellow color of the iodine persists. The mixture was quenched with a 1 M solution of KF in MeOH (2 mL) then sat. aq. Na$_2$S$_2$O$_3$ (2 mL). The mixture was extracted twice with 10 mL EtOAc. The organic layers were combined, washed with 10 mL water, dried and concentrated to give the crude title compound. The crude product was purified by PTLC with another run of this reaction using 0.082 g of SA-74 and run in the same manner as described above. This gave 0.012 g (12% yield) of SA-75 as a yellow solid. $^1$H NMR (200 MHz, CDCl$_3$) δ 7.73 (d, J=2.2 Hz, 1H), 7.59 (s, 1H), 7.54 (dd, J=2.2 Hz, 8.4 Hz), 7.42 (s, 1H), 6.98 (d, J=8.4 Hz, 1H), 4.03-3.95 (4 overlapping singlets, 12H).

A solution of 0.008 g of SA-75 in 1 mL of DCM was cooled to 0° C., treated with 0.5 mL of 1 M BBr$_3$ in DCM, and stirred for 1 h. The reaction was treated with an additional 1 mL portion of 1 M BBr$_3$ in DCM, stirred an additional 2 h at 0° C., and warmed to 23° C. The reaction mixture was stirred an additional 0.5 h, quenched with 3 mL MeOH, and concentrated to 0.5 mL. The product was precipitated with 5 mL water, and the resultant yellow solid was filtered and dried to give (0.002 g) of SA-76 as a yellow-green solid. $^1$H NMR (200 MHz, DMSO-d$_6$) δ 9.93-9.50 (overlapping broad singlets, 4H), 7.42-7.28 (overlapping irresolvable peaks, 4H), 6.98 (d, J=8.2 Hz, 1H).

Example 20

Synthesis of SA-77 and SA-78

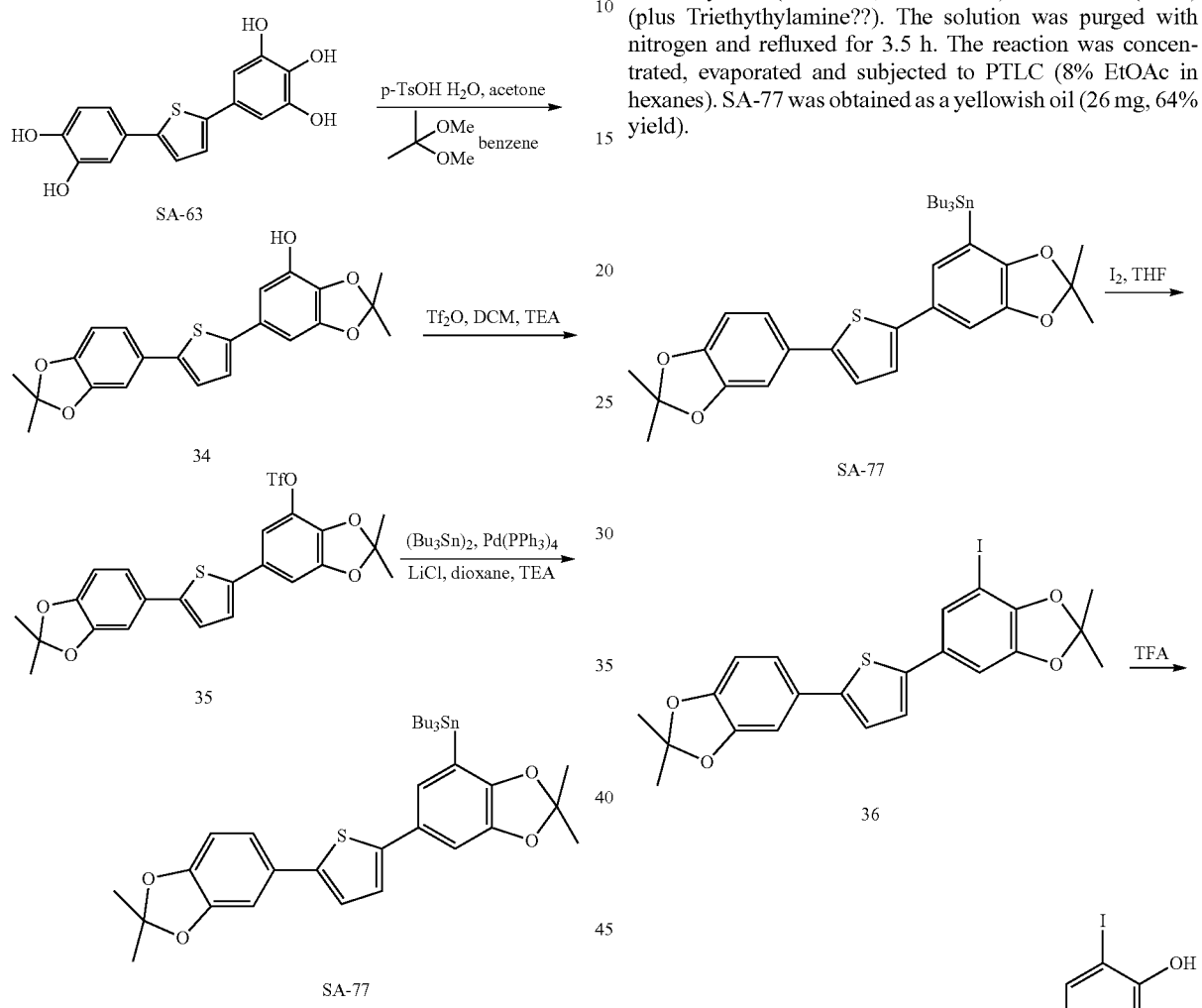

To a round-bottom flask charged with 5-(5-(3,4-dihydroxyphenyl)thiophen-2-yl)benzene-1,2,3-triol (SA-63) (145 mg, 0.46 mmol), 4-methylbenzenesulfonic acid (p-TsOH.H$_2$O) (8.7 mg, 0.046 mmol), and 2,2-dimethoxypropane (0.45 mL, 3.7 mmol) were added acetone (3 mL) and benzene (15 mL). A short column with 4 Å molecular sieves and a condenser were installed on the flask. The reaction was refluxed for 15 h. An additional portion of 2,2-dimethoxypropane (0.45 mL, 3.7 mmol) was added, and the reaction was refluxed for another 24 h. The solution was concentrated at reduced pressure and purified by PTLC, which afforded 34 as a white solid (53 mg, 29%).

To a solution of 6-(5-(2,2-dimethylbenzo[d][1,3]dioxol-5-yl)thiophen-2-yl)-2,2-dimethylbenzo[d][1,3]dioxol-4-ol (34) (53 mg, 0.13 mmol), triethylamine (0.056 mL, 0.40 mmol) and DCM (2 mL) was added trifluoromethanesulfonic anhydride (0.034 mL, 0.20 mmol) at 0° C. The reaction was warmed to 23° C. after 30 min and extracted with DCM. The organic layer was washed with sat. aq. NaHCO$_3$, H$_2$O and brine. The organic layers were dried over MgSO$_4$, concentrated, and 35 was obtained as yellowish oil (53 mg, 75% yield).

To 6-(5-(2,2-dimethylbenzo[d][1,3]dioxol-5-yl)thiophen-2-yl)-2,2-dimethylbenzo[d][1,3]dioxol-4-yl trifluoromethanesulfonate (35) (32 mg, 0.061 mmol) was added Pd(PPh$_3$)$_4$ (14 mg, 0.012 mmol), LiCl (26 mg, 0.61 mmol), bistributylditin (0.153 mL, 0.305 mmol) and dioxane (2 mL) (plus Triethythylamine??). The solution was purged with nitrogen and refluxed for 3.5 h. The reaction was concentrated, evaporated and subjected to PTLC (8% EtOAc in hexanes). SA-77 was obtained as a yellowish oil (26 mg, 64% yield).

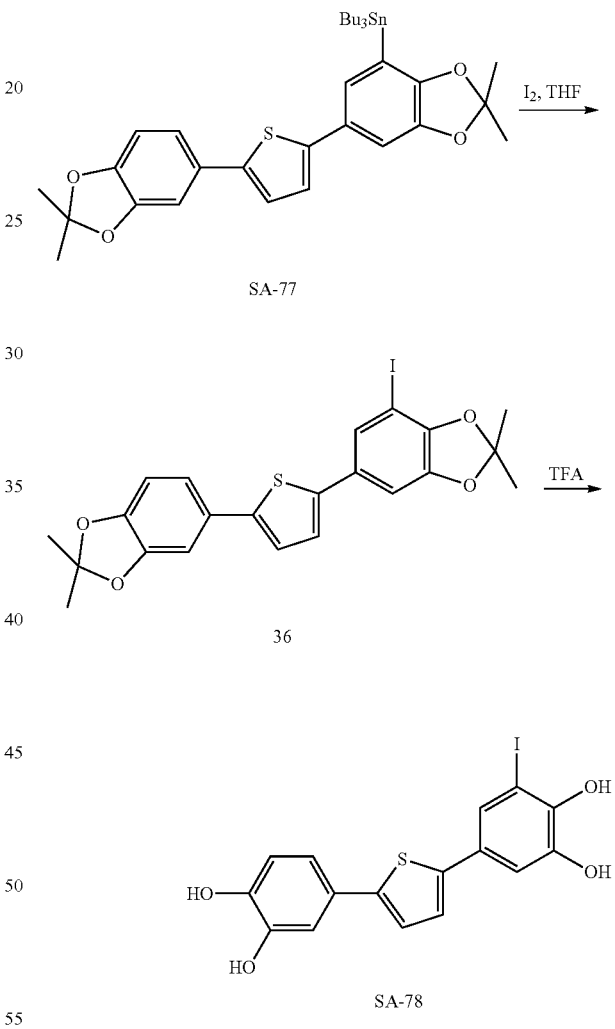

To the solution of tributyl(6-(5-(2,2-dimethylbenzo[d][1,3]dioxol-5-yl)thiophen-2-yl)-2,2-dimethylbenzo[d][1,3]dioxol-4-yl)stannane (SA-77) (26 mg, 0.039 mmol) and THF (1 mL) was added the solution of I$_2$ (20 mg, 0.078 mmol) in THF (1 mL) dropwise. The reaction was stirred for 10 min and concentrated, and 36 was obtained quantitatively as a yellow solid after purification by PTLC (7% EtOAc in hexanes).

To 6-(5-(2,2-dimethylbenzo[d][1,3]dioxol-5-yl)thiophen-2-yl)-4-iodo-2,2-dimethylbenzo[d][1,3]dioxole (36) (15 mg, 0.029 mmol) were added a few drops of H$_2$O and trifluoroacetic acid (0.45 mL). The reaction was stirred at 23° C. for 1 h, and afforded SA-78 quantitatively as a white crystal after concentration at reduced pressure.

Example 21

Synthesis of SA-79 and 80

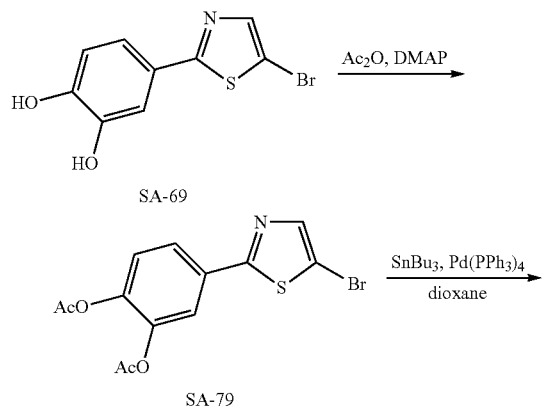

To 4-(5-bromothiazol-2-yl)benzene-1,2-diol (SA-69) (90 mg, 0.32 mmol) was added 4-dimethylaminopyridine (DMAP) (117 mg) and acetic anhydride (3 mL). The reaction was stirred at 23° C. for 1 h before it was extracted with EtOAc. The organic layer was washed with sat. aq. NaHCO$_3$, H$_2$O and brine and dried over MgSO$_4$. SA-79 was obtained as yellow solid (74 mg, 65% yield) after PTLC (20% EtOAc in hexanes).

To a solution of 4-(5-bromothiazol-2-yl)-1,2-phenylene diacetate (SA-79) (36 mg, 0.10 mmol), Pd(PPh$_3$)$_4$ and dioxane (2 mL) was added bistributyltin (0.25 mL, 0.50 mmol). The solution was purged with nitrogen and refluxed for 1.5 h. PTLC (25% EtOAc in hexanes) provided SA-80 as yellow oil (22 mg, 39% yield).

Example 22

Synthesis of SA-81

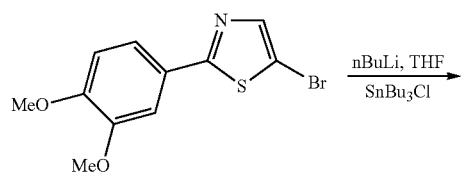

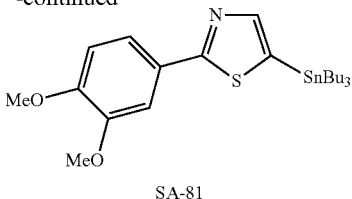

To a solution of nBuLi (0.34 mL, 2.5 M in hexanes) and THF (6 mL) was added 5-bromo-2-(3,4-dimethoxyphenyl)thiazole (23) (54 mg, 0.18 mmol) and additional THF (3 mL) was added dropwise at −78° C. under nitrogen atmosphere. SnBu$_3$Cl (0.15 mL) was added after the reaction was stirred at −78° C. for 30 min. After another 30 min, saturated aqueous NaHCO$_3$ was added to quench the reaction. The mixture was extracted with EtOAc and the organic layer was washed with water and brine. PTLC (25% EtOAc in hexanes) provided SA-81 as a yellow oil (58 mg, 63% yield).

Example 23

Synthesis of SA-82

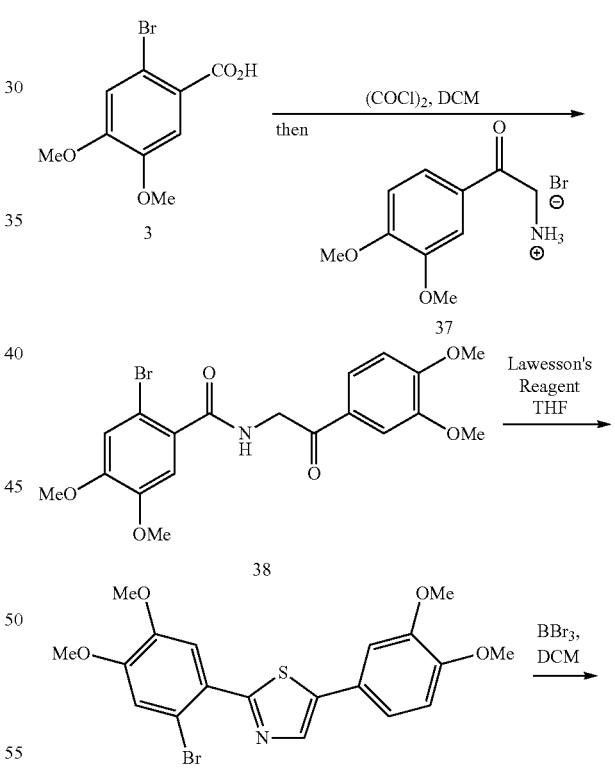

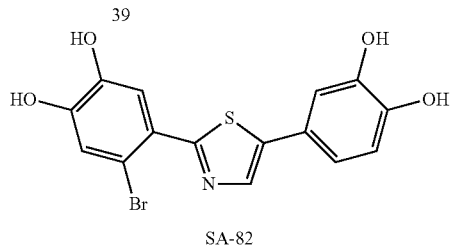

A mixture of 0.26 g (1 mmol) of 2-bromo-4,5-dimethoxybenzoic acid (3) in 5 mL of DCM was treated with 0.3 mL of (COCl)$_2$ and two drops of DMF. The mixture was stirred for an additional hour after a yellow solution had formed (about 2 h total). The mixture was concentrated and dried in vacuo thoroughly, taken up in 15 mL of DCM, cooled to 0° C., and treated with 2 mL pyridine. Then 0.79 g of known amine 37 was added. The mixture was warmed to 23° C., stirred 3 days, and quenched with water. The product was extracted with 10 mL of DCM, the combined organic was washed with 10 mL water, dried, and concentrated to give the crude product that was purified by PTLC (50% EtOAc in hexanes) to give 0.070 g (16% yield) of compound 38 as a light brown solid. $^1$H NMR (200 MHz, CDCl$_3$) δ 7.67 (dd, J=2.0 Hz, 8.4 Hz, 1H), 7.56 (apparent broad singlet, overlapping peaks, 2H), 7.04 (s, 1H), 6.95 (d, J=6.95 Hz, 1H), 4.94 (d, J=4.2 Hz, 1H), 3.98 (s, 3H), 3.95 (s, 3H), 3.86 (bs, 6H). HRMS Calculated for C$_{19}$H$_{22}$O$_6$NBr (M+H)$^+$ 438.0552. found 438.0556.

A mixture of 0.103 g (0.24 mmol) of amide 38 in 10 mL of THF was treated with 0.117 g (0.29 mmol) of Lawesson's reagent. The mixture was refluxed for 2 h, cooled, and concentrated. The crude product was purified directly by PLTC to give 0.048 g (45% yield) of compound 39 as a light brown solid. $^1$H NMR (200 MHz, CDCl$_3$) δ 7.78 (apparent singlet, 1H), 7.55-7.50 (overlapping singlet, dd, 2H), 7.46 (s, 1H), 7.13 (s, 1H), 6.94 (d, J=8.8 Hz, 1 h), 3.97-3.89 (overlapping singlets, 12H).

A solution of 0.031 g 39 (0.07 mmol) in 4 mL of DCM was cooled to −78° C., and treated with 1.5 mL of 1 M BBr$_3$ in DCM. The mixture was stirred for 1 h at −78° C., 1 h at 23° C., and quenched with 2 mL of MeOH. The mixture was concentrated to 1 mL, diluted with 10 mL water, sonicated, and the resultant solid filtered to give 0.009 g (35% yield) of SA-82 as an off-white solid.

Example 24

Synthesis of SA-83

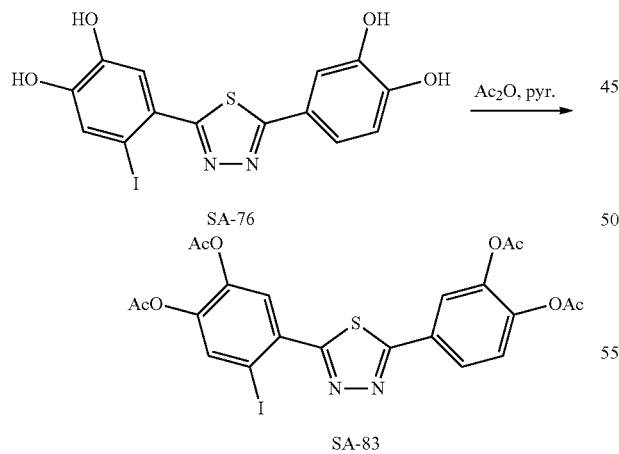

To 0.012 g (0.03 mmol) of SA-76 in 0.5 mL pyridine was added 0.05 mL of acetic anhydride. The mixture was stirred at 140° C. for 3 h, cooled, and poured into 10 mL of water with 0.5 g NH$_4^+$Cl$^-$, and the product was extracted with 5 mL 10% MeOH in DCM. The extract was concentrated, and purified by PTLC to give 0.005 g (8.3*10$^{-3}$ mmol) of SA-83 as a brown oil. $^1$H NMR (200 MHz, CDCl$_3$) δ 7.94-7.88 (3 overlapping irresolvable peaks, 3H), 7.82 (s, 1H), 7.36 (d, J=9.0 Hz), 2.34-2.32 (4 overlapping singlets, 12H).

Example 25

Synthesis of SA-84

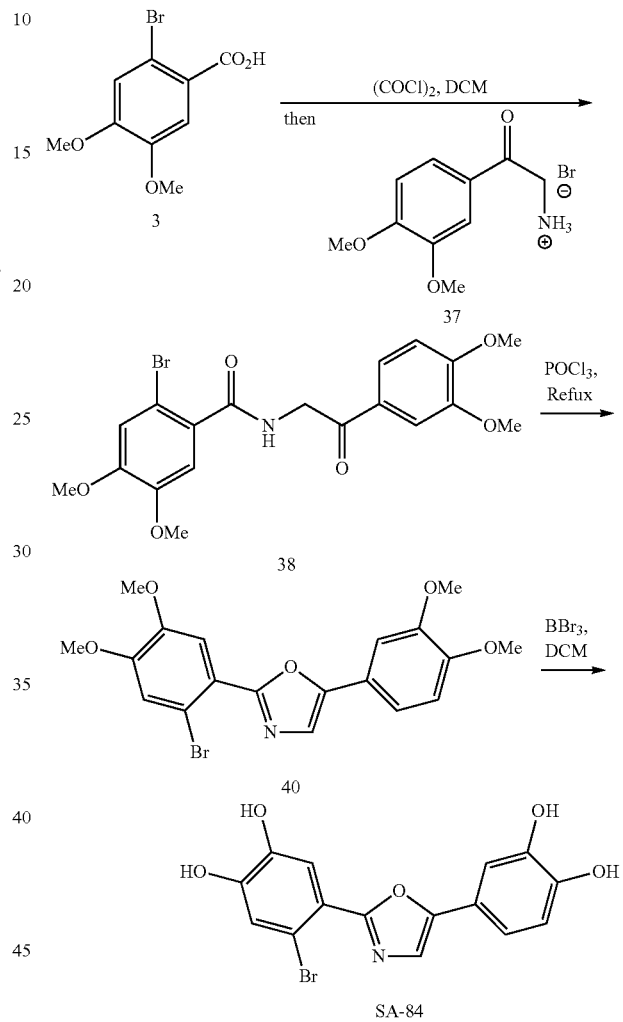

A mixture of 0.058 g (0.132 mmol) of amide 38 was refluxed in 2 mL POCl$_3$. The solution was added to 50 mL of water and sonicated to precipitate a light yellow solid, which was filtered, washed with cold water, and dried to give 0.041 g (74% yield) of 40 as a yellow solid. $^1$H NMR (200 MHz, CDCl$_3$) δ 7.61 (s, 1H), 7.37 (d, J=2.0 Hz, 1H), 7.31 (dd, J=2.2 Hz, 8.4 Hz, 1H), 7.25 (s, 1H), 7.18 (s, 1H), 6.96 (d, J=8.4 Hz, 1H), 3.96 (overlapping singlets, 12H). HRMS Calculated for C$_{19}$H$_{19}$BrNO$_5$ (M+H)$^-$ 420.0448. found 420.0465.

To 0.100 g (0.24 mmol) of 40 in 20 mL of DCM at −78° C. was added 2.5 mL of 1 M BBr$_3$ in DCM. The reaction was warmed to 23° C., stirred for 3 h, and quenched with 10 mL of MeOH. The reaction mixture was concentrated, and water was added to precipitate the product. This did not yield any solid, so the crude product was reconcentrated and purified by PTLC (10% MeOH in DCM) to give, after 2 weeks drying, 0.040 g (46% yield) of SA-84 as a yellow-green solid. $^1$H NMR (200 MHz, DMSO-d$_6$) δ 7.50 (s, 1H), 7.44 (s, 1H), 7.16

(d, J=2.0 Hz), 7.09 (s, 1H), 7.08 (dd, coupling constants not resolvable due to overlapping singlet, 1H), 6.83 (d, J=8.2 Hz, 1H).

Example 26

Synthesis of SA-86

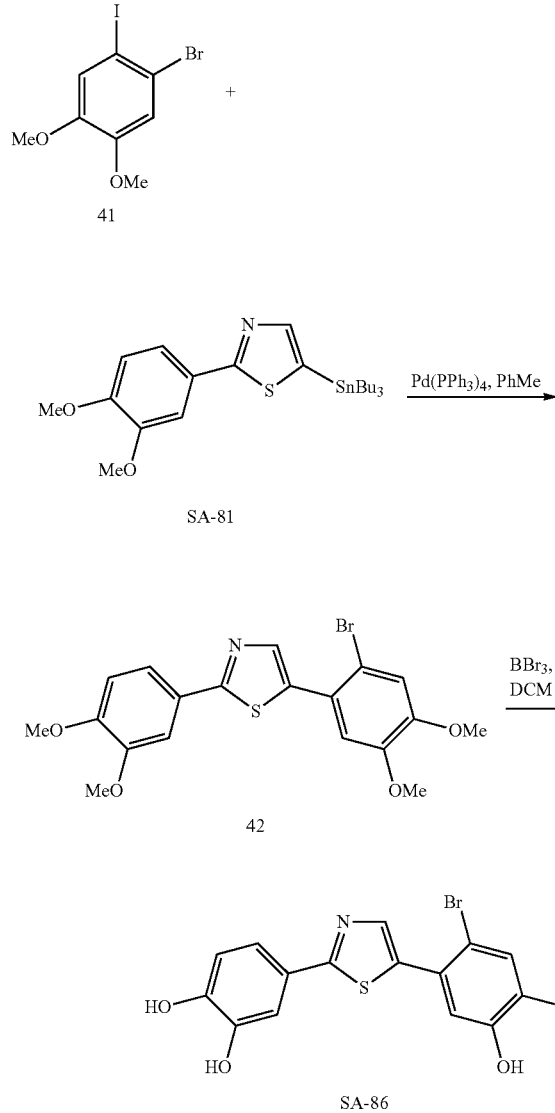

To a mixture of 1-bromo-2-iodo-4,5-dimethoxybenzene (41) (27 mg, 0.078 mmol), Pd(PPh₃)₄ (4.1 mg, 5 mol %) and toluene (1 mL) was added the solution of 2-(3,4-dimethoxyphenyl)-5-(tributylstannyl)thiazole (SA-81) (36 mg, 0.070 mmol) and toluene (1 mL). The reaction was purged with nitrogen and refluxed 16 h. The concentrated reaction mixture was purified by PTLC (35% EtOAc in hexanes) and afforded 42 (20 mg, 65% yield).

SA-86 was prepared by the reaction of 5-(2-bromo-4,5-dimethoxyphenyl)-2-(3,4-dimethoxyphenyl) thiazole (42) (20 mg, 0.046 mmol) and BBr₃ (in DDM??) (0.46 mL, 0.46 mmol) according to the similar procedure for compound SA-58, and obtained SA-86 as a yellow solid quantitatively.

Example 27

Synthesis of SA-87

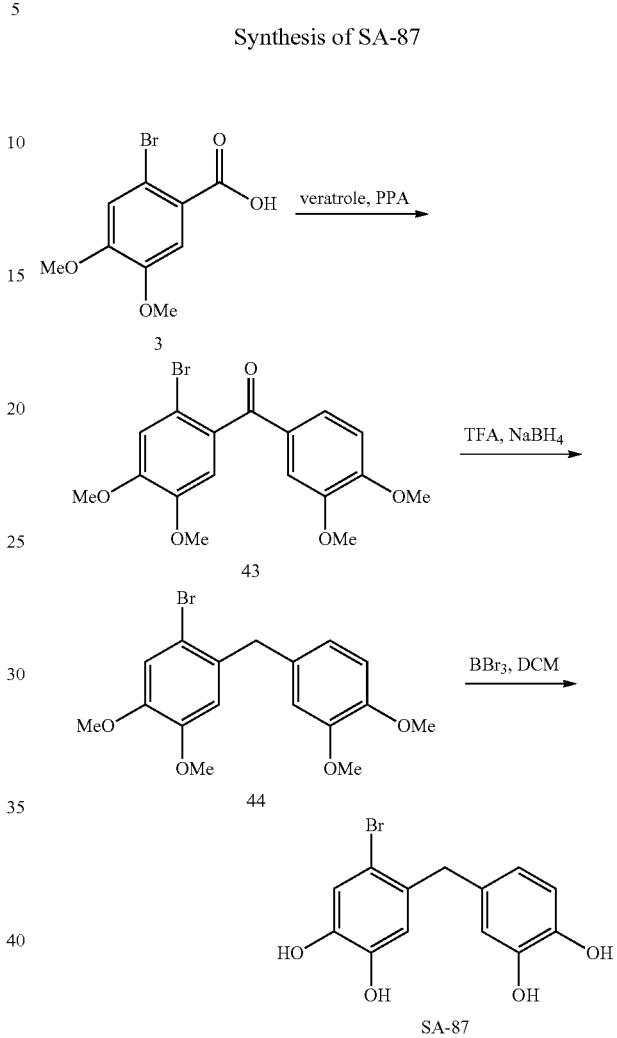

2-Bromo-4,5-dimethoxybenzoic acid (3) (4.50 g, 17.6 mmol), veratrole (2.44 g, 17.7 mmol), and 60 g of polyphosphoric acid (PPA) were heated to 80° C. for 45 min. The reaction mixture turned a deep orange color during this time. The crude mixture was treated with 400 mL of water, allowed stir overnight, and the resultant crude product was filtered as a brownish solid. The solid was recrystalized twice from ethanol to give 1.89 g (28% yield) of benzophenone 43. ¹H NMR (CDCl₃, δ) 7.54 (d, J=2.0 Hz, 1H), 7.26 (dd, J=2.0, 8.0 Hz), 7.07 (s, 1H), 6.90-6.83 (overlapping peaks, 3H), 3.95 (s, 6H), 3.88 (s, 3H), 3.84 (s, 3H).

Benzophenone 43 (1.31 g, 3.4 mmol) in 10 mL DCM was added to a solution of 1.00 g NaBH₄ (26 mmol) in 10 mL of TFA. Caution: the reaction between NaBH₄ and TFA is extremely exothermic with the evolution of hydrogen gas. It is recommended that: (1) an ice bath be used when the addition is occurring and (2) NaBH₄ pellets are used as opposed to powder. The mixture was stirred 16 h, quenched with 15 mL of water, and diluted with 20 mL of DCM. The aqueous layer was made basic with 10 N NaOH, the layers were separated, the aqueous layer extracted with one portion of 10 mL DCM, and the organic layer dried with Na₂SO₄ and concentrated.

Flash 40+M column chromatography (Biotage) gave 1.15 g (91% yield) of 44 as a thick, yellow oil.

$^1$H NMR (CDCl$_3$, δ) 7.04 (s, 1H), 6.80 (d, J=8.2 Hz, 1H), 6.74-6.66 (overlapping peaks, 2H), 6.63 (s, 1H), 3.99 (s, 2H), 3.86 (s, 6H), 3.84 (s, 3H), 3.77 (s, 3H).

Bromide 44 (0.056 g, 0.172 mmol) in 2 mL of DCM was cooled to 0° C. and treated with 1 mL of 2 M BBr$_3$ in DCM. The mixture was stirred 2 h while allowing to warm to ~23° C., quenched with methanol, and concentrated. The crude, concentrated product was treated with 10 mL of water, extracted twice with eight mL of ethyl acetate, and the organic layers were concentrated to give the SA-87 as an off-white solid.

$^1$H NMR (CDCl$_3$, δ) 6.93 (d, J=8.2 Hz, 1H), 6.62-6.57 (overlapping peaks, 2H), 6.51 (bs, 1H), 6.43-6.40 (m, 1H), 3.67 (s, 2H).

Example 28

Synthesis of SA-88 and SA-90

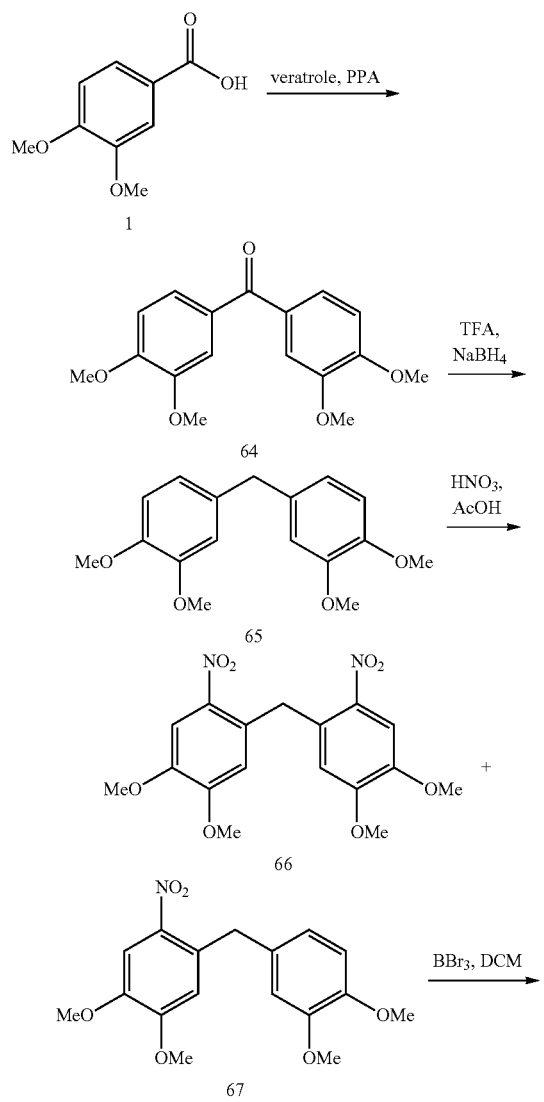

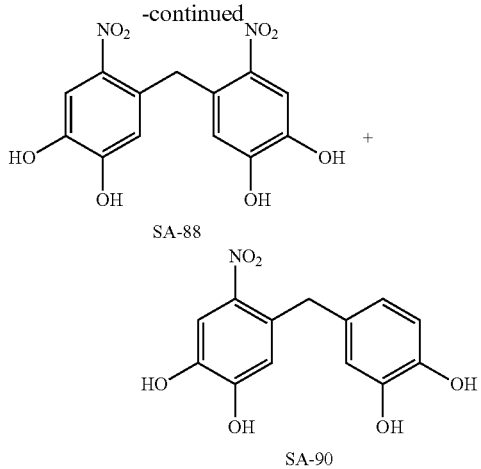

3,4-dimethoxybenzoic acid (1) (3.75 g, 20.6 mmol), veratrole (2.86 g, 20.7 mmol), and 80 g of polyphosphoric acid (PPA) were heated to 80° C. with stirring via overhead stirrer for 1 h. Water was added, and the mixture was stirred until a solid formed. This solid was filtered, recrystalized twice from ethanol, filtered, and dried to give 3.79 g (61% yield) of benzophenone 64.

$^1$H NMR (CDCl, δ) 7.43 (d, J=2.0 Hz, 2H), 7.38 (dd, J=2.0, 8.2 Hz, 2H), 6.90 (d, J=8.2 Hz, 2H), 3.96 (s, 6H), 3.94 (s, 6H).

Benzophenone 64 (0.50 g, 1.66 mmol) was dissolved in 4 mL of DCM and added to a solution made from NaBH$_4$ (0.356 g, 9.4 mmol) and 3 mL TFA. The resultant mixture was stirred 18 h, diluted with 15 mL of DCM and 10 mL of water, made basic with 10 N NaOH, and the layers separated. The aqueous was extracted once more 10 mL of DCM, and the combined organic layers were dried and concentrated. The crude product was purified by PTLC to give 0.42 g (88% yield) of 65.

The previous reaction was repeated using 1.12 g of benzophenone 64 with the other reagents scaled appropriately, and gave 0.86 g (81% yield) of 65.

$^1$H NMR (CDCl$_3$, δ), 6.83-6.78 (m, 2H), 6.75-6.69 (m, 4H), 3.88-3.83 (multiple singlets, 14).

A solution of 65 (0.500 g, 1.7 mmol) in 3 mL of AcOH was treated with 0.120 g of 69% aq. HNO$_3$ (1.3 mmol) and stirred for 1.5 h. The mixture was poured into 50 mL of water, and extracted twice with 25 mL of ethyl acetate. The combined organic layers were washed three times with 20 mL of water, dried, and concentrated to give the crude product, which was purified by PTLC to give 0.123 g of 65 (25% recovery), 0.137 g (24% yield) of 67, and 0.041 g (6% yield) of 66.

$^1$H NMR of 66 (CDCl$_3$, δ), 7.65 (s, 2H), 6.54, (s, 2H), 4.66 (s, 2H), 3.93 (s, 6H), 3.80 (s, 6H). $^1$H NMR of 67 (CDCl$_3$, δ), 7.60 (s, 1H), 6.79-6.63 (overlapping peaks, 4H), 4.26 (s, 2H), 3.91-3.81 (m, 12H).

$^{13}$C NMR of 67 (CDCl$_3$, δ), 153.0, 149.1, 147.7, 147.3, 131.6, 131.3, 120.9, 113.6, 112.4, 111.3, 108.2, 56.42, 56.27, 55.9, 38.3.

A mixture of 66 (0.030 g, 0.08 mmol) in 3 mL of DCM was treated with 1 mL of 2 M BBr$_3$ and stirred 2.5 h. Methanol (10 mL) was added to quench the reaction, the mixture was concentrated, and water was added. The resultant brown solid was filtered and not purified further (due to lack of solubility of the product) to give 0.007 g (27% yield) of SA-88.

$^1$H NMR (DMSO-d$_6$, 8), 8.87 (bs, 2H), 8.71 (bs, 2H), 7.56 (s, 4H), 3.48 (s, 2H).

A mixture of 67 (0.030 g, 0.09 mmol) in 2 mL of DCM was treated with 1 mL of 2 M BBr$_3$ and stirred for 2.5 h. Methanol (10 mL) was added to quench the reaction, the mixture concentrated, and treated with 10 mL of water. This was extracted with 10 mL of ethyl acetate, dried, and concentrated to give 8 mg (32% yield) of SA-90 as a thick brown oil that slowly solidified.

$^1$H NMR (DMSO-d$_6$, δ), 7.54, (s, 3H), 6.97-6.93 (overlapping peaks, 2H), 6.50 (d, 1H, overlapping with next peak), 6.45 (d, J=2.0 Hz, 1H), 3.85 (s, 2H)

Example 29

Synthesis of SA-93

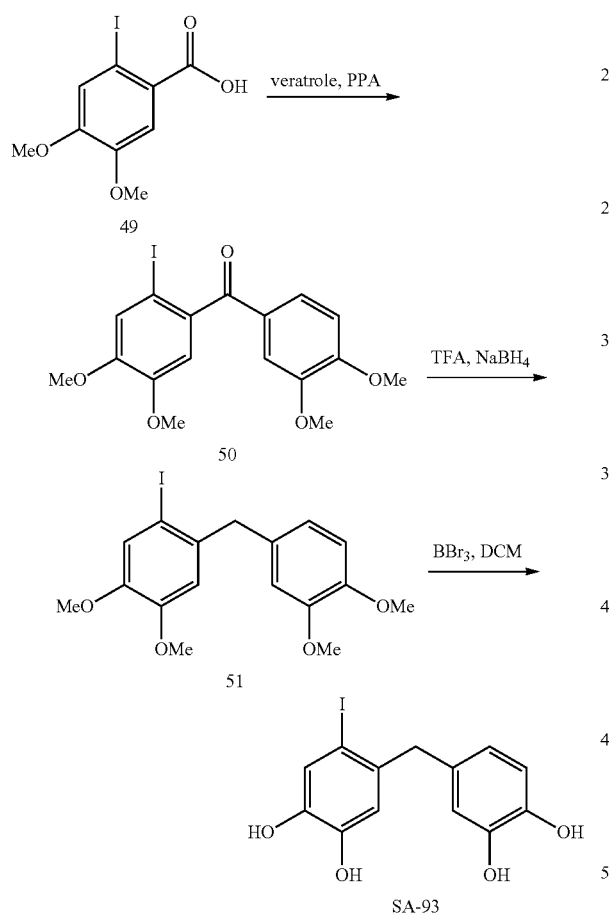

2-Iodo-4,5-dimethoxybenzoic acid (49) (2.76 g, 9.0 mmol), veratrole (1.20 g, 8.6 mmol), and 50 g of polyphosphoric acid (PPA) were heated to 90° C. for 15 mm. An additional 0.30 g (2.1 mmol) of veratrole was added. The reaction mixture turned a deep orange color during the reaction. The crude mixture was treated with 600 mL of ice water, sonicated, and the resultant crude product was filtered as a brownish solid (1.55 g, 40% yield). This product 50 was used without further purification.

Benzophenone 50 (1.55 g, 3.6 mmol) in 10 mL DCM was added to a solution of 2.00 g NaBH$_4$ (26 mmol) in 10 mL of TFA. Caution: the reaction between NaBH$_4$ and TFA is extremely exothermic with the evolution of hydrogen gas. It is recommended that: (1) an ice bath be used when the addition is occurring and (2) NaBH$_4$ pellets are used as opposed to powder. The mixture was stirred 16 h, quenched with 50 mL of water, and diluted with 15 mL of DCM. The aqueous layer was made basic with 10 N NaOH, the layers were separated, the aqueous layer extracted once with 25 mL DCM, and the organic layer dried with Na$_2$SO$_4$ and concentrated. The crude product consisted of the iodo compound 51 and the des-iodo 46. The products practically co-elute when Flash 40+M column chromatography is used, so the crude was purified using PTLC with 0.4% ethyl acetate as the eluent and eluting the PTLC plates several times to give 0.30 g (20% yield) of 51 as a thick, yellow oil.

$^1$H NMR (CDCl$_3$, δ) 6.80 (d, J=8.0 Hz, 1H), 6.74-6.64 (overlapping peaks, 4H), 3.98 (s, 2H), 3.85 (bs, 9H), 3.75 (s, 3H).

$^{13}$C NMR (CDCl$_3$, δ) 149.5, 149.0, 148.1, 147.6, 136.3, 132.6, 121.8, 120.8, 113.1, 112.3, 111.3, 88.8, 56.2, 55.9, 45.6.

Iodide 51 (0.150 g, 0.36 mmol) in 40 mL of DCM was cooled to −78° C. and treated with BBr$_3$ (0.75 g, 3 mmol) neat. The mixture was stirred 2 h, allowed to warm to ~23° C., stirred 3 h more, quenched with water, extracted with 20 mL ethyl acetate, and the organic dried and concentrated. The crude, concentrated product was precipitated with DCM, and filtered to give 0.022 g of SA-93 (17% yield).

$^1$H NMR (DMSO-d$_6$, δ) 6.62-6.52 (overlapping peaks, 3H), 6.50 (d, J=1.9 Hz, 1H), 6.41 (dd, J=2.0, 8.2 Hz, 1H), 3.54 (s, 2H), 4.5-3.5 (broad peak, 4H, "—OH")

Example 30

Synthesis of SA-94 and SA-98

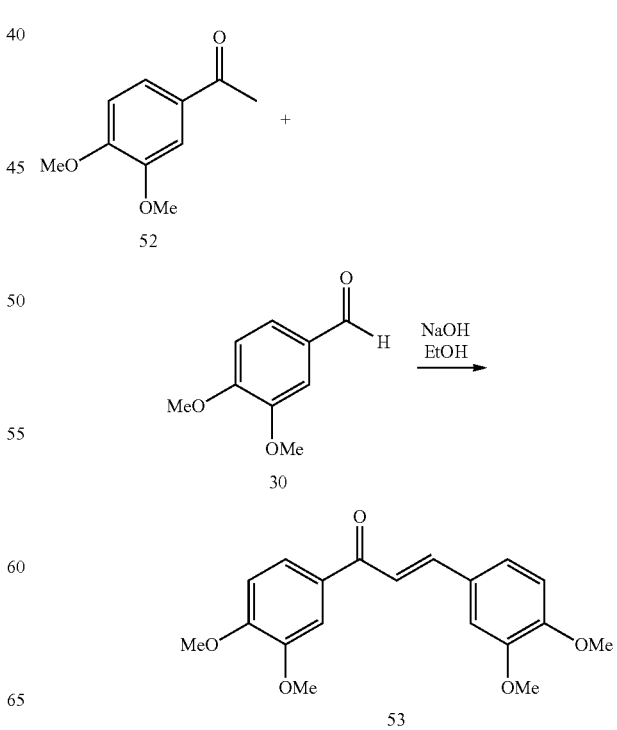

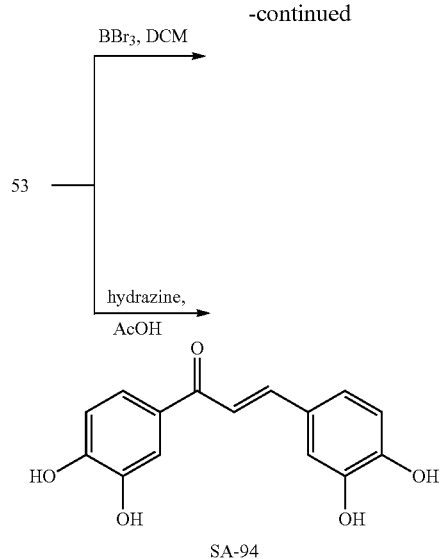

A solution of 53 (0.082 g, 0.25 mmol) in 1.5 mL of acetic acid was treated with 0.5 mL of hydrazine hydrate and heated to 135° C. for 2 h and 140° C. for 1 h. The yellow color of the starting material gradually discharged throughout the course of the reaction. The crude reaction mixture was poured into 20 mL of water, extracted with 10 mL of ethyl acetate twice. The combined organic layers were washed twice with 20 mL of water, dried, and concentrated to give 0.058 g (61% yield) of 54 as a clear oil that was not purified further.

A solution of 54 (0.056 g, 0.59 mmol) in 20 mL of DCM was cooled to −78° C., and treated with BBr$_3$ (1.025 g, 4.1 mmol) in 5 mL of DCM. The mixture was stirred for 3 h at −78° C., stirred for 1 h at ~0° C., and quenched with water. The resultant mixture was extracted with 100 mL of ethyl acetate, and the organic layer was dried and concentrated to give the crude product which was taken up in 2 mL of ethyl acetate, treated with 2 mL of hexanes, and treated with 50 mL of DCM. The precipitated product SA-98 (0.019 g, 40% yield) was collected by filtration and dried to give an off-white powder.

$^1$H NMR (DMSO-d$_6$) 9.4 (bs, 1H), 9.2 (bs, 1H), 8.9 (bs, 1H), 8.8 (bs, 1H), 7.26 (d, J=2.2 Hz, 1H), 6.98 (dd, J=2.2, 8.4 Hz, 1H), 6.77 (d, J=8.2 Hz, 1H), 6.64 (d, J=8.4 Hz, 1H), 6.52 (d, J=2.2 Hz, 1H), 6.44 (dd, J=2.2, 8.0 Hz, 1H), 5.32 (dd, J=3.6, 11.0 Hz, 1H), 3.4 (m, 1H), 3.22 (m, 1H), 2.24 (s, 3H).

HRMS, Calculated for C$_{17}$H$_{17}$N$_2$O$_5$ (M+H)$^+$ 329.1137. found 329.1125.

Example 31

Synthesis of SA-95

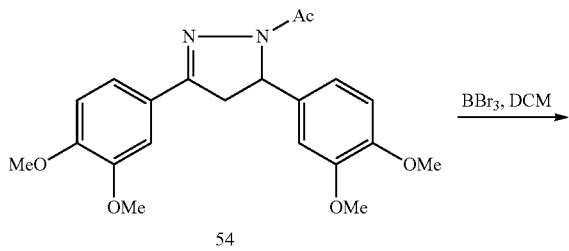

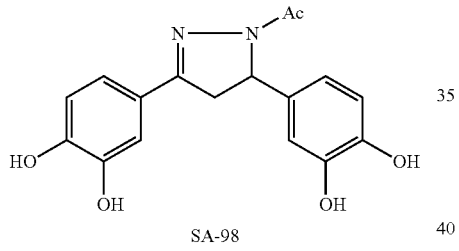

A mixture of 3′,4′-dimethoxyacetophenone (52) (0.54 g, 3 mmol) and 3,4-dimethoxybenzaldehyde (0.51 g, 3.06 mmol) in 15 mL of absolute ethanol was treated with 1.75 g of NaOH, sonicated for 10 min, then stirred overnight. The resultant mixture was cooled to 0° C., filtered, and washed with 4° C. ethanol to obtain a yellow solid that was dried to give 0.88 g of 53 (89% yield).

$^1$H NMR (CDCl$_3$, δ) 7.76 (d, J 15.4 Hz, 1H), 7.68 (dd, J 2.0, 8.4 Hz, 1H), 7.62 (d, J=2.0 Hz, 1H), 7.40 (d, J 15.4 Hz, 1H), 7.19 (dd, J=2.0, 8.4 Hz, 1H), 6.93 (d, J=8.0 Hz, 1H), 6.90 (d, J=8.0 Hz, 1H).

A solution of 53 (0.14 g, 0.43 mmol) was dissolved in 40 mL of DCM, cooled to −78° C., and BBr$_3$ (0.98 g, 3.9 mmol) in 4 mL of DCM was added. The mixture was allowed to warm to 0° C. over 2 h, and then immediately warmed to 23° C. The mixture was stirred 2 h, quenched with 20 mL of water, and extracted with 100 mL of ethyl acetate. The organic layer was dried, concentrated until ~5 mL remained, and treated with 30 mL of DCM. A deep purple solid precipitated from the solution. This solid was filtered, and dried to a yellow-green solid in the dark to give 0.068 g (59% yield) of SA-94.

$^1$H NMR (DMSO-d$_6$) 10.5-8.0 (bs, 4H), 7.57-7.47 (m, 2H), 7.49 (s, 2H), 7.20 (bs, 1H), 7.12 (m, 1H), 6.84 (d, J=8.4 Hz, 1H), 6.79 (d, J=8.6 Hz, 1H).

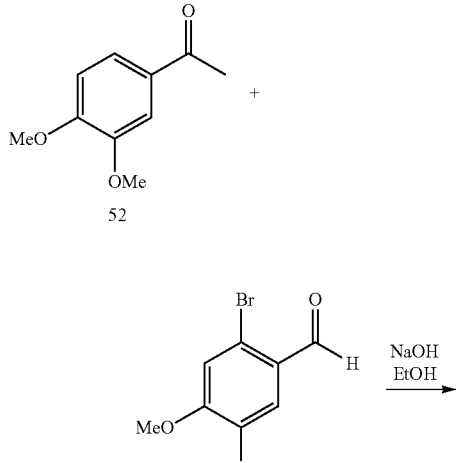

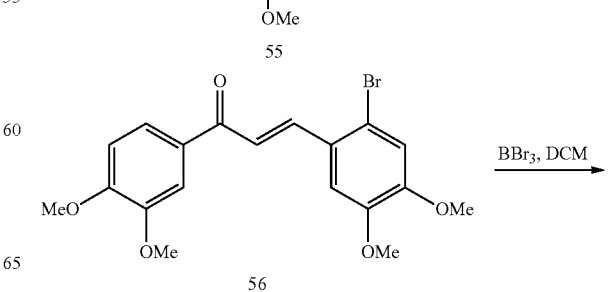

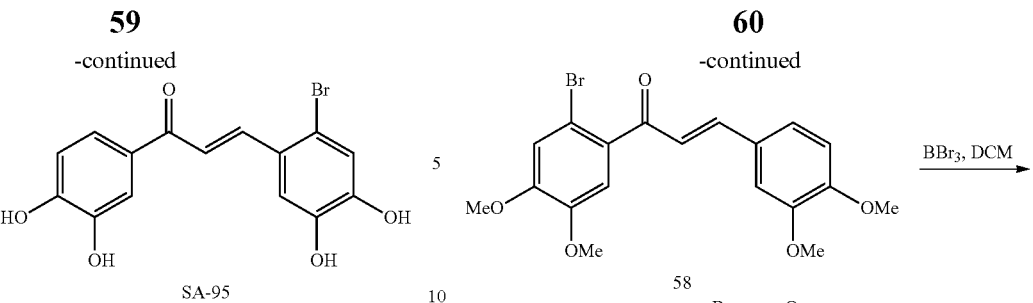

SA-95

A mixture of 3',4'-dimethoxyacetophenone (52) (2 mmol, 0.36 g) and 6-bromoveratraldehyde (55) (2 mmol, 0.49 g) in 15 mL of ethanol was treated with 1 g of NaOH and 0.015 g (2.78 mmol) of NaOMe. The mixture was stirred at 23° C. for 18 h, cooled to 4° C., and the resultant yellow solid filtered to give the bromochalcone 56 as a yellow solid (0.68 g, 83% yield).

$^1$H NMR (CDCl$_3$, δ), 8.07 (d, J=15.6 Hz, 1H), 7.75 (m, 1H), 7.67 (d, J=1.8 Hz, 1H), 7.38 (m, 1H), 7.22 (s, 1H), 7.12 (s, 1H), 6.95 (d, J=8.2 Hz, 1H), 3.98-3.94 (overlapping singlets, 12H).

A mixture of bromochalcone 56 (0.20 g, 0.49 mmol) in 30 mL of DCM was cooled to −78° C. and treated with BBr$_3$ (0.72 g, 2.88 mmol) in 4 mL of DCM. The mixture was stirred at −78° C. for 2.5 h, warmed gradually to 0° C. over 1 h, warmed to 23° C., and stirred an additional 1 h. The reaction was quenched with 20 mL of water, and the mixture extracted with 50 mL of ethyl acetate. The ethyl acetate layer was washed once with 20 mL of brine, dried concentrated to 2 mL, and treated with 50 mL of DCM. The product was filtered and dried to get SA-95 as a reddish solid (0.056 g, 33% yield).

$^1$H NMR (dmso-d$_6$) 10.2 (bs, 1H), 9.8 (bs, 1H), 9.3 (bs, 2H), 7.81 (d, J=15.4 Hz, 1H), 7.61 (d, J=2.2 Hz, 1H), 7.56-7.49 (overlapping peaks, 3H), 7.05 (s, 1H), 6.86 (d, J=8.2 Hz, 1H).

Example 32

Synthesis of SA-96

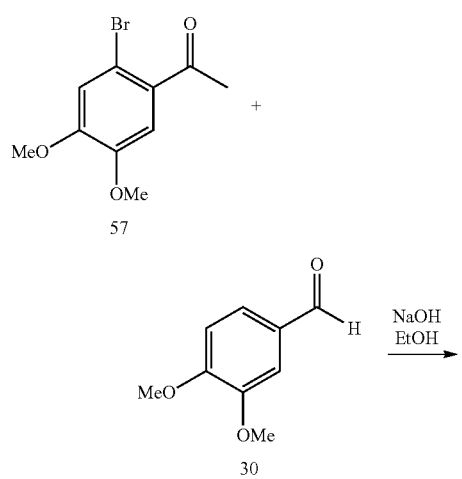

A mixture of 2'-bromo-4',5'-dimethoxyacetophenone (57) (0.390 g, 1.5 mmol) and 3,4 dimethoxybenzaldehyde (30) (0.310 g, 1.9 mmol) in 10 mL of ethanol was treated with 0.75 g of NaOH. The mixture was inverted ten times to thoroughly mix the starting materials, sonicated 5 mm, allowed to stand 2 h, and sonicated 5 min again. A yellow precipitate resulted, and this was filtered and dried to give bromochalcone 58 as a light yellow solid (0.482 g, 79% yield).

$^1$H NMR (CDCl$_3$, δ) 7.41 (d, J=2.2 Hz, 1H), 7.39-7.34 (m, 3H), 7.25 (s, 1H), 7.17 (d, J=16.0 Hz, 1H), 7.10 (s, 1H), 7.00 (d, J=8.4 Hz, 1H), 3.86-3.81 (overlapping singlets, 12H). $^{13}$C NMR (CDCl$_3$, δ) 194.0, 151.9, 151.1, 149.5, 148.5, 146.6, 133.4, 127.6, 124.6, 124.0, 116.5, 112.8, 112.1, 111.5, 110.2, 56.6, 56.4, 56.2, 56.1.

A mixture of bromochalcone 58 (0.27 g, 0.66 mmol) in 30 mL of DCM was cooled to −78° C., and treated with 1.25 g (5 mmol) of BBr$_3$ in 5 mL of DCM. The mixture was stirred at −78° C. for 3 h, warmed immediately to 23° C., stirred at 23° C. for 1 h, quenched with 20 mL of water, and extracted with 125 mL of ethyl acetate. The organic layer was dried and concentrated to 1 mL. The concentrate was treated with an excess of DCM to precipitate a purplish-red solid that was filtered and dried to give SA-96 as a reddish-brown solid (0.036 g, 16% yield).

$^1$H NMR (DMSO-d$_6$, δ) 7.26 (d, J=16.0 Hz, 1H), 7.09 (bs, 1H), 7.05-6.86 (overlapping peaks, 4H), 6.77 (d, J=8.2 Hz, 1H).

Example 33

Synthesis of SA-97

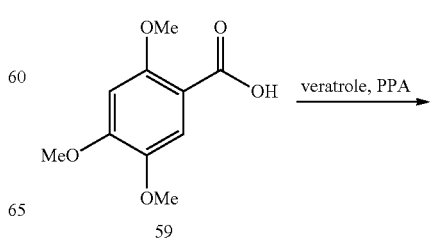

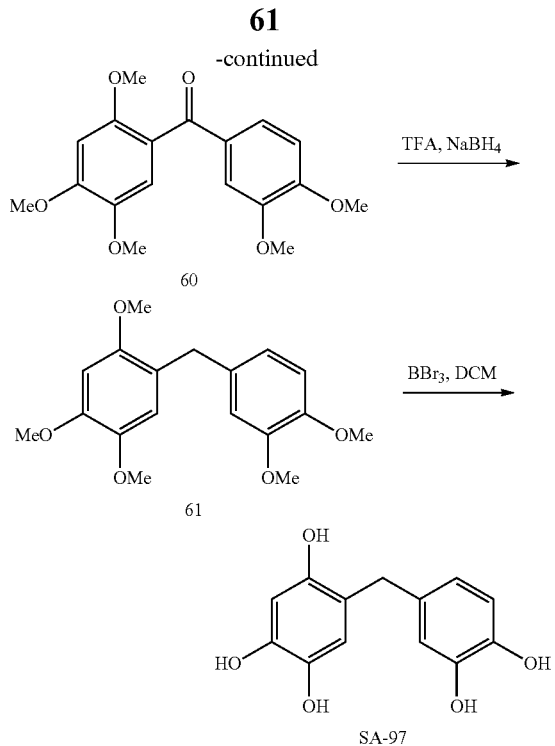

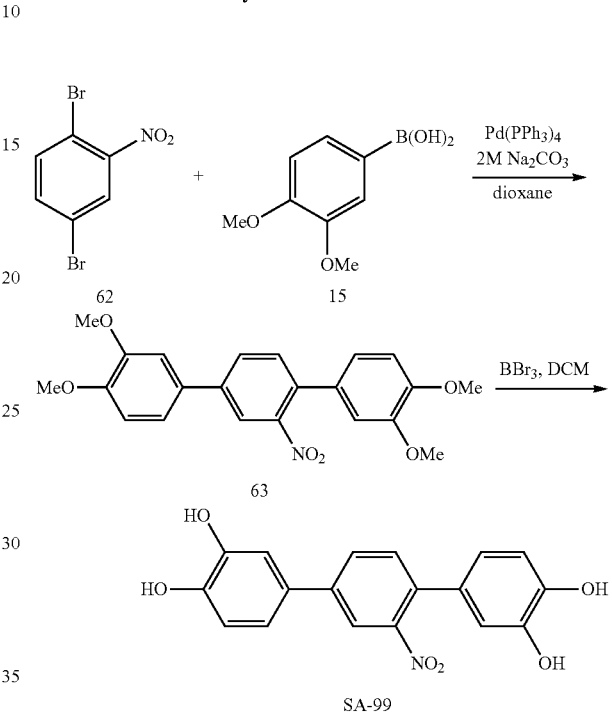

ethyl acetate, precipitated with DCM, cooled to −20° C., and filtered to give SA-97 as a white solid (0.93 g, 46% yield).

$^1$H NMR (DMSO-d$_6$) 8.63-8.29 (bs, 4H), 6.58 (d, J=7.8 Hz, 1H), 6.52 (d, J=2.0 Hz, 1H), 6.40 (dd, J=2.0, 8.0 Hz, 1H), 6.29 (s, 1H), 6.26 (s, 1H), 3.50 (s, 2H).

Example 34

Synthesis of SA-99

A mixture of 2,4,5-trimethoxybenzoic acid (59) (1.06 g, 5 mmol), veratrole (0.69 g, 5 mmol), and 10 g of PPA was heated with a heat gun and stirred with a stirring rod for 20 min. Water (100 mL) was added to the reaction mixture and the resultant mixture was cooled to 4° C. and stirred with a stirring rod for 20 min. The water was decanted and the resultant grey, gummy solid was taken up in a hot solution 20 mL of reagent alcohol and 10 mL of water. The mixture was cooled and filtered to give 0.43 g of orange crystals. Water (40 mL) was added to the filtrate and the resultant orange solid was filtered to give 0.72 g of amorphous orange solid. Both fractions were the desired 60 (1.15 g, 69% yield).

A mixture of benzophenone 60 (0.93 g, 2.9 mmol) in 20 mL of DCM was added to 0.92 g of NaBH$_4$ (24.3 mmol) in 10 mL of TFA. Caution: the reaction between NaBH$_4$ and TFA is extremely exothermic with the evolution of hydrogen gas. It is recommended that: (1) an ice bath be used when the addition is occurring and (2) NaBH$_4$ pellets are used as opposed to powder. The mixture was stirred for 6 h, and an additional portion of NaBH$_4$ (0.53 g, 14.0 mmol) was added. The mixture was stirred 20 h, diluted with 50 mL of DCM and 50 mL of water, and the aqueous layer made basic with NaOH. The layers were separated, and the aqueous layer was extracted once with 50 mL of DCM. The organic layers were combined, dried, and concentrated to give a yellow oil that was purified by Flash 40+M chromatography (Biotage) to give 61 as a pale yellow, thick oil (0.63 g, 71% yield).

$^1$H NMR (CDCl$_3$, δ) 6.83-6.76 (overlapping peaks, 3H), 6.66 (s, 1H), 6.57 (s, 1H), 3.91-3.86 (overlapping singlets, 11H), 3.83 (s, 3H), 3.79 (s, 3H).

A mixture of pentamethoxy compound 61 (0.262 g, 0.82 mmol) in 30 mL of DCM at −78° C. was treated with BBr$_3$ (2.00 g, 8 mmol) in 8 mL of DCM. The resultant mixture was stirred at −78° C. 1 h, warmed to 23° C. immediately, stirred at 23° C. for 4 h, quenched with 20 mL of water and extracted with 100 mL of ethyl acetate. The ethyl acetate layer was concentrated to dryness, taken up in approximately 0.5 mL of A mixture of dibromide 62 (0.562 g, 2 mmol), boronic acid 15 (0.910 g, 5 mmol), 20 mL of dioxane, and 24 mL of 2 M Na$_2$CO$_3$ (aqueous) was degassed by nitrogen purge. Then Pd(PPh$_3$)$_4$ (0.12 g, 0.10 mmol) was added. The resultant mixture was refluxed 20 h, diluted with 50 mL of water, and extracted three times with 50 mL of ethyl acetate. The combined organic layers were washed once with 50 mL of water, dried, and concentrated to give the crude product. This was purified by Flash 40+M chromatography (Biotage) using gradient ethyl acetate in hexanes as the eluent to give 63 as a yellow solid (0.288 g, 36% yield).

$^1$H NMR (CDCl$_3$, δ), 7.94 (d, J=1.8 Hz, 1H), 7.75 (dd, J=1.8, 8.0 Hz, 1H), 7.47 (d, i=8.0 Hz, 1H), 7.17 (dd, J=2.2, 8.2 Hz, 1H), 7.10 (d, J=2.0 Hz, 1H), 6.96 (d, J=8.0 Hz, 1H), 6.90-6.85 (overlapping peaks, 3H), 3.95 (s, 3H), 3.92 (s, 3H), 3.90 (s, 3H), 3.87 (s, 3H).

$^{13}$C NMR (CDCl$_3$, δ) 149.9, 149.7, 149.6, 149.3, 149.1, 141.1, 133.9, 132.2, 131.2, 130.0, 129.5, 121.8, 120.5, 119.6, 111.7, 111.4, 111.2, 110.1, 56.11, 56.05, 56.0, 55.9.

A solution of 63 (0.062 g, 0.16 mmol) in 25 mL DCM was cooled to −78° C., treated with BBr$_3$ (1.125 g, 4.5 mmol) in 6 mL of DCM, stirred 2.5 h at −78° C., warmed to 23° C., stirred at −23° C. for 1.5 h, quenched with 20 mL water, and extracted once with 100 mL of ethyl acetate. The ethyl acetate layer was dried and concentrated to 3 mL and precipitated with excess DCM. The precipitate was filtered and dried to give SA-99 as a yellow solid (0.037 g, 70% yield).

$^1$H NMR (DMSO-d$_6$) 9.17-9.11 (bs, 411), 7.96 (d, J=1.6 Hz, 1H), 7.83 (dd, J=2.2, 8.2 Hz, 1H), 7.49 (d, J=8.0 Hz, 1H), 7.14 (bs, 1H), 7.08 (d, J=8.4 Hz, 1H), 6.88-6.79 (overlapping peaks, 2H), 6.72 (d, J=2.2 Hz, 1H), 6.63 (dd, J=2.0, 8.2 Hz, 1H), HRMS Calculated for $C_{18}H_{13}NO_6Na$ $(M+Na)^+$ 362.0641. Found 362.0645.

Example 35

Synthesis of SA-108

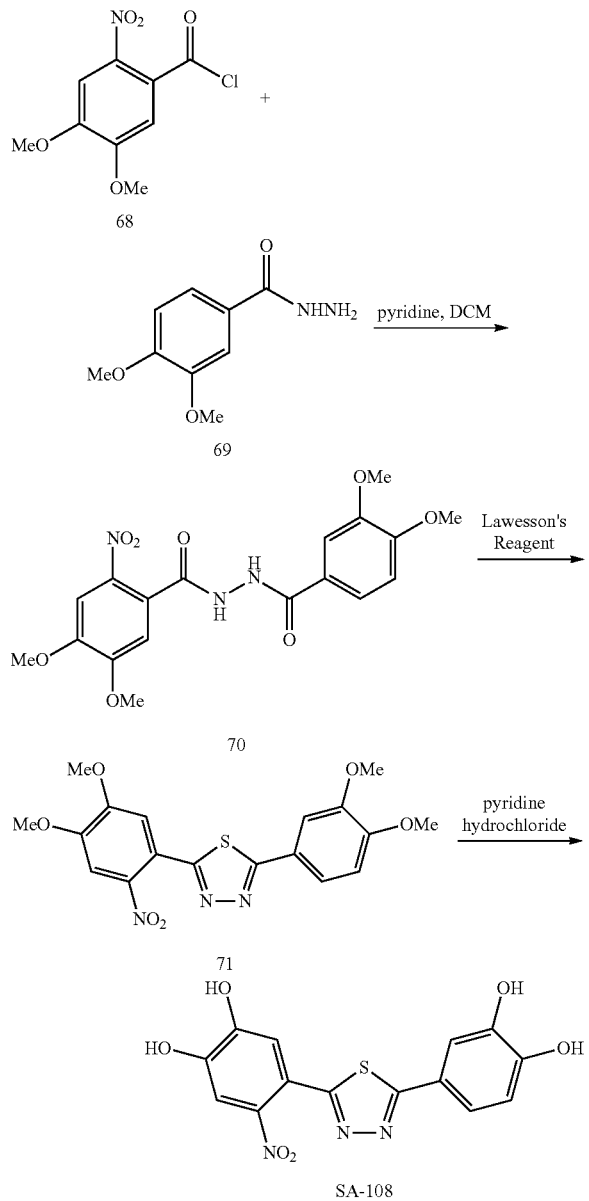

To 1.00 g (4.07 mmol) of acid chloride 68 in 25 mL of DCM at 0° C. was added 5 mL of pyridine. The mixture was stirred 3 min, and 0.76 g (3.87 mmol) of known hydrazide 69 was added at once. The mixture was gradually allowed to warm to 21-23° C. and stirred at this temperature for 16 h. The mixture was concentrated, treated with 10 mL of ethanol, warmed to reflux, and diluted with 30 mL of water. After returning the mixture to reflux, ethanol was added gradually until a solution formed. The solution was allowed to cool, and the precipitated light yellow solid was collected and dried to give 0.498 g (1.24 mmol, 32% yield) of 70.

$^1$H NMR (CDCl$_3$ and MeOD, δ) 7.54 (s, 1H), 7.45 (dd, J=2.2, 8.4 Hz, 1H), 7.39 (d, J=1.8 Hz), 7.16 (s, 1H), 6.82 (d, J=8.4 Hz, 1H), 3.98-3.73 (overlapping singlets+residual H$_2$O peak, 12H).

A mixture of 0.398 g (1 mmol) of 70 and 0.452 g (1.11 mmol) of Lawesson's reagent in 50 mL of THF were refluxed for 16 h. The mixture was concentrated and purified by PTLC using 10% EtOAc in DCM as the elutent to give 0.255 g (0.62 mmol, 62% yield) 71 as a bright yellow solid.

$^1$H NMR (DMSO-d$_6$) 7.77 (s, 1H), 7.60-7.58 (overlapping peaks, 2H), 7.40 (s, 1H), 7.15 (d, J=8.8 Hz, 1H), 3.97 (s, 3H), 3.95 (s, 3H), 3.89 (s, 3H), 3.87 (s, 3H).

A mixture of 0.100 g (0.24 mmol) of 71 in 5 g of pyridine hydrochloride was heated to 200° C. for 30 min. The mixture was cooled, treated with 30 mL of water, and filtered. The resultant solid was recrystalized from aqueous methanol to yield 0.016 g of a brown solid as SA-108. The product is only sparingly soluble in DMSO-d$_6$, and insoluable in other deuterated solvents or solvent mixtures.

$^1$H NMR (DMSO-d$_6$, δ), 8.79 (s, 1H), 7.80 (bs, 1H), 7.57 (s, 1H), 7.43 (m, 1H), 7.28 (m, 1H), 6.91 (s, 1H), 6.80 (d, J=8.0 Hz, 1H). Example 1—Compounds provided herein bind are potent disruptors/inhibitors of Parkinson's disease α-synuclein fibrils Example 36

Compounds Provided Herein are Potent Disruptors/Inhibitors of Parkinson's Disease α-Synuclein Fibrils The compounds were found to be potent disrupters/disaggregators of α-synuclein fibrils. In this set of studies, the efficacy of certain compounds provided herein to cause a disassembly/disruption/disaggregation of pre-formed fibrils of Parkinson's disease (i.e. consisting of α-synuclein fibrils) was analyzed. For the studies described below in Parts A and B, 69 μM of α-synuclein (rPeptide, Bogart, Calif.) was first incubated at 37° C. for 4 days in 20 mM sodium acetate buffer at pH 4 with circular shaking (1,300 rpm) to cause α-synuclein aggregation and fibril formation.

Part A: Thioflavin T Fluorometry Data

In one study, Thioflavin T fluorometry was used to determine the effects of the compounds on α-synuclein fibrils. In addition to test compounds, this experiment included a positive control compound and a negative control compound for reference. In this assay Thioflavin T binds specifically to fibrillar amyloid, and this binding produces a fluorescence enhancement at 485 nm that is directly proportional to the amount of fibrils formed. The higher the fluorescence, the greater the amount of fibrils formed (Naki et al., Lab. Invest. 65:104-110, 1991; Levine III, Protein Sci. 2:404-410, 1993; Amyloid: Int. J. Exp. Clin. Invest. 2:1-6, 1995).

Following initial α-synuclein fibrilization as described above, 6.9 μM α-synuclein was incubated at 37° C. for 2 days with shaking (1,300 rpm), either alone, or in the presence of one of the compounds (at test compound:α-synuclein molar ratios of 50:1, 10:1, 5:1, 1:1, 0.5:1, 0.1:1, 0.05:1 and 0.01:1) in phosphate-buffered saline, pH 7.4+0.02% sodium azide. Following 2 days of co-incubation, 50 μl of each incubation mixture was transferred into a 96-well microtiter plate containing 150 μl of distilled water and 50 μl of a Thioflavin T solution (i.e. 500 μM Thioflavin T in 250 μM phosphate buffer, pH 6.8). The final concentration of Thioflavin T reagent is 100 μM in 50 μM phosphate buffer, pH 6.8. The fluorescence was read at 485 nm (444 nm excitation wavelength) using an ELISA plate fluorometer after subtraction with buffer alone or compound alone, as blank.

The results of the 2-day incubations are presented below. For each compound, the % inhibition of Thioflavin T fluorescence (i.e. the decrease compared to control reactions containing α-synuclein alone) was plotted against the log of the concentration of the test compound (expressed as mole ratio relative to α-synuclein). Where possible, the effective concentration of SA compound that yields 50% of maximal % decrease of Thioflavin T fluorescence ($EC_{50}$) was calculated from the sigmoidal shaped dose response curve. The compounds (SA-52, SA-53, SA-54, SA-55, SA-57, SA-58, SA-59, SA-61, SA-62, SA-63, SA-64, SA-66, SA-67, SA-68, SA-69, SA-70, SA-72, SA-73, SA-93, SA-94, SA-95, SA-96, SA-97, SA-98 and SA-99 and positive reference compound #1) all caused a dose-dependent and extensive disruption/disassembly of preformed α-synuclein fibrils (Table 1). For example, compound SA-57 caused a significant ($p<0.01$ relative to α-synuclein alone) nearly complete inhibition (97-100%) when used at test compound:α-synuclein molar ratios ≥5:1 and a significant 83% inhibition when used at a test compound:α-synuclein molar ratio of 1:1 (FIG. 1), whereas the negative reference compound showed no significant inhibition of Thioflavin T fluorescence at any of the concentrations tested (not shown). The $EC_{50}$ of SA-57 for inhibition of Thioflavin T fluorescence was determined to be 0.23 moles of test compound per mole of α-synuclein (Table 1). For the compounds described here that caused a dose-dependent disruption/disassembly of α-synuclein fibrils, the maximum % inhibition ranged from 76-100% and the $EC_{50}$ values ranged from 0.08-4.3 moles of test compound:α-synuclein, with most compounds showing highly potent effects (i.e. $EC_{50}<1$ mole of test compound:α-synuclein) in this assay.

This study indicated that the compounds provided herein are potent disrupters/dissaggregators of Parkinson's disease α-synuclein fibrils, and usually exert their effects in a dose-dependent manner.

TABLE 1

SA compounds disrupt/disaggregate α-synuclein aggregates as measured by Thioflavin T fluorometry.

| SA # | $EC_{50}$ (mole ratio) | Max % Decrease |
|---|---|---|
| 52 | 0.28 | 99 |
| 53 | 0.17 | 100 |
| 54 | 0.74 | 98 |
| 55 | 0.08 | 92 |
| 57 | 0.23 | 100 |
| 58 | 0.19 | 100 |
| 59 | 0.58 | 96 |
| 61 | 0.10 | 100 |
| 62 | 1.09 | 95 |
| 63 | 0.86 | 100 |
| 64 | 0.39 | 100 |
| 66 | 0.69 | 100 |
| 67 | 4.3 | 76 |
| 68 | 0.77 | 100 |
| 69 | 0.73 | 88 |
| 70 | 0.17 | 100 |
| 72 | 0.12 | 100 |
| 73 | 0.52 | 100 |
| 93 | 0.16 | 100 |
| 94 | 0.15 | 100 |
| 95 | 0.16 | 100 |
| 96 | 0.14 | 100 |
| 97 | 0.16 | 99 |
| 98 | 0.65 | 100 |
| 99 | 0.65 | 100 |

TABLE 1-continued

SA compounds disrupt/disaggregate α-synuclein aggregates as measured by Thioflavin T fluorometry.

| SA # | $EC_{50}$ (mole ratio) | Max % Decrease |
|---|---|---|
| Positive Reference #1 | 0.24 | 100 |
| Negative Reference | not determined | 0 |

Part B: Congo Red Binding Data

In the Congo red binding assay, the ability of a given test compound to alter α-synuclein aggregate binding to Congo red is quantified. In this assay Congo red binds specifically to fibrillar amyloid, and this binding is directly proportional to the amount of fibrils formed. Following initial α-synuclein fibrilization as described above, α-synuclein aggregates and test compounds were incubated for 2 days and then vacuum filtered through a 0.2 μm filter. The amount of α-synuclein retained in the filter was then quantitated following staining of the filter with Congo red. After appropriate washing of the filter, any lowering of the Congo red color on the filter in the presence of the test compound (compared to the Congo red staining of the amyloid protein in the absence of the test compound—i.e. α-synuclein alone) was indicative of the test compound's ability to diminish/alter the amount of aggregated and congophilic α-synuclein and thus cause disassembly/disruption/disaggregation of α-synuclein fibrils.

Figure 2:
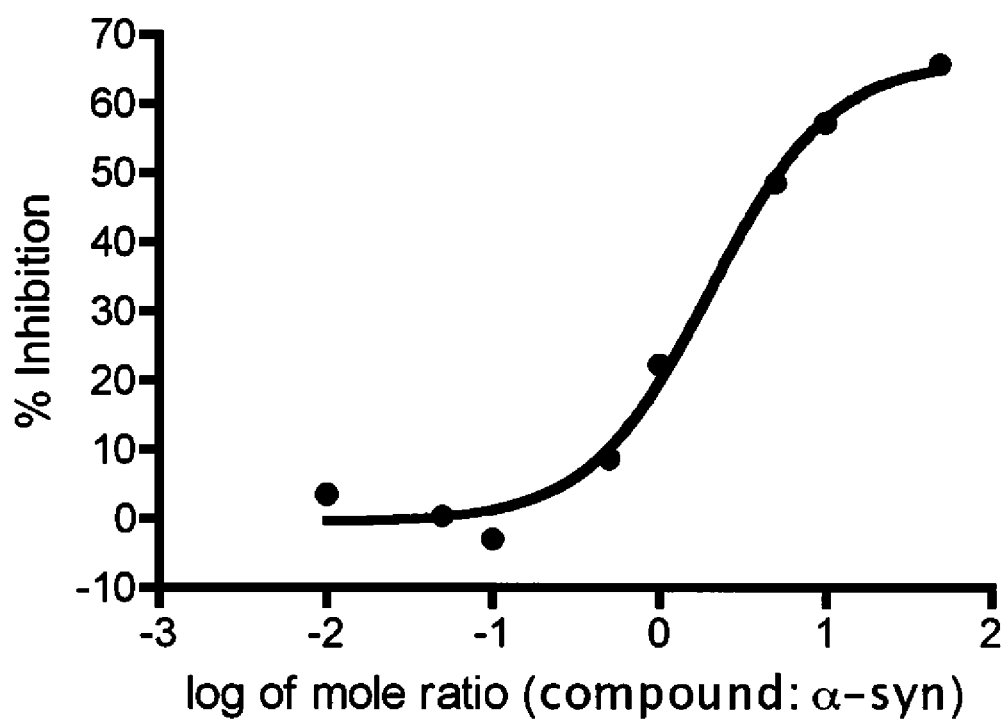
FIG. 2 is a graph illustrating that a compound of the invention causes the dose-dependent inhibition of of α-synuclein aggregation and fibril formation as assessed by Congo Red binding.

In one study, the ability of α-synuclein fibrils to bind Congo red in the absence or presence of increasing amounts of the compounds provided herein, including a positive and a negative reference compound (at test compound:α-synuclein molar ratios of 50:1, 10:1, 5:1, 1:1, 0.5:1, 0.1:1, 0.05:1, 0.01:1) was determined. The results of 2-day incubations are presented in Table 2 below. Whereas the negative reference compound caused no significant inhibition of α-synuclein fibril binding to Congo red at all concentrations tested (not shown), the test compounds caused a dose-dependent inhibition of α-synuclein binding to Congo red. For example, compound SA-57 caused a significant ($p<0.01$) inhibition (66%) when used at a test compound:α-synuclein molar ratio of 50:1 and a significant 49% inhibition when used at a test compound:α-synuclein molar ratio of 5:1 (FIG. 2). The $EC_{50}$ of SA-57 for inhibition of Congo Red binding was determined to be 2.0 moles of test compound per mole of α-synuclein (Table 2). For the compounds described here that caused a dose-dependent disruption/disassembly of α-synuclein fibrils, the maximum % inhibition ranged from 25-94% and the $EC_{50}$ values ranged from 1.0-15.9 moles of test compound per mole of α-synuclein. Taken together, the results of this study indicated that compounds of this invention disrupt/disaggregate/disassemble α-synuclein aggregates as indicated by their ability to inhibit Parkinson's disease type α-synuclein fibril binding to Congo red, and usually exert their effects in a dose-dependent manner.

TABLE 2

SA compounds disrupt/disaggregate α-synuclein fibrils/aggregates as measured by Congo Red binding assay.

| SA # | $EC_{50}$ (mole ratio) | Max % Decrease |
|---|---|---|
| 52 | 10.7 | 68 |
| 53 | 6.8 | 75 |
| 54 | 15.9 | 57 |
| 55 | 4.5 | 38 |
| 57 | 2.0 | 66 |
| 58 | 1.9 | 94 |

TABLE 2-continued

SA compounds disrupt/disaggregate α-synuclein fibrils/aggregates as measured by Congo Red binding assay.

| SA # | EC$_{50}$ (mole ratio) | Max % Decrease |
|---|---|---|
| 59 | 7.6 | 85 |
| 61 | 2 | 84 |
| 63 | 9.5 | 72 |
| 64 | 2.3 | 85 |
| 66 | 2.2 | 48 |
| 67 | 6.8 | 25 |
| 68 | 6.4 | 60 |
| 69 | 14.2 | 39 |
| 70 | 3.4 | 88 |
| 72 | 2.9 | 29 |
| 73 | 1.1 | 35 |
| 93 | 1.9 | 62 |
| 94 | 4.5 | 65 |
| 95 | 4.5 | 64 |
| 96 | 5.1 | 72 |
| 97 | 1.0 | 40 |
| 98 | 10.1 | 44 |
| 99 | 14.2 | 54 |
| Positive Reference #1 | 4.5 | 66 |
| Negative Reference | not determined | 0 |

Example 37

Compounds of this Invention are Potent Disruptors/Inhibitors of α-Synuclein Fibrils and/or Aggregates Associated with Parkinson's Disease Parkinson's Disease is characterized by the accumulation of insoluble intraneuronal aggregates called Lewy Bodies, a major component of which is α-synuclein (reviewed in Dauer et al., Neuron, 39:889-909, 2003). Since autosomal dominant mutations in α-synuclein cause a subset of familial Parkinson's disease, and since these mutations increase the likelihood of α-synuclein to aggregate and form Lewy Bodies, aggregated α-synuclein is proposed to be directly involved in the etiology and disease progression (Polymeropoulos et al., Science 276:1197-1199, 1997; Papadimitriou et al., Neurology 52:651-654, 1999). Structural studies have revealed that intracellular Lewy bodies contain a large proportion of misfolded proteins with a high degree of β-pleated sheet secondary structure. Therefore, since many of the compounds described herein cause disassembly/disruption/disaggregation of α-synuclein aggregates in the in vitro assays (Thioflavin T fluorometry and Congo Red binding assays) described above, studies were also conducted in living cells to determine the efficacy of these compounds to inhibit or prevent α-synuclein aggregation associated with Parkinson's disease.

To test the therapeutic potential of the compounds, two cell-based assays were utilized. In both assays, rotenone is used to induce mitochondrial oxidative stress and cause α-synuclein aggregation. The first assay utilizes the binding of the fluorescent dye Thioflavin S to structures with high β sheet content, including α-synuclein fibrils. Therefore, quantitative assessment of the extent of Thioflavin S-positive staining of fixed cells is used to test the ability of the test compounds to inhibit/prevent or decrease the amount of α-synuclein aggregates relative to cells that were treated with rotenone only. In the second assay, cell viability is assessed using the XTT cytotoxicity assay (Cell Proliferation Assay Kit II, Roche, Mannheim, Germany), which is dependent on intact, functional mitochondria in live cells. Thus, the XTT cytotoxicity assay is used to test the ability of the compounds to ameliorate the mitochondrial toxicity and resulting loss of viability associated with the accumulation of α-synuclein aggregates. These studies are presented in the following examples.

To carry out these studies, a cell culture model was used in which human α-synuclein aggregation is experimentally induced. BE-M17 human neuroblastoma cells stably transfected with A53T-mutant human α-synuclein were obtained. Cell culture reagents were obtained from Gibco/Invitrogen, and cells were grown in OPTIMEM supplemented with 10% FBS, Penicillin (100 units/ml), Streptomycin (100 μg/ml) and 500 μg/ml G418 as previously described (Ostrerova-Golts et al., J. Neurosci., 20:6048-6054, 2000).

Thioflavin S is commonly used to detect aggregated protein structures in situ, including in brain tissue (Vallet et al., Acta Neuropathol., 83:170-178, 1992), and cultured cells (Ostrerova-Golts et al., J. Neurosci., 20:6048-6054, 2000), whereas Thioflavin T is often used as an in vitro reagent to analyze the aggregation of soluble proteins into fibrils enriched in β-pleated sheet structures (LeVine III, Prot. Sci., 2:404-410, 1993). Therefore, Thioflavin S histochemistry was used on cultured cells to detect aggregates containing a high degree of β-pleated structures that formed in response to oxidative stress-inducing agents (in this case rotenone) as previously described, with minor modifications (Ostrerova-Golts et al., J. Neurosci., 20:6048-6054, 2000). Briefly, for these studies cells were grown on Poly-D-Lysine coated glass slide chambers at approximately $4.5$-$5.5 \times 10^4$ cells/cm$^2$. After 16-18 hours, cells were treated with 500 nM or 2 μM rotenone (Sigma) or vehicle (0.05% DMSO) as indicated. Within 15 minutes of rotenone (or vehicle) addition, compounds were added at the indicated concentration, or mock-treatment was performed in which cell culture media only (no compound) was added. Identical treatments were repeated after 48 hours. After an additional 24 hours, cells were fixed for 25 minutes in 3% paraformaldehyde. After a PBS wash and a deionized water wash, the cells were incubated with 0.015% Thioflavin S in 50% ethanol for 25 minutes, washed twice for four minutes in 50% ethanol and twice for five minutes in deionized water and then mounted using an aqueous-based mountant designed to protect against photobleaching. Aggregates that bind to Thioflavin S were detected with a fluorescent microscope using a High Q FITC filter set (480 to 535 nm bandwidth) and a 20× objective lens unless otherwise indicated. Between 8 and 20 (usually 16-18) representative images per condition were selected and imaged using Q Capture software by an experimenter who was blinded to treatment conditions. To assess the amount of Thioflavin S-positive aggregates, the total area per field covered by Thioflavin S-positive inclusions was determined by image analysis and quantitation. For this purpose, background fluorescence that failed to exceed pre-set size or pixel intensity threshold parameters was eliminated using Image Pro Plus software. Spurious, non-cell associated fluorescence was manually removed. Unless indicated otherwise, comparisons between groups were made by comparing mean relative amounts of Thioflavin S-positive inclusions for a given treatment condition (i.e. cells treated with rotenone only versus cells treated with rotenone and test compound at a given concentration). Statistical analyses were performed with GraphPad Prism (GraphPad Inc). Differences between means (two samples) were assessed by the Student's t test. Differences among multiple means were assessed by one-factor ANOVA followed by Dunnett's post hoc test, compared to rotenone only treated cells. The data presented in Table 3 represent statistically significant ($p<0.05$) reductions (reported as percent inhibition) in Thioflavin S fluorescence in cells treated with test compound and rotenone relative to cells treated with rotenone only.

Figure 3:
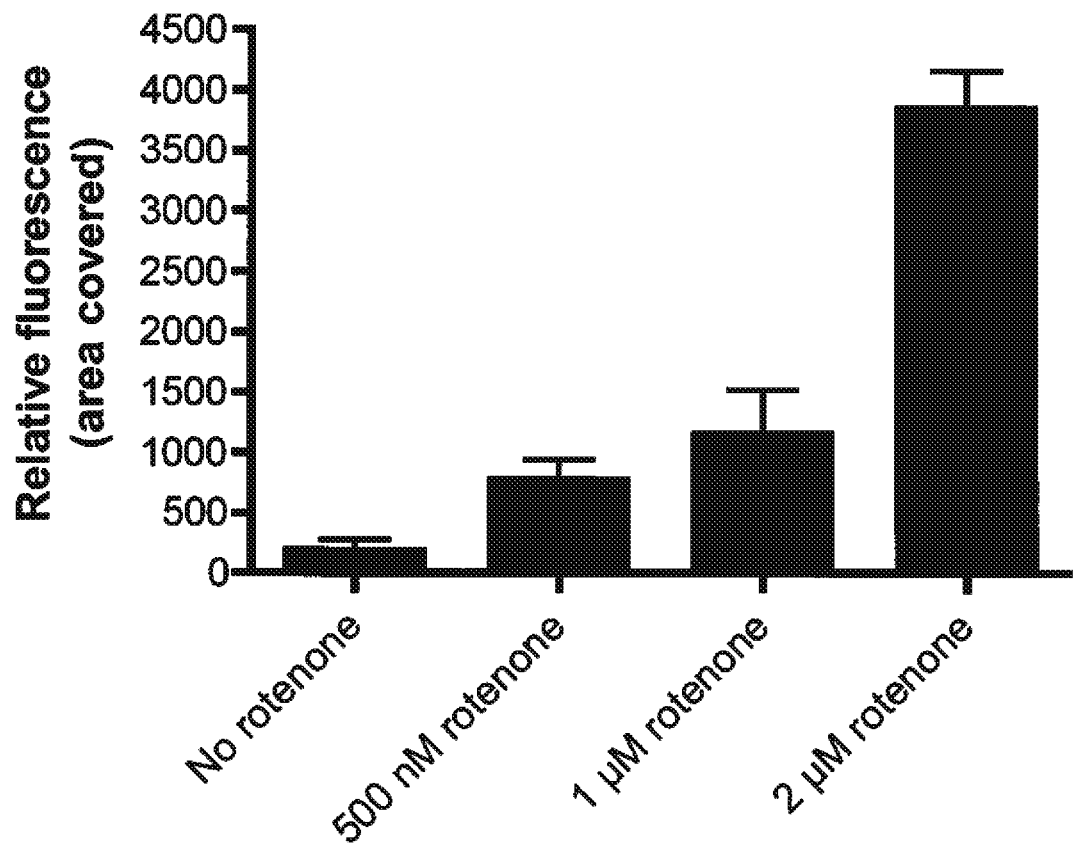
FIG. 3 is a graph illustrating the rotenone dose-dependent increase in Thioflavin S fluorescence in BE-M17 neuroblastoma cells overexpressing A53T-mutant α-synuclein.

To validate the ability of the assay to quantitatively detect aggregates that bind Thioflavin S, staining of BE-M17 cells overexpressing A53T α-synuclein was carried out and the results revealed a rotenone dose-dependent increase in Thioflavin S-positive aggregates relative to vehicle-treated control cells (FIG. 3). Higher magnification images obtained with a 40× objective indicated that the Thioflavin S-positive aggregates were intracellular and cytoplasmic, analogous to the accumulation of intracytoplasmic Lewy bodies that are pathological hallmarks associated with Parkinson's disease (not shown). Quantitation of the area covered by Thioflavin-S-positive aggregates established that 500 nM and 2 μM rotenone were sufficient to induce robust aggregation (FIG. 3) and thus are effective doses to test the ability of compounds to attenuate the formation of these aggregates.

Using the protocol described above, several selected compounds were tested for their ability to reduce, inhibit, prevent or eliminate Thioflavin S-positive aggregates in rotenone-treated BE-M17 cells overexpressing A53T α-synuclein. Examples of results obtained from experiments using these compounds are summarized in Table 4. Many of the compounds tested significantly disrupted, prevented or inhibited α-synuclein aggregation and fibril formation in the presence of rotenone as indicated by a decrease in Thioflavin S-positive inclusions, relative to cells treated with rotenone only. For example, cells treated with 500 nM rotenone only exhibited a robust presence of Thioflavin S-positive aggregates (not shown), whereas addition of 500 nM, 1 μM or 5 μM SA-72 markedly reduced the abundance of these rotenone-induced aggregates by 63%, 65% and 83%, respectively, relative to rotenone only-treated cells (Table 3). Similarly, in cells treated with 2 μM rotenone only, there was a robust presence of Thioflavin S-positive aggregates (not shown), whereas addition of 500 nM or 1 μM SA-72 markedly reduced the abundance of these rotenone-induced aggregates by 67% and 42%, respectively, relative to rotenone only-treated cells (Table 3). Therefore, SA-72 reduced, inhibited, prevented and/or eliminated Thioflavin S-positive aggregates in cells that express human A53T α-synuclein.

In addition to SA-72, compounds SA-52, SA-53, SA-54, SA-58, SA-59, SA-61, SA-62, SA-66, SA-67, SA-68, SA-93, SA-94, SA-95, SA-96 and SA-98, at given concentrations, all showed significant disruption/prevention/inhibition of rotenone-induced Thioflavin S-positive inclusions when tested in a similar fashion. These results are summarized in Table 3.

Taken together, we concluded that the tested compounds SA-52, SA-53, SA-54, SA-58, SA-59, SA-61, SA-62, SA-66, SA-67, SA-68, SA-72 SA-93, SA-94, SA-95, SA-96 and SA-98 effectively and potently reduced, prevented and/or inhibited the formation, deposition and/or accumulation of α-synuclein aggregates in A53T α-synuclein-expressing BE-M17 cells.

TABLE 3

SA compounds prevent/inhibit rotenone-induced Thioflavin S-positive α-synuclein aggregates in cells.

| SA # | Concentration in μM | | Efficacy |
|------|---------|----------|----------|
|      | rotenone | compound | % Inhibition |
| 52 | 2 | 5 | 49 |
| 53 | 2 | 2 | 71 |
| 54 | 0.5 | 0.5 | 80 |
|    | 0.5 | 2 | 83 |
|    | 2 | 1 | 56 |
| 58 | 0.5 | 2 | 68 |
|    | 2 | 2 | 63 |
| 59 | 0.5 | 1 | 69 |
|    | 0.5 | 2 | 76 |
|    | 0.5 | 5 | 56 |
|    | 2 | 1 | 67 |
| 61 | 0.5 | 0.5 | 36 |
|    | 0.5 | 5 | 48 |
| 62 | 0.5 | 0.5 | 81 |
|    | 0.5 | 1 | 55 |
|    | 0.5 | 5 | 85 |
| 66 | 0.5 | 0.5 | 39 |
|    | 0.5 | 1 | 32 |
|    | 0.5 | 5 | 94 |
|    | 2 | 0.5 | 57 |
|    | 2 | 1 | 69 |
| 67 | 0.5 | 0.5 | 75 |
|    | 0.5 | 1 | 48 |
|    | 0.5 | 2 | 92 |
| 68 | 0.5 | 1 | 69 |
|    | 0.5 | 5 | 73 |
|    | 2 | 5 | 44 |
| 72 | 0.5 | 0.5 | 63 |
|    | 0.5 | 1 | 65 |
|    | 0.5 | 5 | 83 |
|    | 2 | 0.5 | 67 |
|    | 2 | 1 | 42 |
| 93 | 2 | 2 | 45 |
| 94 | 0.5 | 2 | 85 |
|    | 2 | 0.5 | 70 |
|    | 2 | 1 | 63 |
| 95 | 0.5 | 0.5 | 73 |
|    | 0.5 | 1 | 98 |
|    | 0.5 | 2 | 90 |
|    | 2 | 0.5 | 95 |
| 96 | 0.5 | 1 | 82 |
|    | 2 | 0.5 | 73 |
|    | 2 | 2 | 81 |
| 98 | 0.5 | 0.5 | 74 |
|    | 2 | 1 | 76 |
| Positive Ref. #1 | 0.5 | 0.5 | 47 |
|    | 0.5 | 1 | 65 |
|    | 0.5 | 2 | 70 |
|    | 2 | 0.5 | 49 |
|    | 2 | 1 | 56 |
|    | 2 | 2 | 60 |
| Negative Ref. | 0.5 | 5 | none detected |
|    | 2 | 5 | none detected |

Example 38

Compounds of this Invention are Neuroprotective Against Rotenone-Induced Cytotoxicity The XTT cytotoxicity assay (Cell Proliferation Assay Kit II) was previously used to demonstrate that A53T α-synuclein potentiates cell death in BE-M17 cells through an oxidative stress-dependent mechanism (Ostrerova-Golts et al., *J. Neurosci.*, 20:6048-6054, 2000). Research has shown that the accumulation of α-synuclein fibrils in Lewy bodies contributes mechanistically to the degradation of neurons in Parkinson's disease and related disorders (Polymeropoulos et al., *Science* 276:2045-2047, 1997; Kruger et al., *Nature Genet.* 18:106-108, 1998). Here, the XTT Cell Proliferation Assay Kit II (hereafter referred to as the XTT assay) was used to measure the ability of compounds to provide neuroprotection against rotenone-induced cytotoxicity. The assay is based on the principle that conversion of the yellow tetrazolium salt XTT to form an orange formazan dye (that absorbs light around 490 nm) occurs only in metabolically active, viable cells. Therefore, light absorbance at 490 nm is proportional to cell viability. For this assay, cells were plated in 96 well tissue culture dishes at $10^4$ cells per well. After 16-18 hours, cells were treated with 500 nM rotenone, or vehicle (0.05% DMSO) as indicated. Approximately 15 minutes after rotenone addition, compounds were added at the indicated concentration. As a control, compounds were added without rotenone (in the presence of 0.05% DMSO vehicle) and resulted in no toxicity at the doses presented. Mock-treatment consisted of cell culture media only (no compound), in the presence or absence of rotenone. After 44-46 hours of treatment, conditioned media was removed and replaced with 100 µl fresh media and 50 µl XTT labeling reaction mixture according to the manufacturer's recommendations. Five to six hours later, the absorbance at 493 nm was measured and corrected for absorbance at the 620 nm reference wavelength. Treatment with 500 nM rotenone decreased viability by 30-40%. Percent inhibition of cell death was calculated as the proportion of the rotenone-induced absorbance (viability) decrease that was eliminated by SA compound treatment.

Figure 4:
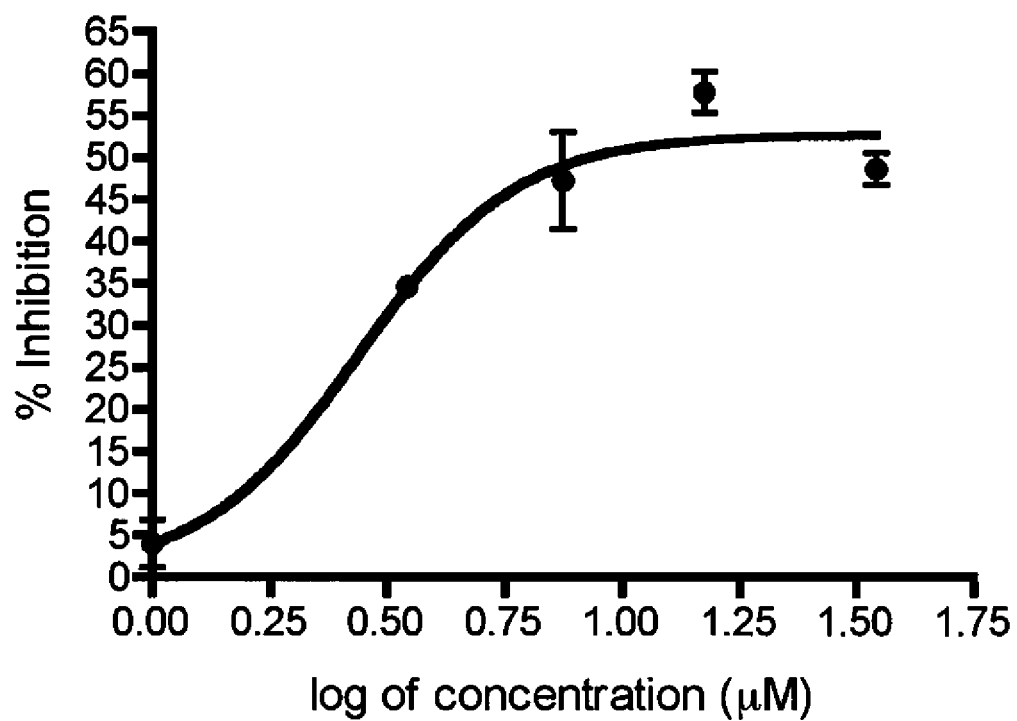
FIG. 4 is a graph illustrating that a compound of the invention causes dose-dependent inhibition of rotenone-induced cell death as assessed by the XTT cell viability assay.

Using the protocol described above, several selected compounds were tested for their ability to provide neuroprotection against the rotenone-induced loss of cell viability (cell death) in A53T α-synuclein-expressing BE-M17 cells. In this series of experiments, there was a 30-40% loss of viability (cell death) in 500 nM rotenone-treated cells, relative to vehicle-treated cells, as expected. However, treatment with the compounds SA-52, SA-58, SA-59, SA-60, SA-61, SA-62, SA-64, SA-67, SA-68, SA-69, SA-70, SA-72, SA-73, SA-93, SA-94, SA-95, SA-96, SA-97, SA-98, and both positive reference compounds 2 and 3, resulted in a significant, dose-dependent inhibition of rotenone-induced cell death. To define the relative potency of each compound, the % inhibition of cell death was plotted against the log of the dose (µM), and, when possible, the 50% inhibitory concentration ($IC_{50}$) was calculated from the dose response curve. For example, treatment with 3.5 µM SA-94 resulted in 35% inhibition of cell death and treatment with 15 SA-94 resulted in 58% inhibition of cell death, with a calculated $IC_{50}$ of 2.3 µM (FIG. 4), whereas treatment with the negative reference compound showed no inhibition of rotenone-induced cell death in this dose range (not shown). The positive results from this assay for the compounds described herein are summarized in Table 4.

Taken together, we concluded that the tested compounds that were efficacious in inhibiting rotenone-induced cytotoxicity demonstrate neuroprotective activity against α-synuclein toxicity in this system.

TABLE 4

SA compounds prevent/inhibit rotenone-induced cell death in A53T-mutant α-synuclein neuroblastoma cells

| SA # | $IC_{50}$ (µM) | Max % Inhibition |
|---|---|---|
| 52 | 23.8 | 64 |
| 58 | 3.5 | 100 |
| 59 | 3.1 | 63 |
| 60 | 12.5 | 33 |
| 61 | 3.6 | 93 |
| 62 | 3.6 | 31 |
| 64 | 2.6 | 100 |
| 67 | 8.5 | 44 |
| 68 | 24 | 61 |
| 69 | 35-75 | 30 |
| 70 | 5.6 | 78 |
| 72 | 10.3 | 39 |

TABLE 4-continued

SA compounds prevent/inhibit rotenone-induced cell death in A53T-mutant α-synuclein neuroblastoma cells

| SA # | $IC_{50}$ (µM) | Max % Inhibition |
|---|---|---|
| 73 | 35-75 | 77 |
| 93 | 19.8 | 100 |
| 94 | 2.3 | 58 |
| 95 | 3.8 | 63 |
| 96 | 4.3 | 61 |
| 97 | 39 | 42 |
| 98 | 48 | 56 |
| Positive Ref. #2 | 4.2 | 72 |
| Positive Ref. #3 | 10.6 | 82 |
| Negative Ref. | not determined | 0 |

Example 39

Compounds of this Invention Directly Inhibit the In Vitro Conversion of α-Synuclein to β-Sheet Containing Structures As described above, Thioflavin S histochemistry in α-synuclein expressing cells was used to detect aggregates containing a high degree of β-pleated sheet structures that formed in response to rotenone treatment. Since several compounds were shown to reduce the abundance of Thioflavin S-positive aggregates (Example 3), we sought independent confirmation that the compounds directly inhibit the conversion of α-synuclein to β-sheet containing structures by using circular dichroism (CD) spectroscopy. For this purpose, α-synuclein was obtained from rPeptide as a lyophilized salt in 1 mg aliquots. Buffer components and other solvents were obtained from Sigma as A.C.S. Reagent grade or higher. Wild-type α-synuclein was dissolved in a buffer containing 9.5 mM phosphate, 137 mM sodium chloride and 2.7 mM potassium chloride (phosphate-buffered saline; PBS), and the pH was adjusted to pH 7.4. This solution was then re-lyophilized and dissolved in 0.5 mL deionized water at 2 mg/mL (138 µM), and an aliquot taken and diluted to 0.05 mg/mL in PBS for CD spectral analysis (t=0, unfolded reference control). In order to induce aggregation, 1 mg/ml α-synuclein (69 µM) was incubated at 37° C. for 24 hours with shaking (1,300 rpm), either alone, or in the presence of one of the test compounds (at test compound:α-synuclein molar ratios of 5:1, 1:1, 0.5:1, 0.1:1, 0.05:1, 0.01:1). After 24 hours, reactions were diluted 20-fold in PBS and CD spectra for each reaction were acquired on a Jasco J-810 spectropolarimeter using a 0.1 cm path length cell. All spectra were recorded with a step size of 0.1 nm, a bandwidth of 1 nm, and an α-synuclein concentration of 0.05 mg/ml. The spectra were trimmed at the shortest wavelength that still provided a dynode voltage less than 600V. The trimmed spectra were then subjected to a data processing routine beginning with noise reduction by Fourier transform followed by subtraction of a blank spectrum (vehicle only without α-synuclein). These blank corrected spectra were then zeroed at 260 nm and the units converted from millidegrees to specific ellipticity.

Percent β-sheet was determined from processed spectra using the ellipticity minimum value at approximately 218 nm and referencing to a scale normalized to nearly fully folded and unfolded reference values, consistent with previous reports (Ramirez-Alvarado et al., *J. Mol. Biol.*, 273:898-912, 1997; Andersen et al., *J. Am, Chem. Soc.*, 121:9879-9880, 1999) The fully folded reference value was found by performing the described calculation on the spectrum of α-synuclein fibrillized for 24 hours (complete fibrilization), and assigning this difference the arbitrary value of 100% β-sheet. The unfolded reference was provided by the spectrum from the same sample at the initial time point (t=0) and ascribing the difference found here the arbitrary value of 0% β-sheet. These percent β-sheet values were then used to provide the respective relative % inhibition of β-sheet induced by the compounds at given molar ratio of test compound:α-synuclein. For each compound, the % inhibition of β-sheet formation was plotted against the log of the concentration (mole ratio) of the test compound and, where possible, the 50% inhibitory concentration ($IC_{50}$) was calculated from the dose response curve.

Figure 5:
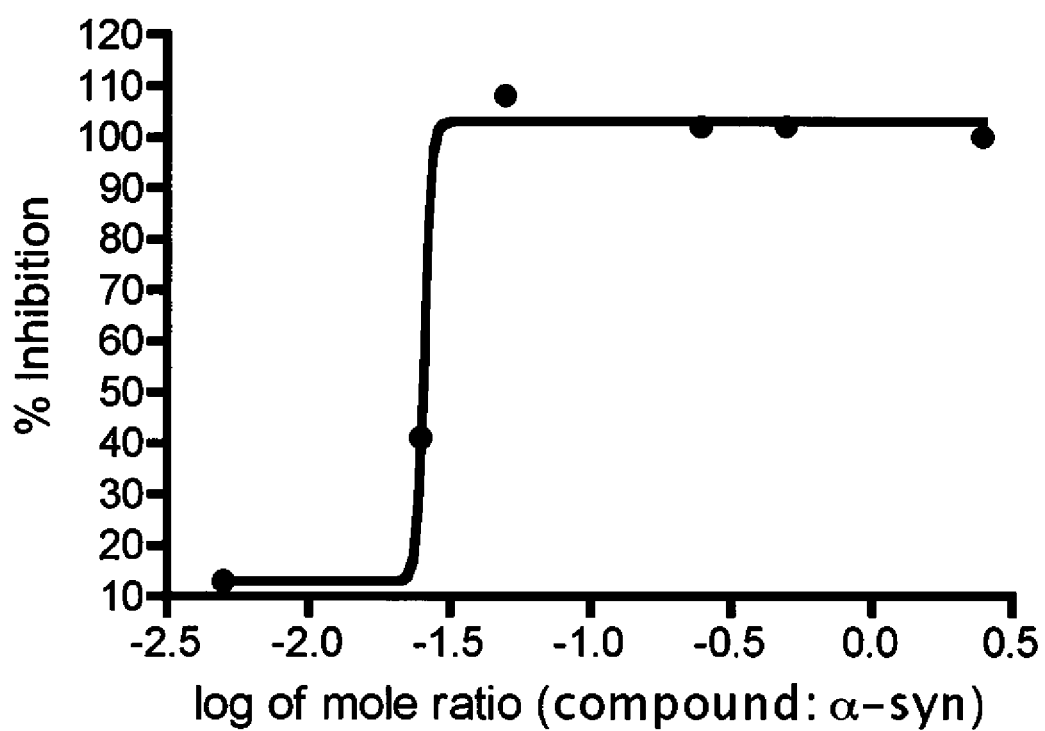
FIG. 5 is a graph illustrating that a compound of the invention causes the dose-dependent inhibition of α-synuclein β-sheet formation as assessed by circular dichroism spectroscopy.

First, in order to confirm that α-synuclein is indeed converted to a β-sheet-rich structure and to establish the timing of this conversion at 24 hours in our system, an aliquot of the α-synuclein only incubation mixture (without compounds) was sampled at various time points and CD spectra collected. At 24 hours of incubation, CD analysis revealed a large abundance of a β-sheet-rich structure, indicated by the pronounced specific ellipticity minimum at 218 nm and maximum at 197 nm (not shown). However, when test compounds SA-54, SA-55, SA-57, SA-58, SA-59, SA-61, SA-62, SA-64, SA-67, SA-68, SA-70, SA-72, SA-93, SA-94, SA-95, SA-96, SA-97, SA-98, SA-99 or positive reference compound #1 were included individually in the reaction mixture, at appropriate concentrations, and the incubation mixture sampled 24 hours later, there was an absence of the minimum at 218 nm. Instead, a spectrum characteristic of random coil was exhibited (not shown). We conclude that these compounds prevent the conversion of natively unfolded α-synuclein to a β-sheet-rich structure. These results are summarized in Table 5. As a specific example, compound SA-57 resulted in nearly complete inhibition when used at test compound:α-synuclein molar ratios ≥0.05:1, with a calculated $IC_{50}$ of 0.026 moles of compound per mole of α-synuclein (FIG. 5), whereas the negative reference compound did not significantly inhibit β-sheet formation at any of the tested molar ratios (not shown). Nearly all of the compounds that inhibited α-synuclein β-sheet formation did so at less than equimolar ratios relative to α-synuclein (i.e. $IC_{50}$ molar ratios <1), although some compounds (for example, SA-99; $IC_{50}$=2.08) required higher concentrations in order to markedly inhibit α-synuclein β-sheet formation (Table 5). Taken together, these results indicate that these SA compounds show potent inhibition and prevention of α-synuclein aggregation a hallmark of the synucleinopathies such as Parkinson's disease.

TABLE 5

SA compounds prevent/inhibit β-sheet coataining α-synuclein aggregates as assessed by circular dichroism spectroscopy.

| SA # | $IC_{50}$ (mole ratio) | Max % Inhibition |
|---|---|---|
| 54 | 0.55 | 100 |
| 55 | 0.055 | 100 |
| 57 | 0.026 | 100 |
| 58 | 0.36 | 94 |
| 59 | 0.75 | 99 |
| 61 | 0.78 | 95 |
| 62 | 0.54 | 88 |
| 64 | 0.56 | 100 |
| 67 | 0.41 | 100 |
| 68 | 0.6 | 100 |
| 70 | 0.25 | 92 |
| 72 | 0.27 | 100 |
| 93 | 0.38 | 91 |
| 94 | 0.22 | 95 |
| 95 | 0.68 | 97 |

TABLE 5-continued

SA compounds prevent/inhibit β-sheet coataining α-synuclein aggregates as assessed by circular dichroism spectroscopy.

| SA # | $IC_{50}$ (mole ratio) | Max % Inhibition |
|---|---|---|
| 96 | 0.13 | 100 |
| 97 | not determined | 100 |
| 98 | 0.08 | 100 |
| 99 | 2.08 | 98 |
| Positive Ref. #1 | 0.04 | 100 |
| Negative Ref. | not determined | none detected |

Example 40

Compounds Provided Herein Bind with High Affinity to Parkinson's Disease α-Synuclein Fibrils The compounds prepared in the preceding examples were found to bind with high affinity to α-synuclein aggregates/fibrils that are found in the hallmark Lewy Bodies of Parkinson's disease. In order to assess relative binding affinities of the test compounds for aggregated α-synuclein, competition assays were set up with a radiolabeled molecule already known to bind to α-synuclein fibrils and non-radiolabeled test compounds. In order to induce its aggregation, α-synuclein was incubated in phosphate buffered saline (PBS, pH 7.4) at 37° C. for three days with shaking (1,400 rpm). Competitive binding assays were carried out in 12×75 mm borosilicate glass tubes. The reaction mixture contained 100 μL, of α-synuclein aggregates (0.5-1 μg), [$^3$H] positive reference compound #1 (100-200 nM diluted in PBS) and 50 μl, of competing compounds ($10^{-5}$-$10^{-9}$ M, diluted serially in PBS containing 0.1% bovine serum albumin) in a final volume of 0.25 ml. Non-specific binding was defined in the presence of cold positive reference compound #1 (50 μM) in the same assay tubes. The mixture was incubated for 120 min at 37° C., and the bound and the free radioactivity were separated by vacuum filtration through Whatman GF/B filters using a Brandel M-24R cell harvester, followed by washing with PBS buffer three times. Filters containing the bound [$^3$H] positive reference compound #1 were assayed for radioactivity in a liquid scintillation counter (Beckman LS6500). $IC_{50}$ values were determined by a non-linear, least squares regression analysis. Inhibition constants (Ki) values were calculated using the equation of Cheng and Prusoff (Cheng et al., *Biochemical Pharmacology* 22:3099-3108, 1973) using the observed $IC_{50}$ of the tested compound, the concentration of radioligand employed in the assay, and the value for the Kd of the ligand (600 nM).

The results from these experiments are reported in Table 6. As an example, SA-64 binds with high affinity to α-synuclein fibrils (Ki=89 nM) but does not show significant binding affinity for the amyloid-β peptide of Alzheimer's disease (not shown). Similarly, SA-58 and SA-57 bind with high affinity to α-synuclein aggregates, with binding constants (Ki) of 105 nM and 124 nM, respectively. The increased binding affinity (by 4-5-fold) of SA-57 and SA-58, relative to positive reference molecule #1 represents a significant improvement in binding to α-synuclein aggregates for these new molecules. Taken together, these results indicate that SA compounds bind to varying degrees to the α-synuclein aggregates, a hallmark of synucleinopathies such as Parkinson's disease.

TABLE 6

SA compounds bind to α-synuclein aggregates as measured by an in vitro competition binding assay.

| SA # | $K_i$ (nM) |
|---|---|
| 52 | 1260 |
| 53 | 813 |
| 54 | 1640 |
| 55 | 370 |
| 57 | 124 |
| 58 | 105 |
| 59 | 697 |
| 61 | 3100 |
| 62 | 506 |
| 63 | 283 |
| 64 | 89 |
| 66 | 135 |
| 67 | 466 |
| 68 | 697 |
| 69 | 765 |
| 70 | 659 |
| 72 | 270 |
| 76 | 219 |
| 78 | 330 |
| 79 | 537 |
| 82 | 177 |
| 83 | 330 |
| 84 | 639 |
| 86 | 224 |
| 87 | 2000 |
| 88 | 970 |
| 89 | 1200 |
| 90 | 1700 |
| 94 | 1100 |
| 95 | 890 |
| 96 | 1350 |
| Positive reference #1 | 532 |
| negative reference #1 | no binding |
| negative reference #2 | >10000 |

Example 41

Use of Recombinant Tau Repeat Domain for In Vitro Screening of Tau Aggregation Inhibitors During in vitro screening for identification of tau aggregation inhibitors, we found that under the same experimental conditions, formation of paired helical filaments (PHFs) from commercially-purchased full-length tau protein (e.g. Tau441; rPeptide) was much slower (>11 days) than that from the tau repeat domain (TauRD; containing Q244-E372 of Tau441) (≥24 hours). Because of the remarkably short turn-around time and common aggregation properties, we used TauRD for in vitro drug screening to identify tau aggregation inhibitors [Barghorn S, Biernat J, and Mandelkow E, Purification of recombinant tau protein and preparation of Alzheimer-paired helical filaments in vitro. Methods Mol Biol, 2005. 299: p. 35-51]. Since the TauRD protein is not commercially available, we produced our own protein for this study. A cDNA fragment coding for the human TauRD (Q244-E372 of Tau441) was cloned into a bacterial expression vector and the construct was then expressed in *E. Coli*. The recombinant TauRD protein was then purified by heat-stability treatment and cation exchange chromatography as described [Barghorn, et al.,] with minor modifications. Using this method, we achieved a protein yield of 10 mg per liter of bacterial culture, with >95% purity. Aggregation and PHF formation of purified TauRD were evaluated and validated by independent assays including Thio S fluorometry, CD spectroscopy and electron microscopy (Data not shown). The results consistently demonstrate that TauRD (10 μM) is able to form Thio S-positive, β-sheet-containing PHFs when incubated with an equal concentration of heparin, at 37° C. (with shaking at 800-1000 rpm for ≥1 day).

Example 42

Identification of Novel Tau Aggregation Inhibitors by Thioflavin S Fluorometry Screening The Thio S fluorometry assay as a primary screening method to identify tau protein aggregation inhibitors from our small molecule library. Aggregated tau fibrils were prepared in the presence of equimolar ratios of TauRD and heparin (10 μM each) in 20 mM Na-phosphate buffer, pH7.4. The reaction mixture was incubated at 37° C. with shaking (800-1000 rpm) for 22-24 hr (or for 3 days). In the Thio S inhibition assays, test compounds at 0, 0.1, 1, 10 and 100 μM were added at time 0 into the reaction containing TauRD and heparin. The same reaction mixture (+/− increasing concentrations of compounds) but without TauRD were also set up in parallel to serve as background controls. For all test compounds background fluorescence readings were very low, usually <5% of those of the TauRD-containing wells. For each compound, the $IC_{50}$ was calculated using Prism version 5 software (GraphPad Software) by nonlinear regression [(Log [inhibitor] vs. normalized response; variable slope)]. In initial screening, 20 test compounds demonstrated a broad range of activities for inhibiting tau protein fibril formation: $IC_{50}$ values ranged from ~5 μM to infinity (i.e. no activity at all). The results suggested that the inhibitory activities were structure specific. The Thio S screening results are summarized in Table 7 (in which the reactions were incubated for 22 hours).

TABLE 7

SA compounds inhibit tau protein fibril formation as measured by Thioflavin S fluorometry.

| Compounds | ThioS ($IC_{50}$, μM) |
|---|---|
| SA-97 | 5.20 |
| SA-54 | 7.34 |
| SA-95 | 9.02 ± 4.66 (n = 2) |
| SA-63 | 10.08 ± 0.56 (n = 2) |
| SA-57 | 10.24 |
| SA-61 | 12.54 ± 1.24 (n = 2) |
| SA-64 | 17.61 |
| SA-96 | 21.21 |
| SA-94 | 21.44 |
| SA-99 | 24.70 |
| SA-52 | 32.83 |
| SA-68 | 33.96 |
| SA-98 | 78.51 |
| SA-70 | 117.00 |
| SA-59 | 211.10 |
| SA-72 | 290.20 |
| SA-67 | 3941.00 |
| SA-62 | no inhibition |
| SA-55 | no inhibition |
| SA-60 | no inhibition |

Example 43

Select Compounds Also Inhibit Tau Protein Formation of β-Sheet Secondary Structures Characteristic of Neurofibrillary Tangles as Determined by Circular Dichroism Spectroscopy CD spectroscopy was also performed to determine each compound's potency in inhibiting β-sheet secondary structure in TauRD under aggregation-prone conditions. The CD spectroscopy and Thio S assays were typically analyzed in parallel from the same sample preparation in order to correlate the results from two independent assays. CD spectra were taken from the samples containing +/−TauRD with increasing concentrations of compounds, and collected at 25° C. on a JASCO Model J-810 Spectropolarimeter. To determine compound inhibitory potency, we established a semi-quantitative scoring system to illustrate TauRD conformational changes on CD spectra explained below. Since CD spectra reflect a total population of secondary structures (including random coil, β-sheet, and various intermediate conformers) of TauRD proteins under a given condition, the CD scores were established based on (1) the CD spectra derived from TauRD mixtures with different ratios of random coil/β-sheet; (2) time-dependent conformational changes of TauRD. CD analysis revealed that non-aggregated TauRD proteins in solution (at time 0 in the presence of heparin, or at various times of incubation in the absence of heparin) showed spectra with ellipticity minima near 195 nm, characteristic of largely random coil structures (not shown). In contrast, aggregated and fibrillar TauRD showed spectra with minima near 218 nm, characteristic of β-sheet secondary structure (not shown). Our CD analysis studies confirmed some of our compounds that could inhibit formation of tau protein β-sheet structure.

TABLE 8

SA compounds prevent/inhibit β-sheet containing tau protein as assessed by circular dichroism spectroscopy.

| Compounds | CD |
|---|---|
| SA-97 | ++ |
| SA-54 | − |
| SA-95 | + |
| SA-63 | + |
| SA-57 | − |
| SA-61 | + |
| SA-64 | − |
| SA-96 | − |
| SA-94 | − |
| SA-99 | + |
| SA-52 | + |
| SA-68 | No data |
| SA-98 | No data |
| SA-70 | No data |
| SA-59 | − |
| SA-72 | − |
| SA-67 | n/t |
| SA-62 | n/t |
| SA-55 | − |
| SA-60 | n/t |

Table 8 summarizes data from aggregated TauRD proteins in the presence of various SA-compounds where the CD score of '−' indicates that the CD spectrum is similar to that of no compound controls with ellipticity minima at 218 nm (β-sheet) and '+' indicates that the Minima remained at 218 nm but with a reduced magnitude (intermediate conformers) and '++' indicates that the minima shifted to between 195-218 nm (intermediate conformers)

Example 44

Compositions of Compounds Provided Herein

The compounds provided herein, as mentioned previously, are desirably administered in the form of pharmaceutical compositions. Suitable pharmaceutical compositions, and the method of preparing them, are well-known to persons of ordinary skill in the art and are described in such treatises as *Remington: The Science and Practice of Pharmacy*, A. Gennaro, ed., 20th edition, Lippincott, Williams & Wilkins, Philadelphia, Pa. Representative compositions are as follows.

Oral Tablet Formulation

| | % w/w |
|---|---|
| Compound provided herein | 10.0 |
| Magnesium stearate | 0.5 |
| Starch | 2.0 |
| Hydroxypropylmethylcellulose | 1.0 |
| Microcrystalline cellulose | 86.5 |

The ingredients are mixed to homogeneity, then granulated with the aid of water, and the granulates dried. The granulate is then compressed into tablets sized to give a suitable dose of the compound. The tablet is optionally coated by applying a suspension of a film forming agent (e.g. hydroxypropylmethylcellulose), pigment (e.g. titanium dioxide), and plasticizer (e.g. diethyl phthalate), and drying the film by evaporation of the solvent. The film coat may comprise, for example, 2-6% of the tablet weight.

Oral Capsule Formulation

The granulate from the previous section of this Example is filled into hard gelatin capsules of a size suitable to the intended dose. The capsule is banded for sealing, if desired.

Softgel Formulation

A softgel formulation is prepared as follows:

| | % w/w |
|---|---|
| Compound provided herein | 20.0 |
| Polyethylene glycol 400 | 80.0 |

The compound is dissolved or dispersed in the polyethylene glycol, and a thickening agent added if required. A quantity of the formulation sufficient to provide the desired dose of the compound is then filled into softgels.

Parenteral Formulation

A parenteral formulation is prepared as follows:

| | % w/w |
|---|---|
| Compound provided herein | 1.0 |
| Normal saline | 99.0 |

The compound is dissolved in the saline, and the resulting solution is sterilized and filled into vials, ampoules, and pre-filled syringes, as appropriate.

Controlled-Release Oral Formulation

A sustained release formulation may be prepared by the method of U.S. Pat. No. 4,710,384, as follows:

One kilogram of a compound provided herein is coated in a modified Uni-Glatt powder coater with Dow Type 10 ethyl cellulose. The spraying solution is an 8% solution of the ethyl cellulose in 90% acetone to 10% ethanol. Castor oil is added as plasticizer in an amount equal to 20% of the ethyl cellulose present. The spraying conditions are as follows: 1) speed, 1 liter/hour; 2) flap, 10-15%; 3) inlet temperature, 50° C., 4) outlet temperature, 30° C., 5) percent of coating, 17%. The coated compound is sieved to particle sizes between 74 and 210 microns. Attention is paid to ensure a good mix of particles of different sizes within that range. Four hundred mg of the coated particles are mixed with 100 mg of starch and the mixture is compressed in a hand press to 1.5 tons to produce a 500 mg controlled release tablet.

The claimed subject matter is not limited in scope by the specific embodiments described herein. Indeed, various modifications of the specific embodiments in addition to those described will become apparent to those skilled in the art from the foregoing descriptions. Such modifications are intended to fall within the scope of the appended claims. Various publications are cited herein, the disclosures of which are incorporated by reference in their entireties.

The invention claimed is:

1. A compound selected from the group consisting of

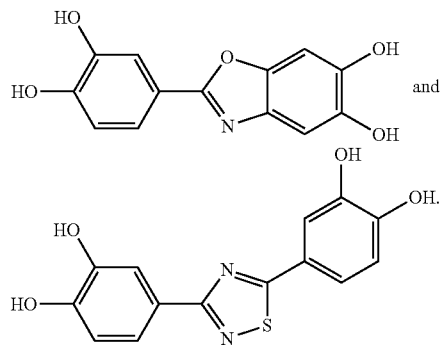

2. A method of disrupting or inhibiting the formation, deposition, accumulation, or persistence of tau fibrils and/or aggregates, comprising administering to a mammal having a tauopathy a therapeutically effective amount of the compound of claim 1.

3. The method of claim 2, where the compound administered is in an amount between 0.1 mg/Kg/day and 1000 mg/Kg/day.

4. The method of claim 2, where the compound is administered in an amount between 1 mg/Kg/day and 100 mg/Kg/day.

5. The method of claim 2, where amount of compound administered is in an amount between 10 mg/Kg/day and 100 mg/Kg/day.

6. A method resulting in neuroprotection from a tauopathy in a mammal suffering therefrom comprising the step of administrating a therapeutically effective amount of a compound of claim 1.

7. The method of claim 6 where the tauopathy is one selected from; Alzheimer's disease, Pick's disease, progressive supranuclear palsy, corticobasal degeneration, familial frontotemporal dementia/Parkinsonism linked to chromosome 17, amyotrophic lateral sclerosis/Parkinsonism-dementia complex, argyrophilic grain dementia, dementia pugilistic, diffuse neurofibrillary tangles with calcification, progressive subcortical gliosis and tangle only dementia.

8. An article of manufacture, comprising packaging material, the compound of claim 1, or a pharmaceutically acceptable salt thereof, contained within packaging material, which is used for treating the formation, deposition, accumulation, or persistence of tau fibrils and/or aggregates, and a label that indicates that the compound or pharmaceutically acceptable salt thereof is used for treating the formation, deposition, accumulation, or persistence of tau fibrils and/or aggregates.

* * * * *